US009121020B2

(12) United States Patent
Feinstein et al.

(10) Patent No.: US 9,121,020 B2
(45) Date of Patent: Sep. 1, 2015

(54) METHODS FOR TREATING EYE DISORDERS

(71) Applicant: QUARK PHARMACEUTICALS, INC., Fremont, CA (US)

(72) Inventors: Elena Feinstein, Rehovot (IL); Evgenia Alpert, Jerusalem (IL); Igor Mett, Rehovot (IL); Hagar Kalinski, Rishon-le-Zion (IL); Amir Bar-Ilan, Haifa (IL); Igor Spivak, Haifa (IL); Natanja Slager, Tel Aviv (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 0 days.

(21) Appl. No.: 14/217,079

(22) Filed: Mar. 17, 2014

(65) Prior Publication Data

US 2015/0050328 A1    Feb. 19, 2015

Related U.S. Application Data

(62) Division of application No. 13/062,161, filed as application No. PCT/US2009/061570 on Oct. 22, 2009, now Pat. No. 8,765,931.

(60) Provisional application No. 61/196,995, filed on Oct. 22, 2008, provisional application No. 61/198,931, filed on Nov. 11, 2008.

(51) Int. Cl.
*C12N 15/11* (2006.01)
*C12N 15/113* (2010.01)
*A61K 9/00* (2006.01)

(52) U.S. Cl.
CPC ............ *C12N 15/113* (2013.01); *A61K 9/0048* (2013.01); *C12N 2310/11* (2013.01); *C12N 2310/14* (2013.01)

(58) Field of Classification Search
CPC ............................ A61K 9/0048; C12N 15/113
See application file for complete search history.

(56) References Cited

U.S. PATENT DOCUMENTS

| | | |
|---|---|---|
| 6,602,858 B2 | 8/2003 | Beigelman |
| 2003/0157030 A1 | 8/2003 | Davis et al. |
| 2005/0282188 A1 | 12/2005 | Haeberli et al. |
| 2006/0172965 A1 | 8/2006 | Shepard et al. |
| 2006/0217331 A1 | 9/2006 | Vargeese et al. |
| 2011/0112168 A1 | 5/2011 | Feinstein et al. |

FOREIGN PATENT DOCUMENTS

| | | |
|---|---|---|
| WO | WO 02/24720 | 3/2002 |
| WO | WO 2004/015107 | 2/2004 |
| WO | WO 2004/078940 | 9/2004 |
| WO | WO 2004/103389 | 12/2004 |
| WO | WO 2006/023544 | 3/2006 |
| WO | WO 2008/050329 | 5/2008 |
| WO | WO 2008/104978 | 9/2008 |
| WO | WO 2009/044392 | 4/2009 |

OTHER PUBLICATIONS

Ahmed: Ocular neuroprotection by siRNA targeting caspase-2; Cell Death and Disease (2011).
Vickers et al.: Efficient Reduction of Target RNAs by Small Interfering RNA and RNase H-dependent Antisense Agents: A Comparative Analysis; The Journal of Biological Chemistry; vol. 278:7108-7118 (2003).
Muck, Hermann Am.: New ocular therapeutics: A view from the patenting perspective; IDrugs, vol. 10:1369-7056 (2007).
International Preliminary Report on Patentability, including Written Opinion of the International Searching Authority, issued Apr. 26, 2011 in connection with International application No. PCT/US2009/061570.
International Search Report, mailed Apr. 14, 2010 in connection with PCT International Application No. PCT/US2009/061570.
Second Office Action issued on Jul. 12, 2012, in connection with Chinese Application No. 200880110087.0, filed on Sep. 4, 2008.
Nov. 27, 2012 English translation of Response and claims as filed in Response to 2nd Office Action, issued on Jul. 12, 2012, in connection with Chinese Application No. 200880110087.0 filed on Sep. 4, 2008.
Extended European Search Report, issued on Dec. 6, 2011, in connection with European Patent Application No. EP 08808012.2, filed on Sep. 4, 2008.
Office Action issued on Nov. 20, 2012, in connection with European Patent Application No. EP 08808012.2, filed on Sep. 4, 2008.
Jul. 2, 2012 Response to Extended European Search Report, issued on Dec. 6, 2011, in connection with European Patent Application No. EP 08808012.2, filed on Sep. 4, 2008.
Office Action issued on Mar. 27, 2012, in connection with European Patent Application No. EP 09748890.2, filed on Oct. 22, 2009.
Sep. 25, 2012 Response to Office Action issued on Mar. 27, 2012, in connection with European Patent Application No. EP09749890.2, filed on Oct. 22, 2009.
European Search Report and Opinion issued on Aug. 26, 2011, in connection with European Patent Application No. EP 11170912.7, filed on Oct. 25, 2007.
Apr. 4, 2012 Amended Claims and Response to European Search Report and Opinion issued on Aug. 26, 2011. In connection with European Patent Application No. EP 11170912.7, filed on Oct. 25, 2007.
Office Action issued on Aug. 1, 2012, in connection with European Patent Application No. EP 11170912.7, filed on Oct. 25, 2007.
Sep. 25, 2012 Response to Office Action issued on Aug. 1, 2012, in connection with European Patent Application No. EP 11170912.7, filed on Oct. 25, 2007.

(Continued)

*Primary Examiner* — Jon E Angell
(74) *Attorney, Agent, or Firm* — Fish & Richardson P.C.

(57) ABSTRACT

The present invention relates to compositions and methods for inhibiting loss of a retinal ganglion cell in a subject, comprising non-invasively applying to the surface of the eye of the subject an ophthalmic composition comprising a therapeutically effective amount of at least one siRNA which down regulates expression of a target gene associated with loss of the retinal ganglion cell, thereby inhibiting loss of the retinal ganglion cell in the subject. The methods of the invention also relate to the use of chemically modified siRNA compounds possessing structural motifs which down-regulate the expression of human genes expressed in retinal tissue in the mammalian eye.

23 Claims, 21 Drawing Sheets

(56) References Cited

OTHER PUBLICATIONS

Notice of Acceptance issued on Oct. 11, 2012, in connection with New Zealand Patent Application No. NZ 591391, filed on Oct. 22, 2009.
Oct. 4, 2012 Response to Office Action issued on Jun. 1, 2011, in connection with New Zealand Patent Application No. NZ 591391, filed on Oct. 22, 2009.
Office Action issued Mar. 14, 2011, in connection with U.S. Appl. No. 11/978,089, filed Oct. 25, 2007.
Jan. 19, 2012 Response to Office Action issued Mar. 14, 2011, in connection with U.S. Appl. No. 11/978,089, filed Oct. 25, 2007.
Office Action issued Jul. 26, 2010, in connection with U.S. Appl. No. 11/978,089, filed Oct. 25, 2007.
Jan. 26, 2011 Response to Office Action issued Jul. 26, 2010, in connection with U.S. Appl. No. 11/978,089, filed Oct. 25, 2007.
Office Action issued Nov. 8, 2011, in connection with U.S. Appl. No. 12/733,998, filed Jan. 18, 2011.
Dec. 8, 2011 Response to Office Action issued Nov. 8, 2011, in connection with U.S. Appl. No. 12/733,998, filed Jan. 18, 2011.
Office Action issued Feb. 15, 2012, in connection with U.S. Appl. No. 12/733,998, filed Jan. 18, 2011.
May 15, 2012 Response to Off ice Action issued Feb. 15, 2012, in connection with U.S. Appl. No. 12/733,998, filed Jan. 18, 2011.
Office Action issued Dec. 14, 2012, in connection with U.S. Appl. No. 12/733,998, filed Jan. 18, 2011.
Examination Report issued by the Intellectual Property Office of New Zealand on Jun. 1, 2011, in connection with New Zealand Patent Application No. 591391, filed on Oct. 22, 2009.
Official Communication under Rules 161/162 issued by the European Patent Office on Jun. 1, 2011, in connection with European Patent Application No. 09748890.2, filed on Oct. 22, 2009.
Response to Jun. 1, 2011 Official Communication under Rules 161/162 filed with the European Patent Office on Dec. 9, 2011, in connection with European Patent Application No. 09748890.2, filed on Oct. 22, 2009.
Singh et al. (2001), "Cell specific caspase expression by different neuronal phenotypes in transient retinal eschemia", Journal of Neurochemistry, Wiley Interscience, New York, NY, US, vol. 77, No. 2.

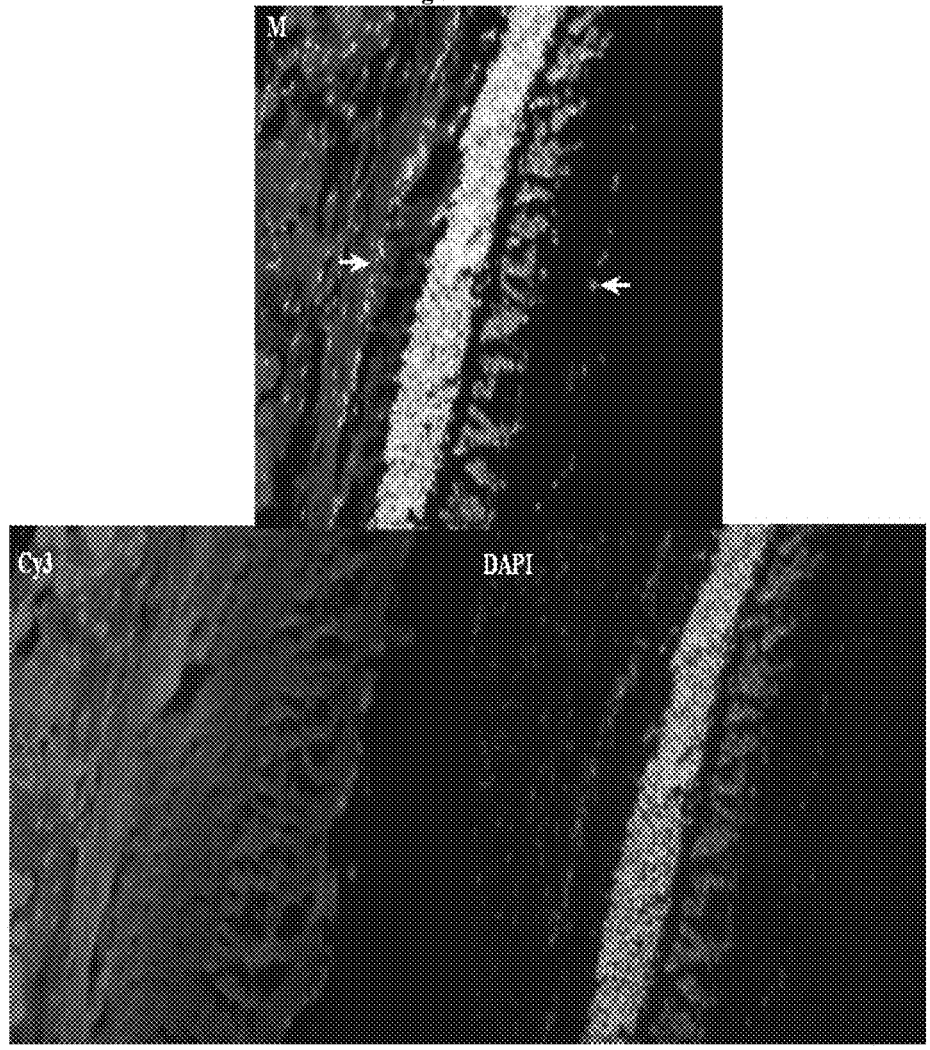

Figure 3A
Figure 3B
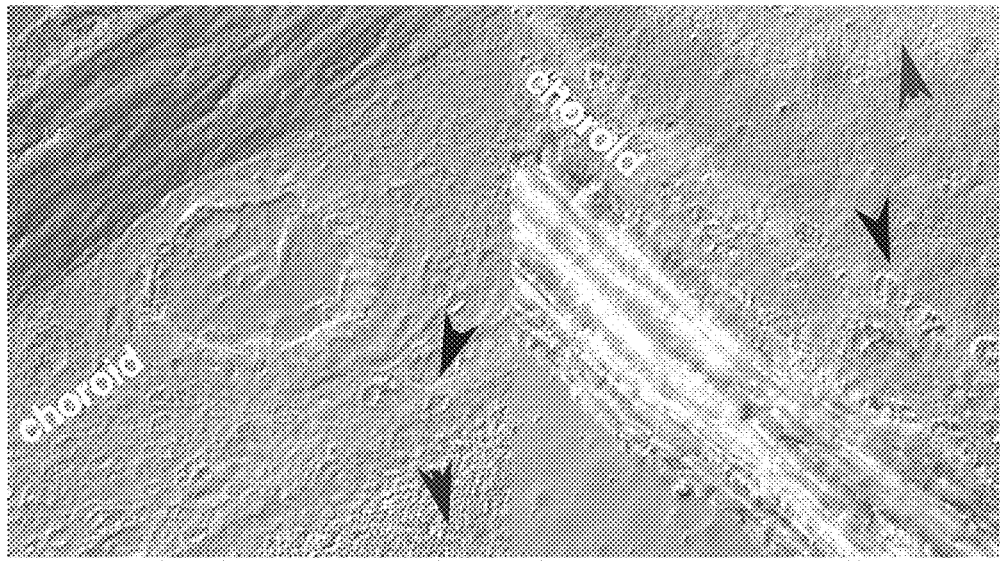
Figure 3C
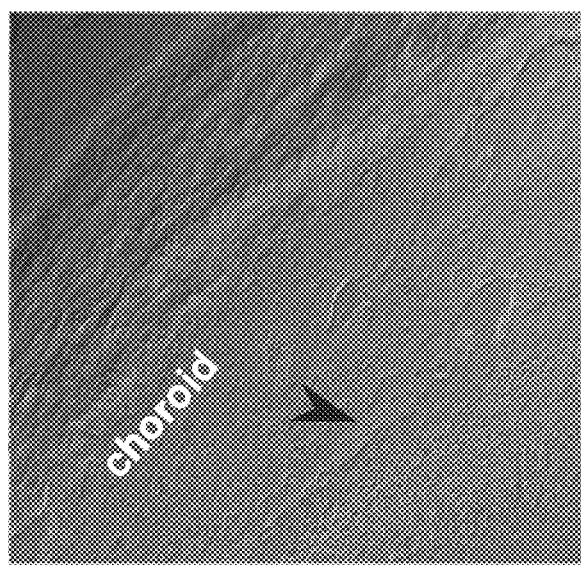

METHODS FOR TREATING EYE DISORDERS

RELATED APPLICATION

This application is a divisional of application Ser. No. 13/062,161, filed Oct. 22, 2009, which is the National Stage of International Application No. PCT/US2009/061570, filed Oct. 22, 2009, and which claims the benefit of International Application No. PCT/IL2009/000179, filed Feb. 15, 2009 and Provisional Applications No. 61/198,931, filed Nov. 11, 2008 and Provisional Application No. 61/196,995, filed Oct. 22, 2008, all of which are hereby incorporated by reference herein in their entirety.

REFERENCE TO SEQUENCE LISTING

The instant application contains a Sequence Listing which has been submitted in ASCII format via EFS-Web and is hereby incorporated by reference in its entirety. Said ASCII copy, created on Mar. 17, 2014, is named QUARK0008DV.txt and is 5935 kilobytes in size.

FIELD OF THE INVENTION

The present invention relates to a non-invasive method of treating an eye disorder in a subject in need thereof comprising the step of topically administering to the surface of the eye of the subject a pharmaceutical composition comprising a therapeutic oligonucleotide directed to a target gene associated with loss of the retinal ganglion cell in the retina of the subject. Furthermore, the invention relates to non-invasive method of promoting retinal ganglion cell survival in subject suffering from an ocular disease, disorder or injury.

BACKGROUND OF THE INVENTION

Delivery of nucleic acid compounds to retinal tissue and in particular to retinal ganglion cells presents a big drug delivery challenge. Hitherto, eye drops have been considered to be useful primarily in the treatment of anterior segment disorders since it is has been shown that nucleic acids do not pass the cornea and insufficient drug concentrations reach the posterior ocular tissue (reviewed in del Amo and Urtti, 2008. Drug Discov Today 13(3/4):135-143; Fattal and Bochot, 2006. Adv Drug Del Rev 56:1203-1223).

A retinal ganglion cell (RGC) is a type of neuron located near the inner surface of the retina of the eye. Retinal ganglion cells receive visual information from photoreceptors and collectively transmit visual information from the retina to several regions in the brain.

Further, there remains need for non-invasive method for inhibiting loss of retinal ganglion cells in a subject in need thereof. Various ocular diseases and disorders are characterized by death of retinal ganglion cells (RGCs). Accordingly, there remains a need for a non-invasive method for inhibiting loss of retinal ganglion cells (RGCs) in subjects that are suffering from an ocular disease, an ocular disorder or an ocular injury or are at risk of developing an ocular disease, an ocular disorder, or an ocular injury characterized and/or mediates by degeneration or death of retinal ganglion cells (RGCs).

SUMMARY OF THE INVENTION

The present invention is directed to non-invasive methods of treating ocular diseases, disorders and injuries that are associated with degeneration or death of retinal ganglion cells (RGCs) and to compositions useful in the methods. The methods of the invention comprise topically administering to the surface of the eye of a subject a therapeutic oligonucleotide composition useful in promoting survival of retinal ganglion cells in a subject. Hitherto, oligonucleotides have been delivered to retinal ocular tissue by systemic delivery or intravitreal injection, methods associated with detrimental side effects and poor patient compliance, respectively. The present invention provides topical ophthalmic compositions comprising an oligonucleotide, and non-invasive methods of use thereof for down regulating expression of a target gene associated with loss of the retinal ganglion cell in the retina of a subject, for rescuing retinal ganglion cells from apoptosis and for treating eye disorders.

Accordingly, in one aspect the present invention provides a method of non-invasive delivery of an oligonucleotide to a retinal tissue in a subject suffering from an eye disorder, disease or injury comprising topically applying an ophthalmic composition comprising the oligonucleotide to the surface of the eye of the subject.

In another aspect the present invention provides a method of non-invasive delivery of an oligonucleotide to a retinal ganglion cell in a subject suffering from an eye disorder comprising topically applying an ophthalmic composition comprising the oligonucleotide to the surface of the eye of the subject.

In yet another aspect, the present invention provides a method of attenuating expression of a target gene associated with loss of a retinal ganglion cell in the retina in a subject suffering from an ocular disease, disorder or injury, which comprises topically (non-invasively) administering to the surface of the eye of the subject a pharmaceutical composition comprising at least one oligonucleotide directed to the target mRNA product of the target gene, in an amount and over a period of time effective to attenuate expression of the gene in the retina of the subject.

In a further aspect, the present invention provides a method of treating a subject suffering from retinal ganglion cell loss or retinal ganglion cell damage and providing ocular neuroprotection to a subject suffering from or at risk of developing an eye disease, disorder or injury. The method comprises topically administering to the surface of the eye of the subject an ophthalmic pharmaceutical composition comprising at least one oligonucleotide directed to a target gene in the retina of the subject, in an amount and over a period of time effective to inhibit retinal ganglion cell loss or retinal ganglion cell damage in the subject.

In various embodiments the ophthalmic pharmaceutical composition is formulated as a cream, a foam, a paste, an ointment, an emulsion, a liquid solution including an eye drop, a gel, spray, a suspension, a microemulsion, microspheres, microcapsules, nanospheres, nanoparticles, lipid vesicles, liposomes, polymeric vesicles, a patch, or a contact lens. In some embodiments the pharmaceutical composition is formulated as an eye drop. In preferred embodiments the ophthalmic composition is administered to the eye, for example, by instillation of an eye drop or by administration of a mist.

In certain embodiments the at least one target ocular mRNA is selected from an mRNA polynucleotide set forth in any one of SEQ ID NOS:1-58. In certain embodiments the at least one target gene is selected from a gene transcribed into an mRNA polynucleotide set forth in any one of SEQ ID NOS:1-58.

In some embodiments the at least one oligonucleotide is selected from chemically modified siRNA, unmodified siRNA, antisense, ribozyme, miRNA and shRNA. In preferred embodiments the at least one oligonucleotide is a chemically modified siRNA. In some embodiments the siRNA sense and antisense oligonucleotides are selected from sense and corresponding antisense oligonucleotide pairs shown in Tables B1-B36, set forth in SEQ ID NOS:59-33,596.

In some embodiments the eye disorder, disease or injury is selected from glaucoma, dry eye, diabetic retinopathy (DR), diabetic macular edema (DME) or age related macular degeneration (AMD). In other embodiments the ocular disorder, disease or injury is optic neuritis, central retinal vein occlusion, brunch retinal vein occlusion (BRVO). In further embodiments the eye disorder, disease or injury is retinitis pigmentosa (RP), ischemic optic neuropathy or optic nerve injury. In further embodiments ocular disorder, disease or injury is retinopathy of prematurity (ROP) retinal ganglion degeneration, macular degeneration, hereditary optic neuropathy, metabolic optic neuropathy, optic neuropathy due to a toxic agent or neuropathy caused by adverse drug reactions or vitamin deficiency. In yet another embodiment the disorder is vision loss associated with a tumor.

In various embodiments the at least one siRNA compound is delivered to the eye of a subject as a liquid solution, including an eye drop. In various embodiments the present invention provides a method for attenuating expression of a target ocular gene associated with loss of a retinal ganglion cell in a subject suffering from an ocular disease, disorder or injury, comprising topically applying to the surface of the eye of the subject an ophthalmic pharmaceutical composition formulated as an eye drop.

In various embodiments expression of a target ocular mRNA is attenuated in an ocular cells in the retina of a subject suffering from an eye disease, disorder, or injury. In various embodiments the ocular cell includes but is not limited to an acinar cell of the lacrimal gland, a ductal cell of the lacrimal gland, a retinal ganglion cell (RGC), a retinal pigment epithelial (RPE) cell, a choroidal cell, a corneal cell, a cell of the ciliary process or a cell of the trabecular meshwork or a combination thereof.

The present invention provides a method for inhibiting loss of a retinal ganglion cell in a subject, comprising non-invasively administering to the surface of the eye of the subject an ophthalmic composition comprising a therapeutically effective amount of at least one siRNA which down regulates expression of a target gene associated with loss of the retinal ganglion cell in the retina of the subject, thereby inhibiting loss of a retinal ganglion cell. In certain embodiments two or more target genes are down regulated by the method according to the invention. In certain embodiments attenuating expression of at least one target gene (ocular mRNA) associated with loss of the retinal ganglion cell in the retina of the subject confers upon the eye neuroprotective properties. In various embodiments the at least one ocular target gene is selected from the list in Tables A1 to A4, set forth in SEQ ID NO:1-58.

In one embodiment the eye disorder is glaucoma. Thus the present invention provides a method of inhibiting loss of a retinal ganglion cell in a subject suffering from glaucoma comprising topically (non-invasively) applying to the surface of the eye of the subject an ophthalmic composition comprising a therapeutically effective amount of at least one siRNA which down regulates a target gene (target ocular mRNA) associated with loss of the retinal ganglion cell in the retina of the subject, thereby inhibiting loss of a retinal ganglion cell in the subject's eye. In preferred embodiments the siRNA is chemically modified. In some embodiments the chemically modified siRNA attenuates expression of gene (target ocular mRNA) in the retina of the subject's eye. In other embodiments the chemically modified siRNA attenuates expression of target ocular mRNA in the optic nerve of the subject's eye. In certain embodiments attenuating expression of at least one target gene (ocular mRNA) associated with loss of the retinal ganglion cell in the retina of the subject is effective to treat glaucoma. In certain embodiments the at least one target gene is selected from the list in Table A1 set forth in SEQ ID NO:1-35. In certain preferred embodiments the target gene is selected from CASP2 (SEQ ID NO:1-2), ASPP1 (SEQ ID NO:4), TP53BP2 (SEQ ID NO:6-7), BNIP3 (SEQ ID NO:12), RTP801L (SEQ ID NO:14), ACHE (SEQ ID NO:19-20), ADRB1 (SEQ ID NO:21) and CAPNS1 (SEQ ID NO:28-29). In various embodiments the gene is set forth in SEQ ID NOS:1-2. In some embodiments the siRNA sense and antisense strands are selected from pairs of oligonucleotide sequences set forth in SEQ ID NOS:8515-9516.

In another embodiment the eye disorder is dry-eye. Thus the present invention provides a method of inhibiting loss of a retinal ganglion cell in a subject suffering from dry-eye. The method comprises topically (non-invasively) administering to the surface of the eye of the subject an ophthalmic composition comprising a therapeutically effective amount of at least one siRNA which down regulates a target gene (target ocular mRNA) associated with loss of the retinal ganglion cell in the retina of the subject, thereby inhibiting loss of a retinal ganglion cell in the subject's eye. In preferred embodiments the siRNA is chemically modified. In certain embodiments attenuating expression of at least one target ocular mRNA is effective to treat dry-eye disorder. In certain embodiments attenuating expression of at least one target gene associated with loss of retinal ganglion cells is effective to reduce the symptoms of dry-eye. In certain embodiments the at least one target gene (ocular target mRNA) is expressed in retinal ganglion cell in the eye of the subject. In certain embodiments the at least one target gene (ocular target mRNA) is expressed in the lacrimal gland in the eye of the subject. In certain embodiments the at least one target gene is selected from Table A2 set forth in any one of SEQ ID NO: 5 (p53), SEQ ID NO:8-10 (LRDD), SEQ ID NO:26-27 (SHC1) and SEQ ID NO:30-44 (FAS and FAS ligand). In some embodiments the target gene is selected from FAS, FAS ligand (FASL), p53, LRDD, PARP1, AIF (apoptosis inducing factor), NOS1, NOS2A, XIAP and SHC1-SHC. In certain preferred embodiments the target gene is set forth in any one of SEQ ID NO:36-SEQ ID NO: 43 or SEQ ID NO:44. In some embodiments the siRNA sense and antisense strands are selected from pairs of oligonucleotide sequences set forth in SEQ ID NOS: 13,225-15,224.

In another embodiment the eye disorder is AMD, DR or DME. Thus, the present invention provides a method of inhibiting loss of a retinal ganglion cell in a subject suffering from AMD, DR or DME. The method comprises topically (non-invasively) administering to the surface of the eye of the subject an ophthalmic composition comprising a therapeutically effective amount of at least one siRNA which down regulates a target gene (target ocular mRNA) associated with loss of the retinal ganglion cell in the retina of the subject, thereby inhibiting loss of a retinal ganglion cell in the subject's eye. In preferred embodiments the siRNA is chemically modified. In certain embodiments attenuating expression of at least one target gene associated with loss of retinal ganglion cells is effective to treat AMD, DR or DME. In certain embodiments attenuating expression of at least one target gene associated with loss of retinal ganglion cells is effective to reduce the symptoms of AMD, DR or DME. In certain embodiments the administration of at least one siRNA attenuates expression of at least one target gene (ocular mRNA) in a retinal ganglion cell in the subject's eye. In certain embodiments the administration of at least one siRNA attenuates expression of at least one target gene (target ocular mRNA) in the choroid in the subject's eye. In certain embodiments the at least one target gene is listed in Table A3 set forth in any one of SEQ ID NOS:1-2, 3, 5, 6-7, 8-10, 12, 13, 24-25, 26-27, 30-35, 45-53. In certain preferred embodiments the siRNA targets CTSD, RTP801 and BNIP3. In certain preferred embodiments the disorder is DR and the siRNA targets mRNA set forth in SEQ ID NOS:48-53. In some embodiments the siRNA sense and antisense strands are selected from any one of sequences set forth in SEQ ID NOS:24575-29594. In certain preferred embodiments the disorder is AMD and the siRNA targets gene set forth in SEQ ID NO:3 and the siRNA sense and antisense strands are selected from any one of sequences set forth in SEQ ID NOS:11285-12224. In some embodiments the siRNA sense and antisense strands are selected from pairs of oligonucleotide sequences set forth in SEQ ID NOS:24575-29594.

In a further embodiment the eye disorder is Retinitis pigmentosa (RP). Thus, the present invention provides a method of inhibiting loss of a retinal ganglion cell in a subject suffering from RP. The method comprises topically (non-invasively) administering to the surface of the eye of the subject an ophthalmic composition comprising a therapeutically effective amount of at least one siRNA which down regulates a target gene (target ocular mRNA) associated with loss of the retinal ganglion cell in the retina of the subject, thereby inhibiting loss of a retinal ganglion cell in the subject's eye. In preferred embodiments the siRNA is chemically modified. In certain embodiments attenuating expression of at least one target gene associated with loss of retinal ganglion cells is effective to RP. In certain embodiments attenuating expression of at least one target gene associated with loss of retinal ganglion cells is effective to reduce the symptoms of RP. In certain embodiments the at least one target ocular mRNA is product of a gene selected from a gene listed in Table A4 which is transcribed into mRNA set forth in any one of SEQ ID NOS: 3, 14, 26-35, 54-57. In some embodiments the target ocular mRNA is product of a gene selected from the group consisting of CASP1, CASP3, CASP12, RTP801, RTP801L, CAPNS1, PARP1, AIF, NOS1, NOS2, XIAP and SHC1-SHC. In certain preferred embodiments the siRNA targets mRNA set forth in SEQ ID NOS:56-57.

In another aspect the invention features a method of rescuing a retinal ganglion cell from apoptosis in a subject, comprising non-invasively applying to the surface of the eye of the subject an ophthalmic composition comprising a therapeutically effective amount of at least one siRNA to a target gene in the retina of the subject, thereby rescuing retinal ganglion cell from apoptosis in the subject. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotides shown in tables B1-B36 and set forth in SEQ ID NOS:59-33,596.

In another aspect, the invention provides method for promoting survival of a retinal ganglion cell in a subject displaying signs or symptoms of an ocular neuropathy, comprising non-invasively administering to the surface of the eye of the subject an ophthalmic composition comprising a therapeutically effective amount of at least one siRNA to a target gene in the retina of the subject, thereby promoting survival of a retinal ganglion cell in the subject. In preferred embodiments the at least one siRNA is a chemically modified. In certain embodiments the signs or symptoms of an ocular neuropathy are mediated by apoptosis. In some embodiments the target gene is set forth in any one of SEQ ID NO:1-58. In various embodiments the siRNA sense and antisense oligonucleotides are selected from sense and corresponding antisense oligonucleotides set forth in SEQ ID NOS:59-33,596.

In yet another aspect, the invention is directed to a method for preventing, treating or alleviating the effects of an ocular disease associated with death of a retinal ganglion cell in a subject, comprising non-invasively applying to the surface of the eye of the subject an ophthalmic composition comprising a therapeutically effective amount of at least one siRNA to a target gene in the retina of the subject, thereby preventing, treating or alleviating the effects of an ocular disease associated with death of a retinal ganglion cell in the subject. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotide pairs shown in Tales B1-B36, set forth in SEQ ID NOS:59-33,596.

Another aspect of the invention provides for a method for treating or preventing retinal ganglion cell death in a subject, comprising non-invasively applying to the surface of the eye of the subject an ophthalmic pharmaceutical composition which comprises: (a) a therapeutically effective amount of at least one siRNA to a target gene in the retina of the subject, and (b) a pharmaceutically acceptable excipient or carrier or mixture thereof, and thereby treating or preventing retinal ganglion cell death in the subject. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotides set forth in SEQ ID NOS:59-33,596.

In another aspect, the present invention is directed to a method preventing retinal ganglion cell death mediated by elevated intraocular pressure (IOP) in the eye of a subject, comprising non-invasively administering to the surface of the eye of the subject an ophthalmic composition comprising a therapeutically effective amount of at least one siRNA to a target gene in the retina of the subject, thereby preventing retinal ganglion cell death in the subject. In preferred embodiments the at least one siRNA is a chemically modified. In a particular embodiment according to this method the subject is afflicted with glaucoma. In some embodiments the target gene is set forth in any one of SEQ ID NO:1-58. In various embodiments the siRNA sense and antisense oligonucleotides are selected from sense and corresponding antisense oligonucleotides set forth in SEQ ID NOS:59-33,596.

The present invention further provides a method of delaying, preventing or rescuing a retinal cell from death in a subject suffering from elevated IOP comprising non-invasively applying to the surface of the eye of the subject an ophthalmic composition comprising a therapeutically effective amount of at least one siRNA to a target gene associated with death of the RGC in the retina of the subject, thereby delaying, preventing or rescuing the retinal cell from injury or death and wherein intraocular pressure (IOP) remains substantially elevated. In preferred embodiments the at least one siRNA is a chemically modified. In a particular embodiment according to this method the subject is afflicted with glaucoma. In some embodiments the target gene is set forth in any one of SEQ ID NO:1-58. In various embodiments the siRNA sense and antisense oligonucleotides are selected from sense and corresponding antisense oligonucleotides set forth in SEQ ID NOS:59-33,596.

The present invention further provides a method of treating a subject suffering from retinal ganglion cell loss or retinal ganglion cell damage, comprising non-invasively administering to the surface of the eye of the subject an ophthalmic composition comprising a therapeutically effective amount of at least one siRNA to a target gene in the retina of the subject, thereby treating the subject or reducing retinal ganglion cell death in the subject. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotides set forth in SEQ ID NOS:59-33,596.

The present invention further provides a method for lowering retinal ganglion cell loss and providing ocular neuroprotection to a subject in need thereof, comprising non-invasively applying to the surface of the eye of the subject an ophthalmic composition comprising a therapeutically effective amount of at least one siRNA to a target gene in the retina of the subject, thereby lowering retinal ganglion cell loss and providing ocular neuroprotection to the subject. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotide pairs shown in Tables B1-B36, set forth in SEQ ID NOS:59-33,596.

The present invention further provides a method for preventing visual field loss associated with loss of retinal ganglion cells in a subject, comprising non-invasively administering to the surface of the eye of the subject an ophthalmic composition comprising a therapeutically effective amount of at least one siRNA to a target gene in the retina of the subject, thereby preventing visual field loss in the subject. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotide pairs shown in Tables B1-B36, set forth in SEQ ID NOS:59-33,596.

In another aspect, the present invention provides an ophthalmic composition for non-invasive treatment of an ocular disease associated with loss of a retinal ganglion cell in a subject, comprising: (a) a therapeutically effective amount of at least one siRNA to a target gene in the retina of the subject, and (b) a pharmaceutically acceptable excipient or carrier or mixture thereof. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotide pairs shown in Tables B1-B36, set forth in SEQ ID NOS:59-33,596.

In yet another aspect, the present invention provides a topical ophthalmic pharmaceutical composition for non-invasive treatment of an ocular disease associated with pathological abnormalities/changes in the tissues of the visual system, comprising: (a) a therapeutically effective amount of at least one siRNA to a target gene in the retina of the subject, wherein the target gene is set forth in any one of SEQ ID NO:1-58, and (b) a pharmaceutically acceptable excipient or carrier or mixture thereof. In preferred embodiments the at least one siRNA is a chemically modified. In various embodiments the siRNA sense and antisense oligonucleotides are selected from sense and corresponding antisense oligonucleotide pairs shown in Tables B1-B36, set forth in SEQ ID NOS:59-33,596.

According to another aspect, the present invention is directed to a topical ophthalmic pharmaceutical composition for use in treating a subject afflicted with ocular disease associated with death of retinal ganglion cells, which comprises: (a) a therapeutically effective amount of at least one siRNA to a target gene in the retina of the subject, wherein the target gene is set forth in any one of SEQ ID NO:1-58, and (b) a pharmaceutically acceptable excipient or carrier or mixture thereof. In preferred embodiments the at least one siRNA is a chemically modified. In various embodiments the siRNA sense and antisense oligonucleotides are selected from sense and corresponding antisense oligonucleotide pairs shown in Tables B1-B36, set forth in SEQ ID NOS:59-33,596.

In various embodiments the ocular disease is selected from a group comprising glaucoma, dry eye, diabetic retinopathy (DR), diabetic macular edema (DME), age related macular degeneration (AMD), optic neuritis, central retinal vein occlusion, brunch retinal vein occlusion, ischemic optic neuropathy, optic nerve injury, retinopathy of prematurity (ROP) or retinitis pigmentosa (RP), retinal ganglion degeneration, macular degeneration, hereditary optic neuropathy, metabolic optic neuropathy, neuropathy due to a toxic agent or that caused by adverse drug reactions or vitamin deficiency; and the composition is formulated as a cream, a foam, a paste, an ointment, an emulsion, a liquid solution, an eye drop, a gel, spray, a suspension, a microemulsion, microspheres, microcapsules, nanospheres, nanoparticles, lipid vesicles, liposomes, polymeric vesicles, a patch, a biological insert. In a preferred embodiment the composition is formulated as an eye drop.

In another aspect the invention is directed to a packaged pharmaceutical preparation, comprising: (a) a pharmaceutical composition according to the invention in a container; and (b) instructions for using the composition to treat an ocular disease. In various embodiments the pharmaceutical composition according to present invention comprises a therapeutically effective amount of at least one siRNA to a target gene in the retina of the subject suffering from an ocular disease. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotides set forth in SEQ ID NOS:59-33,596. In one particular embodiment according to this aspect of the invention, the pharmaceutical composition is for non-invasive treatment of an ocular disease associated with loss of a retinal ganglion cell in a subject. In another particular embodiment according to this aspect the invention, the pharmaceutical composition is for non-invasive treatment of an ocular disease associated with pathological abnormalities/changes in the tissues of the visual system. In yet another particular embodiment according to this aspect the invention, the pharmaceutical composition is for use in treating a subject afflicted with ocular disease associated with death of retinal ganglion cells.

According to another aspect, the invention is directed to use of a pharmaceutical composition according to the invention in the manufacture of a medicament for promoting retinal ganglion cell survival in a subject. In various embodiments the pharmaceutical composition according to present invention comprises a therapeutically effective amount of at least one siRNA to a target gene in the retina of the subject suffering from an ocular disease. In preferred embodiments the at least one siRNA is a chemically modified. In some embodiments the target gene is set forth in any one of SEQ ID NO:1-58. In various embodiments the siRNA sense and antisense oligonucleotides are selected from sense and corresponding antisense oligonucleotide pairs shown in Tables B1-B36, set forth in SEQ ID NOS:59-33,596. In one particular embodiment according to this aspect the invention the pharmaceutical composition is for non-invasive treatment of an ocular disease associated with loss of a retinal ganglion cell in a subject. In another particular embodiment according to this aspect the invention the pharmaceutical composition is for non-invasive treatment of an ocular disease associated with pathological abnormalities/changes in the tissues of the visual system. In yet another particular embodiment according to this aspect the invention the pharmaceutical composition is for use in treating a subject afflicted with ocular disease associated with death of retinal ganglion cells.

In some embodiments the composition includes a viscosity enhancing agent. A viscosity enhancing agent is selected from for example a hydrophilic polymer including cellulose and cellulose derivatives methylcellulose and methylcellulose derivatives. Such agents include methylcellulose, hydroxyethyl cellulose, hydroxypropyl cellulose, hydroxypropylmethyl cellulose, carboxymethyl cellulose, derivatives thereof, combinations thereof and their salts. In some embodiments the viscosity enhancing agent is methylcellulose. In certain embodiments the viscosity enhancing agent is provided at a concentration of about 0.01% to about 4%, in other embodiments the viscosity enhancing agent is provided at a concentration of about 0.1% to about 3%, or at a concentration of about 0.5% to about 2%.

In some embodiments the composition includes an agent providing osmotic balance, or a surfactant. Such agents include glycerol, ethylene glycol, poly(ethylene glycol), propylene glycol, sorbitol, mannitol, monosaccharide, disaccharides and oligosaccharides.

The present invention further provides a method of treating glaucoma in a subject in need of treatment that comprises topically (non-invasively) administering to the surface of the eye of the subject a therapeutically effective amount of at least one siRNA to a target gene in the eye of the subject, in an amount effective to treat glaucoma. In certain preferred embodiments the siRNA chemically modified siRNA. In certain embodiments the at least one siRNA inhibits expression of at least one gene expressed in the retina of the subject's eye. In certain embodiments inhibition of at least one gene confers upon the eye neuroprotective properties. In certain embodiments the at least one gene is selected from a list in Table A1 transcribed into mRNA set forth in SEQ ID NO:1-35. In certain preferred embodiments the gene is selected from CASP2 (SEQ ID NO:1-2), ASPP1 (SEQ ID NO:4), TP53BP2 (SEQ ID NO:6-7), BNIP3 (SEQ ID NO:12), RTP801L (SEQ ID NO:14), ACHE (SEQ ID NO:19-20), ADRB1 (SEQ ID NO:21) and CAPNS1 (SEQ ID NO:28-29). In various embodiments the gene is set forth in SEQ ID NOS:1-2. In some embodiments the siRNA sense and antisense strands are selected from any one of sequences set forth in SEQ ID NOS:8515-9516.

The present invention further provides a method of treating dry-eye in a subject in need thereof, which comprises topically (non-invasively) applying to the surface of the eye of the subject a therapeutically effective amount of at least one siRNA which inhibits expression of at least one gene expressed in the eye of the subject in an amount effective to reduce the symptoms of dry eye. In certain preferred embodiments the siRNA is chemically modified siRNA. In certain embodiments the at least one gene is expressed in the lacrimal gland in the subject. In certain embodiments the at least gene is selected from Table A2 set forth in any one of SEQ ID NO: 5, SEQ ID NO:8-10, SEQ ID NO:26-27 and SEQ ID NO:30-44. In some embodiments the gene is selected from FAS, FAS ligand (FASL), p53, LRDD, PARP1, AIF (apoptosis inducing factor), NOS1, NOS2A, XIAP and SHC1-SHC. In certain preferred embodiments the gene is transcribed into mRNA set forth in any one of SEQ ID NO:36-SEQ ID NO:44. In some embodiments the siRNA sense and antisense strands are selected from any one of sequences in Tables 16-17 set forth in SEQ ID NOS: 13,225-15,224.

The present invention further provides a method of treating AMD, DR or DME in a subject in need thereof, which comprises topically (non-invasively) administering to the surface of the eye of the subject a therapeutically effective amount of at least one siRNA which inhibits expression of at least one gene expressed in the eye in the subject in an amount effective to reduce the symptoms of AMD, DR or DME. In certain preferred embodiments the siRNA is chemically modified siRNA. In certain embodiments the at least one siRNA inhibits expression of at least one gene expressed in the choroid in the subject's eye. In certain embodiments the at least one target ocular mRNA listed in Table A3, set forth in any one of SEQ ID NOS:1-2, 3, 5, 6-7, 8-10, 12, 13, 24-25, 26-27, 30-35, 45-53. In certain preferred embodiments the siRNA targets CTSD, RTP801 and BNIP3. In certain preferred embodiments the disorder is DR and the siRNA targets mRNA set forth in SEQ ID NOS:48-53.

In a further embodiment the eye disorder is Retinitis pigmentosa (RP). Thus, the present invention provides a method of attenuating expression of a target ocular mRNA in the eye of a subject suffering from RP. The method comprises topically (non-invasively) applying to the surface of the eye of the subject a therapeutically effective amount of at least one siRNA to a target gene in the eye of the subject. In certain preferred embodiments the siRNA is chemically modified siRNA. In certain embodiments attenuating expression of at least one target gene (target ocular mRNA) is effective to treat RP. In certain embodiments attenuation of at least one target ocular mRNA is effective to reduce the symptoms of RP. In certain embodiments the at least one target ocular mRNA is product of a gene selected from a gene listed in Table A4 which is transcribed into mRNA set forth in any one of SEQ ID NOS: 3, 14, 26-35, 54-57. In some embodiments the target ocular mRNA is product of a gene selected from the group consisting of CASP1, CASP3, CASP12, RTP801, RTP801L, CAPNS1, PARP1, AIF, NOS1, NOS2, XIAP and SHC1-SHC. In certain preferred embodiments the siRNA targets mRNA set forth in SEQ ID NOS:56-57.

In various embodiments the at least one siRNA is chemically modified. In various embodiments the at least one siRNA comprises a sufficient number of consecutive nucleotides having a sequence of sufficient homology to a nucleic acid sequence present within the target mRNA to hybridize to the mRNA and attenuate expression of the mRNA in the eye of the subject.

In various embodiments the at least one siRNA comprises a sufficient number of consecutive nucleotides having a sequence of sufficient homology to a nucleic acid sequence present within the gene to hybridize to the gene and reduce or inhibit expression of the gene in the eye of the subject.

BRIEF DESCRIPTION OF THE FIGURES

FIGS. 1A-C: Representative images of Cy3 labeled DDIT4 siRNA incorporated into murine retina following eye drop administration.

FIG. 3A shows accumulation of Cy3-siRNA in rat choroid after administration by eye drops 10 minutes post administration.

FIG. 3B shows accumulation of Cy3-siRNA in rat choroid after administration by eye drops 1 hour post administration.

FIG. 3C shows accumulation of Cy3-siRNA in rat choroid after administration by eye drops 4 hours post administration.

FIG. 6B shows accumulation of DDIT4_1 Cy3-siRNA 1 hour post administration by eye drops. Choroid, outer nuclear layer, RPE and outer segment layer of photoreceptor cells show Cy3 staining.

DETAILED DESCRIPTION OF THE INVENTION

Figure 1B:
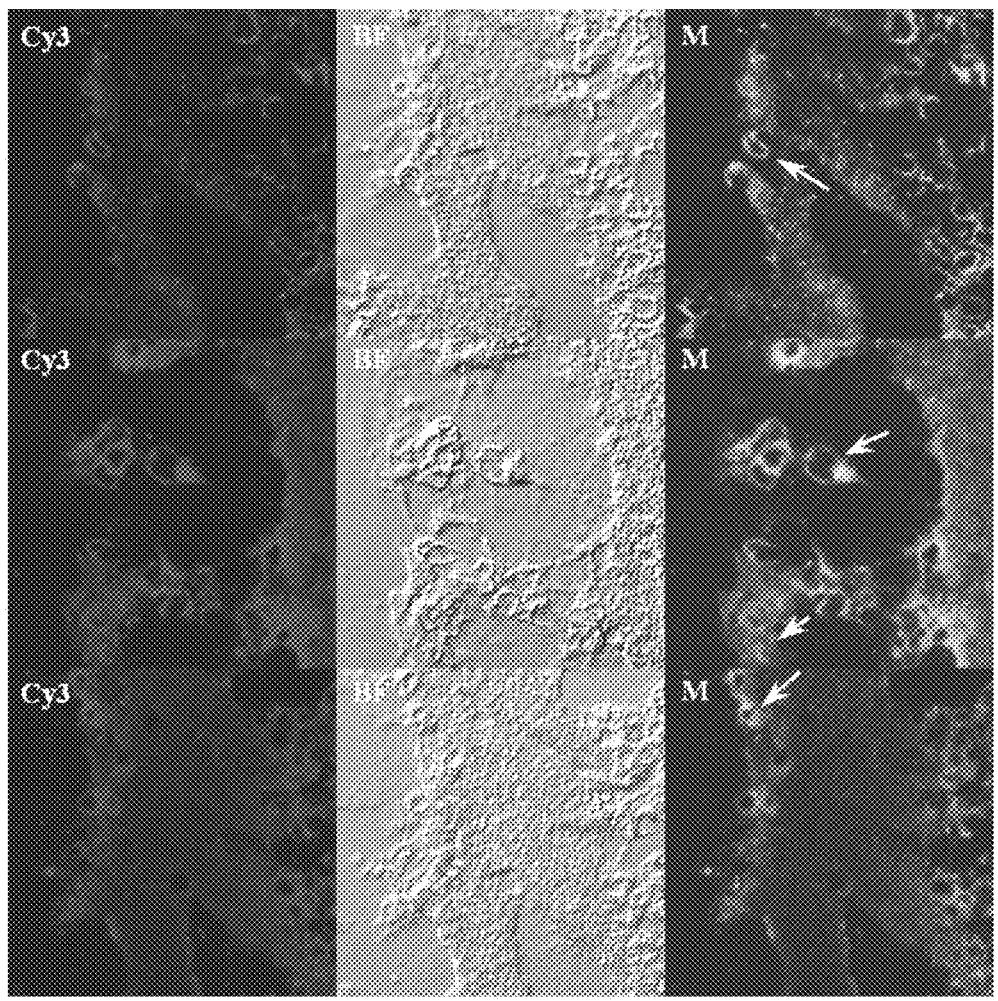
Figure 1C:
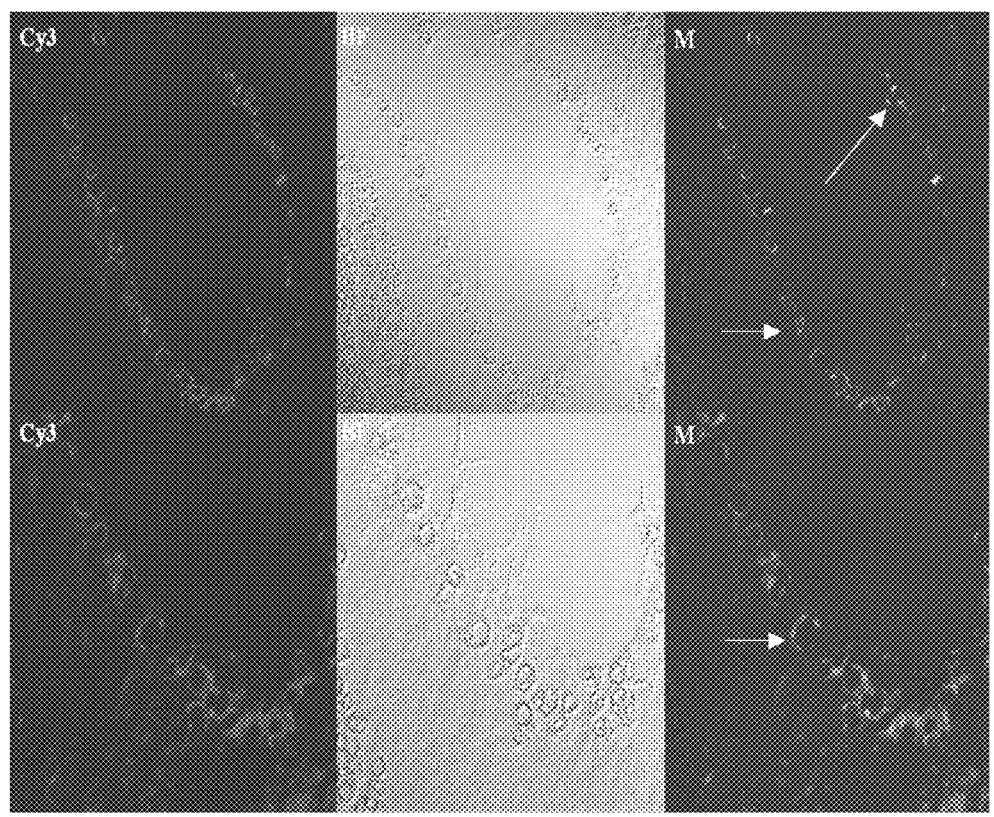

The present invention provides topical oligonucleotide compositions and non-invasive methods of use thereof for treating various eye diseases and disorders. In particular, the invention provides methods for treatment of various eye diseases and disorders associated with gene expression in the eye of a subject suffering from the disease or disorder.

The present invention is based in part on the unexpected discovery that topical non-invasive administration of siRNA compositions targets certain ocular tissues and cell types and is active in those tissues and cells when delivered topically to the surface of the eye. The discovery is surprising in view of the known obstacles to siRNA delivery and provides non-invasive methods as a realistic alternative to intravitreal or systemic delivery.

For siRNA molecules to be effective in silencing mRNA of a target gene, the siRNA requires three levels of targeting: to the target tissue, to the target cell type and to the target subcellular compartment. The present invention now discloses non-invasive methods of treating eye diseases and disorders.

The present invention relates in general to compounds which down-regulate expression of genes expressed in ocular cells, particularly to novel small interfering RNAs (siRNAs), and to the use of these novel siRNAs in the treatment of a subject suffering from medical conditions associated with expression of those genes in eye tissues and cells.

Methods for attenuating expression of an ocular target mRNA and methods of treating disorders in the eye are discussed herein at length, and any of said molecules and/or compositions may be beneficially employed in the treatment of a subject suffering from any of said conditions.

The siRNAs of the present invention possess structures and modifications which may increase activity, increase stability, and or minimize toxicity; the novel modifications of the siRNAs of the present invention can be beneficially applied to double stranded RNA sequences useful in preventing or attenuating target gene expression, in particular the target genes discussed herein.

Details of a non-limited example of target genes per indication are presented in Tables A1-A4, hereinbelow.

TABLE A1

Target genes for treatment of glaucoma

| Gene | Full name and Human Gene ID/SEQ ID NO. for mRNA polynucleotide |
|---|---|
| CASP2 | caspase 2, apoptosis-related cysteine peptidase<br>gi\|39995058\|ref\|NM_032982.2 (SEQ ID NO: 1)<br>gi\|39995060\|ref\|NM_032983.2 (SEQ ID NO: 2) |
| RTP801 | Homo sapiens DNA-damage-inducible transcript 4 (DDIT4), mRNA<br>gi\|56676369\|ref\|NM_019058.2 (SEQ ID NO: 3) |
| ASPP1 | protein phosphatase 1, regulatory (inhibitor) subunit 13B (PPP1R13B)<br>gi\|121114286\|ref\|NM_015316.2 (SEQ ID NO: 4) |
| p53 | tumor protein p53 gi:120407067, NM_000546.2 (SEQ ID NO: 5) |
| TP53BP2 | tumor protein p53 binding protein, 2<br>gi\|112799848\|ref\|NM_001031685.2 (SEQ ID NO: 6)<br>gi\|112799845\|ref\|NM_005426.2 (SEQ ID NO: 7) |
| LRDD | leucine-rich repeats and death domain containing<br>variant 2 gi\|61742781\|ref\|NM_018494.3 (SEQ ID NO: 8) |

TABLE A1-continued

Target genes for treatment of glaucoma

| Gene | Full name and Human Gene ID/SEQ ID NO. for mRNA polynucleotide |
|---|---|
| | variant 1 gi|61742783|ref|NM_145886.2 (SEQ ID NO: 9) |
| | variant 3 gi|61742785|ref|NM_145887.2 (SEQ ID NO: 10) |
| CYBA | cytochrome b-245, alpha polypeptide<br>gi|68509913|ref|NM_000101.2 (SEQ ID NO: 11) |
| BNIP3 | BCL2/adenovirus E1B 19 kDa interacting protein 3<br>gi|7669480|ref|NM_004052.2 (SEQ ID NO: 12) |
| RAC1 | ras-related C3 botulinum toxin substrate 1 (rho family, small GTP binding protein) (gi|38505164|ref|NM_198829.1) (SEQ ID NO: 13) |
| RTP801L | *Homo sapiens* DNA-damage-inducible transcript 4-like (DDIT4L), mRNA gi|34222182|ref|NM_145244.2 (SEQ ID NO: 14) |
| SPP1 | secreted phosphoprotein 1<br>variant 1 gi|91206461|ref|NM_001040058.1 (SEQ ID NO: 15)<br>variant 2 gi|38146097|ref|NM_000582.2 (SEQ ID NO: 16)<br>variant 3 gi|91598938|ref|NM_001040060.1 (SEQ ID NO: 17) |
| SOX9 | *Homo sapiens* SRY (sex determining region Y)-box 9 (campomelic dysplasia, autosomal sex-reversal) (SOX9), mRNA<br>gi|37704387|ref|NM_000346.2 (SEQ ID NO: 18) |
| ACHE | *Homo sapiens* acetylcholinesterase (Yt blood group) (ACHE), variant E4-E6, mRNA gi|88999567|ref|NM_000665.3 (SEQ ID NO: 19)<br>variant E4-E5, mRNA gi|88999566|ref|NM_015831.2 (SEQ ID NO: 20) |
| ADRB1 | *Homo sapiens* adrenergic, beta-1-, receptor (ADRB1), mRNA<br>gi|110349783|ref|NM_000684.2 (SEQ ID NO: 21) |
| HTRA2 | Htra serine peptidase 2<br>v 1 gi:73747817, NM_013247 (SEQ ID NO: 22)<br>v 2 gi:73747818, NM_145074 (SEQ ID NO: 23) |
| KEAP1 | Kelch-like ECH-associated protein 1<br>v 1 gi:45269144 NM_203500 (SEQ ID NO: 24)<br>v 2 gi:45269143 NM_012289 (SEQ ID NO: 25) |
| SHC1-SHC | Src homology 2 domain containing transforming prot. 1<br>v 1 gi: 194239661 NM_183001 (SEQ ID NO: 26)<br>v 2 gi: 194239660 NM_003029 (SEQ ID NO: 27) |
| CAPNS1 | *Homo sapiens* calpain, small subunit 1 (CAPNS1),<br>variant 1, mRNA gi|51599152|ref|NM_001749.2 (SEQ ID NO: 28)<br>variant 2, mRNA gi|51599150|ref|NM_001003962.1 (SEQ ID NO: 29) |
| PARP1 | *Homo sapiens* poly (ADP-ribose) polymerase 1 (PARP1), mRNA<br>gi|156523967|ref|NM_001618.3 (SEQ ID NO: 30) |
| AIF (AIFM1) | *Homo sapiens* apoptosis-inducing factor, mitochondrion-associated, 1<br>variant 4, mRNA gi|195927003|ref|NM_001130846.1 (SEQ ID NO: 31)<br>variant 5, mRNA gi|195927005|ref|NM_001130847.1 (SEQ ID NO: 32) |
| NOS1 | *Homo sapiens* nitric oxide synthase 1 (neuronal) (NOS1), mRNA<br>gi|194239671|ref|NM_000620.2 (SEQ ID NO: 33) |
| NOS2A | *Homo sapiens* nitric oxide synthase 2, inducible (NOS2), mRNA<br>gi|206597519|ref|NM_000625.4 (SEQ ID NO: 34) |
| XIAP | *Homo sapiens* X-linked inhibitor of apoptosis (XIAP), mRNA<br>gi|32528298|ref|NM_001167.2| (SEQ ID NO: 35) |

TABLE A2

Target genes for treatment of dry eye

| Gene | Full name and Human Gene ID |
|---|---|
| FAS | CD95, TNF receptor superfamily, member 6<br>v 1. gi|23510419|ref|NM_000043.3| (SEQ ID NO: 36)<br>v 3. gi|23510422|ref|NM_152872.1| (SEQ ID NO: 37)<br>v 2. gi|23510420|ref|NM_152871.1| (SEQ ID NO: 38)<br>v 4. gi|23510424|ref|NM_152873.1| (SEQ ID NO: 39)<br>v 8. gi|23510426|ref|NM_152874.1| (SEQ ID NO: 40)<br>v 5. gi|23510428|ref|NM_152875.1| (SEQ ID NO: 41)<br>v 7. gi|23510433|ref|NM_152877.1| (SEQ ID NO: 42)<br>v 6. gi|23510430|ref|NM_152876.1| (SEQ ID NO: 43) |
| FAS ligand | TNF superfamily, member 6 (FASL)<br>gi|4557328|ref|NM_000639.1| (SEQ ID NO: 44) |
| p53 | tumor protein p53<br>gi8400737, NM_000546.2 (SEQ ID NO: 5) |
| LRDD | leucine-rich repeats and death domain containing<br>gi|61742781|ref|NM_018494.3 (SEQ ID NO: 8)<br>gi|61742783|ref|NM_145886.2 (SEQ ID NO: 9)<br>gi|61742785|ref|NM_145887.2 (SEQ ID NO: 10) |
| PARP1 | *Homo sapiens* poly (ADP-ribose) polymerase 1 (PARP1), mRNA<br>gi|156523967|ref|NM_001618.3 (SEQ ID NO: 30) |
| AIF | *Homo sapiens* apoptosis-inducing factor, mitochondrion-associated, 1 |

TABLE A2-continued

Target genes for treatment of dry eye

| Gene | Full name and Human Gene ID |
|---|---|
| (AIFM1) | variant 4, mRNA gi|195927003|ref|NM_001130846.1 (SEQ ID NO: 31) |
| | variant 5, mRNA gi|195927005|ref|NM_001130847.1 (SEQ ID NO: 32) |
| NOS1 | *Homo sapiens* nitric oxide synthase 1 (neuronal) (NOS1), mRNA |
| | gi|194239671|ref|NM_000620.2 (SEQ ID NO: 33) |
| NOS2A | *Homo sapiens* nitric oxide synthase 2, inducible (NOS2), mRNA |
| | gi|206597519|ref|NM_000625.4 (SEQ ID NO: 34) |
| XIAP | *Homo sapiens* X-linked inhibitor of apoptosis (XIAP), mRNA |
| | gi|32528298|ref|NM_001167.2| (SEQ ID NO: 35) |
| SHC1- | Src homology 2 domain containing transforming prot. 1 |
| SHC | v 1 gi: 194239661 NM_183001 (SEQ ID NO: 26) |
| | v 2 gi: 194239660 NM_003029 (SEQ ID NO: 27) |

TABLE A3

Target genes for treatment of DR, DME, AMD

| Gene | Full name and Human Gene ID |
|---|---|
| LGALS3 | lectin galactoside-binding soluble 3 |
| | v1 gi: 115430222 NM_002306 (SEQ ID NO: 45) |
| | v2 gi: 115430224 NR_003225 (SEQ ID NO: 46) |
| SLC2A1 | solute carrier family 2 (facilitated glucose transporter), member 1 |
| | gi|166795298|ref|NM_006516.1 (SEQ ID NO: 49) |
| SLC2A2 | solute carrier family 2 (facilitated glucose transporter), member 2 |
| | gi|4557850|ref|NM_000340.1 (SEQ ID NO: 50) |
| SLC2A3 | *Homo sapiens* solute carrier family 2 (facilitated glucose transporter), |
| | member 3 (GLUT5) gi|221136810|ref|NM_006931.1 (SEQ ID NO: 51) |
| SLC5A1 | solute carrier family 5 (sodium/glucose cotransporter), member 1 |
| | gi|208973247|ref|NM_000343.2 (SEQ ID NO: 52) |
| SORD | sorbitol dehydrogenase mRNA |
| | gi|156627570|ref|NM_003104.3 (SEQ ID NO: 53) |
| CTSD | *Homo sapiens* cathepsin D (CTSD) |
| | gi|23110949|ref|NM_001909.3 (SEQ ID NO: 47) |
| CASP2 | caspase 2, apoptosis-related cysteine peptidase |
| | gi|39995058|ref|NM_032982.2 (SEQ ID NO: 1) |
| | gi|39995060|ref|NM_032983.2 (SEQ ID NO: 2) |
| RTP801 | *Homo sapiens* DNA-damage-inducible transcript 4 (DDIT4), mRNA |
| | gi|56676369|ref|NM_019058.2 (SEQ ID NO: 3) |
| p53 | tumor protein p53 gi8400737, NM_000546.2 (SEQ ID NO: 5) |
| TP53BP2 | tumor protein p53 binding protein, 2 |
| | gi|112799848|ref|NM_001031685.2 (SEQ ID NO: 6) |
| | gi|112799845|ref|NM_005426.2 (SEQ ID NO: 7) |
| LRDD | leucine-rich repeats and death domain containing |
| | gi|61742781|ref|NM_018494.3 (SEQ ID NO: 8) |
| | gi|61742783|ref|NM_145886.2 (SEQ ID NO: 9) |
| | gi|61742785|ref|NM_145887.2 (SEQ ID NO: 10) |
| BNIP3 | BCL2/adenovirus E1B 19 kDa interacting protein 3 |
| | gi|7669480|ref|NM_004052.2 (SEQ ID NO: 12) |
| RAC1 | ras-related C3 botulinum toxin substrate 1 (rho family, small GTP |
| | binding protein) (gi|38505164|ref|NM_198829.1) (SEQ ID NO: 13) |
| AKR1B1 | aldo-keto reductase family 1, member B1 (aldose reductase) |
| | gi|24497579|ref|NM_001628.2 (SEQ ID NO: 48) |
| KEAP1 | Kelch-like ECH-associated protein 1 |
| | v 1 gi:45269144 NM_203500 (SEQ ID NO: 24) |
| | v 2 gi:45269143 NM_012289 (SEQ ID NO: 25) |
| PARP1 | *Homo sapiens* poly (ADP-ribose) polymerase 1 (PARP1), mRNA |
| | gi|156523967|ref|NM_001618.3 (SEQ ID NO: 30) |
| AIF | *Homo sapiens* apoptosis-inducing factor, mitochondrion-associated, 1 |
| (AIFM1) | variant 4, mRNA gi|195927003|ref|NM_001130846.1 (SEQ ID NO: 31) |
| | variant 5, mRNA gi|195927005|ref|NM_001130847.1 (SEQ ID NO: 32) |
| NOS1 | *Homo sapiens* nitric oxide synthase 1 (neuronal) (NOS1), mRNA |
| | gi|194239671|ref|NM_000620.2 (SEQ ID NO: 33) |
| NOS2A | *Homo sapiens* nitric oxide synthase 2, inducible (NOS2), mRNA |
| | gi|206597519|ref|NM_000625.4 (SEQ ID NO: 34) |
| XIAP | *Homo sapiens* X-linked inhibitor of apoptosis (XIAP), mRNA |
| | gi|32528298|ref|NM_001167.21 (SEQ ID NO: 35) |
| SHC1- | Src homology 2 domain containing transforming prot. 1 |
| SHC | v 1 gi: 194239661 NM_183001 (SEQ ID NO: 26) |
| | v 2 gi: 194239660 NM_003029 (SEQ ID NO: 27) |

TABLE A4

Examples of target genes for treatment of retinitis pigmentosa (RP)

| Gene | Full name and Human Gene ID |
|---|---|
| CASP1 | *Homo sapiens* caspase 1, apoptosis-related cysteine peptidase (interleukin 1, beta, convertase) (CASP1), mRNA<br>variant epsilon, gi\|73622117\|ref\|NM_033295.2 (SEQ ID NO: 54)<br>variant alpha, gi\|73622114\|ref\|NM_033292.2 (SEQ ID NO: 55) |
| CASP3 | *Homo sapiens* caspase 3, apoptosis-related cysteine peptidase (CASP3), mRNA<br>variant alpha, gi\|73622121\|ref\|NM_004346.3 (SEQ ID NO: 56)<br>variant beta, gi\|73622122\|ref\|NM_032991.2 (SEQ ID NO: 57) |
| CASP12 | *Homo sapiens* caspase 12<br>variant zeta (CASP12) mRNA, complete sequence; alternatively spliced gi\|20069120\|gb\|AF486846.1\| (SEQ ID NO: 58) |
| RTP801 | *Homo sapiens* DNA-damage-inducible transcript 4 (DDIT4), mRNA gi\|56676369\|ref\|NM_019058.2 (SEQ ID NO: 3) |
| RTP801L | *Homo sapiens* DNA-damage-inducible transcript 4-like (DDIT4L), mRNA gi\|34222182\|ref\|NM_145244.2 (SEQ ID NO: 14) |
| CAPNS1 | *Homo sapiens* calpain, small subunit 1 (CAPNS1),<br>variant 1, mRNA gi\|51599152\|ref\|NM_001749.2 (SEQ ID NO: 28)<br>variant 2, mRNA gi\|51599150\|ref\|NM_001003962.1 (SEQ ID NO: 29) |
| PARP1 | *Homo sapiens* poly (ADP-ribose) polymerase 1 (PARP1), mRNA gi\|156523967\|ref\|NM_001618.3 (SEQ ID NO: 30) |
| AIF (AIFM1) | *Homo sapiens* apoptosis-inducing factor, mitochondrion-associated, 1<br>variant 4, mRNA gi\|195927003\|ref\|NM_001130846.1 (SEQ ID NO: 31)<br>variant 5, mRNA gi\|195927005\|ref\|NM_001130847.1 (SEQ ID NO: 32) |
| NOS1 | *Homo sapiens* nitric oxide synthase 1 (neuronal) (NOS1), mRNA gi\|194239671\|ref\|NM_000620.2 (SEQ ID NO: 33) |
| NOS2A | *Homo sapiens* nitric oxide synthase 2, inducible (NOS2), mRNA gi\|206597519\|ref\|NM_000625.4 (SEQ ID NO: 34) |
| XIAP | *Homo sapiens* X-linked inhibitor of apoptosis (XIAP), mRNA gi\|32528298\|ref\|NM_001167.21 (SEQ ID NO: 35) |
| SHC1-SHC | Src homology 2 domain containing transforming prot. 1<br>v 1 gi: 194239661 NM_183001 (SEQ ID NO: 26)<br>v 2 gi: 194239660 NM_003029 (SEQ ID NO: 27) |

"Variant" or "v" refer to transcript variant.

Tables A1-A4 provide the gi (GeneInfo identifier) and accession numbers for an example of polynucleotide sequences of human mRNA to which the oligonucleotide inhibitors of the present invention are directed. ("v" refers to transcript variant)

Inhibition of the genes in Tables A1, A2, A3 and A4 is useful in treating, inter alia, glaucoma, dry eye, diabetic retinopathy (DR), diabetic macular edema (DME), age related macular degeneration (AMD) and retinitis pigmentosa (RP), respectively.

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound which is capable of reducing the expression of a gene or the activity of the product of such gene to an extent sufficient to achieve a desired biological or physiological effect. The term "inhibitor" as used herein refers to one or more of an oligonucleotide inhibitor, including siRNA, antisense, shRNA, miRNA and ribozymes. Inhibition may also be referred to as attenuation of expression of mRNA, down-regulation, or for RNA interference (RNAi) silencing. The inhibitors disclosed herein are chemically modified siRNA compounds which incorporate modifications such as changes to the sugar moiety and/or the base moiety and/or the linkages between nucleotides in the oligonucleotide structure.

The term "inhibit" or "attenuate" as used herein refers to reducing the expression of a gene, a variant or product thereof or the activity of the product of such gene to an extent sufficient to achieve a desired biological or physiological effect. Inhibition may be complete or partial. For example "inhibition" of CASP2 gene means inhibition of the gene expression (transcription or translation) or polypeptide activity of one or more of the variants disclosed in any Table A1 or A3 or an SNP (single nucleotide polymorphism) or other variants thereof.

"Ocular tissue" referees to any tissue associated with structure of the eye and is intended to include, in a non-limiting manner, the sclera, the cornea, the choroid, the retina, the lacrimal gland, and the optic nerve.

"Ocular cell" refers to any cell associated with structures of the eye and lacrimal apparatus and is intended to include, in a non-limiting manner, retinal ganglion cell, a retinal pigment epithelial cell, a corneal cell, conjunctiva, anterior chamber, iris, ciliary process, retina, choroid and choroidal cells, trabecular meshwork, and the like. For example the trabecular meshwork includes the inner uveal meshwork, the corneoscleral meshwork and the juxtacanalicular tissue. The lacrimal gland includes the lacrimal gland per se, the inferior and superior lacrimal puncta, the inferior and superior lacrimal canal, the lacrimal sac and the like.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application mRNA sequences are set forth as representing the corresponding genes. The terms "mRNA polynucleotide sequence" and mRNA are used interchangeably.

"Oligonucleotide", "oligoribonucleotide or "oligomer" refers to a deoxyribonucleotide or ribonucleotide sequence from about 2 to about 50 nucleotides. Each DNA or RNA nucleotide of the sequence may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides and combinations thereof.

The present invention provides methods and compositions for inhibiting expression of a target gene in vivo. In general, the method includes topically administering oligoribonucleotides, in particular small interfering RNAs (i.e., siRNAs) or a nucleic acid material that can produce siRNA in a cell, to target an mRNA of the genes set forth in Tables A1-A4; in an amount sufficient to down-regulate expression of a target gene by an RNA interference mechanism. In particular, the method can be used to inhibit expression of the gene for treatment of a subject suffering from an eye disorder or disease related to expression of that gene in ocular tissue or cell. In accordance with the present invention, the siRNA molecules or inhibitors of the target gene are used as drugs to treat various ocular pathologies.

"Nucleotide" is meant to encompass deoxyribonucleotides and ribonucleotides, which may be natural or synthetic, and or modified or unmodified. Modifications include changes and substitutions to the sugar moiety, the base moiety and/or the internucleotide linkages.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

All analogs of, or modifications to, a nucleotide/oligonucleotide may be employed with the present invention, provided that said analog or modification does not substantially adversely affect the stability and function of the nucleotide/oligonucleotide. Acceptable modifications include modifications of the sugar moiety, modifications of the base moiety, modifications in the internucleotide linkages and combinations thereof.

What is sometimes referred to in the present invention as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide.

The term "capping moiety" as used herein includes abasic ribose moiety, abasic deoxyribose moiety, modifications abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties. A 2'-O-methyl sugar modified ribonucleotide is also referred to as 2'-OMe sugar modified or 2'-OMe modified ribonucleotide Certain preferred capping moieties are abasic ribose or abasic deoxyribose moieties; inverted abasic ribose or abasic deoxyribose moieties; C6-amino-Pi; a mirror nucleotide including L-DNA and L-RNA.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; bridged nucleic acids including LNA and ethylene bridged nucleic acids.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

In the context of the present invention, a "mirror" nucleotide (also referred to as a spieglemer), is a nucleotide analog with reverse chirality to the naturally occurring or commonly employed nucleotide, i.e., a mirror image of the naturally occurring or commonly employed nucleotide. The mirror nucleotide is a ribonucleotide (L-RNA) or a deoxyribonucleotide (L-DNA) and may further comprise at least one sugar or base modification and/or a backbone modification, such as a phosphorothioate or phosphonate moiety. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror dT) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU)

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Bridged nucleic acids include LNA (2'-O,4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

In some embodiments of the present invention a preferred unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

According to one aspect the present invention provides inhibitory oligonucleotide compounds comprising unmodified and modified nucleotides. The compound comprises at least one modified nucleotide selected from the group consisting of a sugar modification, a base modification and an internucleotide linkage modification and may contain DNA, and modified nucleotides such as LNA (locked nucleic acid) including ENA (ethylene-bridged nucleic acid; PNA (peptide nucleic acid); arabinoside; PACE (phosphonoacetate and derivatives thereof), mirror nucleotide, or nucleotides with a 6 carbon sugar.

In one embodiment the compound comprises a 2' modification on the sugar moiety of at least one ribonucleotide ("2' sugar modification"). In certain embodiments the compound comprises 2'O-alkyl or 2'-fluoro or 2'O-allyl or any other 2' sugar modification, optionally on alternate positions.

Other stabilizing modifications are also possible (e.g. modified nucleotides added to a 3' or 5' terminus of an oligomer). In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE modified internucleotide linkage or any other type of modification.

Other modifications include additions to the 5' and/or 3' termini of the oligonucleotides. Such terminal modifications may be lipids, peptides, sugars or other molecules.

Possible modifications to the sugar residue are manifold and include 2'-O alkyl, locked nucleic acid (LNA), glycol nucleic acid (GNA), threose nucleic acid (TNA), arabinoside; altritol (ANA) and other 6-membered sugars including morpholinos, and cyclohexinyls.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1): 439-447) and in International Patent Publication No. WO 2004/083430. Six-membered ring nucleotide analogs are disclosed in Allart, et al (Nucleosides & Nucleotides, 1998, 17:1523-1526; and Perez-Perez, et al., 1996, Bioorg. and Medicinal Chem Letters 6:1457-1460) Oligonucleotides comprising 6-membered ring nucleotide analogs including hexitol and altritol nucleotide monomers are disclosed in International patent application publication No. WO 2006/047842.

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, and phosphonoacetate derivatives. Certain structures include siRNA compounds having one or a plurality of 2'-5' internucleotide linkages (bridges or backbone).

The present invention also relates to compounds which down-regulate expression of various genes, particularly to novel small interfering RNA (siRNA) compounds, and to the use of these novel siRNAs in the treatment of various ocular diseases and medical conditions of the eye.

For each gene there is a separate list of 19-mer oligomer sequences, which are prioritized based on their score in the proprietary algorithm as the best sequences for targeting the human gene expression. 21- or 23-mer siRNA sequences can be generated by 5' and/or 3' extension of the 19-mer sequences disclosed herein. Such extension is preferably complementary to the corresponding mRNA sequence. Certain 23-mer oligomers were devised by this method where the order of the prioritization is the order of the corresponding 19-mer. Tables B1-B36 provide human sense and corresponding antisense oligonucleotides useful in preparing siRNA. The abbreviations for cross species are: Ms: Mouse, Rb: Rabbit, Chmp: chimpanzee, Mnk: Monkey, Chn: chinchilla, GP: guinea-pig.

Ocular Diseases

Topical delivery of therapeutic oligonucleotide compounds is useful in the treatment of a broad spectrum of eye diseases and disorders. Certain of the compounds of the invention are useful in treating patients suffering from diseases and disorders in which neuroprotection of the optic nerve would be of benefit, for example in:
1. open angle primary/secondary glaucoma
2. multiple sclerosis (optic neuritis)
3. central or brunch retinal vein occlusion
4. ischemic optic neuropathy (in status epilepticus, HIV-1 infection)
5. optic nerve injury
6. tumors extending into the suprasellar region (above the sella turcica)
7. juxta chiasmal tumors (the visual loss associated with compression of the optic chiasm by pituitary tumors may be transient or permanent, possibly related to the extent of irreversible retrograde degeneration to the retinal ganglion cells.
8. Retinoblastoma Primary Open-Angle Glaucoma The majority of the cases of glaucoma are the form known as primary-open-angle glaucoma POAG, also called chronic open-angle glaucoma). POAG results from a build up of aqueous humor fluid within the anterior chamber of the eye resulting in intraocular pressure (IOP). Elevated IOP, which can be measured by a "tonometry" test, results from fluid entering the eye and not enough fluid exiting the eye. Normally, fluid enters the eye by seeping out of the blood vessels in the ciliary body. This fluid eventually makes its way past the crystalline lens, through the pupil (the central opening in the iris), and into the irido-corneal angle, the anatomical angle formed where the iris and the cornea come together. Then the fluid passes through the trabecular meshwork in the angle and leaves the eye via the canal of Schlemm.

If excess fluid enters the eye, or if the trabecular meshwork "drain" gets clogged up (for instance, with debris or cells) so that not enough fluid is leaving the eye, the pressure builds up in what is known as "open angle glaucoma." Open angle glaucoma also can be caused when the posterior portion of the iris adheres to the anterior surface of the lens creating a "pupillary block", and preventing intraocular fluid from passing through the pupil into the anterior chamber.

If the angle between the iris and the cornea is too narrow or is even closed, then the fluid backs up, causing increased pressure in what is known as "closed angle glaucoma."

Untreated glaucoma eventually leads to optic atrophy and blindness.

Normal Tension Glaucoma

Intraocular eye pressure is normal (between 12-22 mmHg) in about 25-30% glaucoma cases in the US, a condition known as normal-tension glaucoma. (In Japan, the rates may be as high as 70%.) Other factors are present that cause optic nerve damage but do not affect IOP.

Closed-Angle Glaucoma

Closed-angle glaucoma (also called angle-closure glaucoma) is responsible for 15% of all glaucoma cases. It is less common than POAG in the U.S., but it constitutes about half of the world's glaucoma cases because of its higher prevalence among Asians. The iris is pushed against the lens, sometimes sticking to it, closing off the drainage angle. This can occur very suddenly, resulting in an immediate rise in pressure. It often occurs in genetically susceptible people when the pupil shrinks suddenly. Closed-angle glaucoma can also be chronic and gradual, a less common condition.

Congenital Glaucoma

Congenital glaucoma, in which the eye's drainage canals fail to develop correctly, is present from birth. It is very rare, occurring in about 1 in 10,000 newborns. This may be an inherited condition and often can be corrected with microsurgery.

In one aspect the present invention provides a method of attenuating expression of a target ocular mRNA in the eye of a subject suffering from glaucoma, comprising topically (non-invasively) administering to the surface of the eye of the subject an effective amount of at least one chemically modified siRNA and a pharmaceutically acceptable carrier. In certain embodiments the at least one ocular target mRNA is a product of a gene selected from a list in Table A1 set forth in SEQ ID NOS:1-35. In certain preferred embodiments the target ocular mRNA is a product of a gene selected from CASP2, ASPP1, TP53BP2, BNIP3, RTP801L, ACHE, ADRB1 and CAPNS1. In a currently preferred embodiment the siRNA is formulated for delivery as eye drops. In various embodiments the target ocular mRNA set forth in SEQ ID NOS:1-2.

In another aspect the present invention provides a method of treating glaucoma in a subject in need of treatment, comprising topically (non-invasively) administering to the surface of the eye of the subject a therapeutically effective amount of at least one chemically modified siRNA which inhibits expression of a target gene in the eye of the subject. In some embodiments the gene is a human gene selected from a list in Table A1, transcribed into mRNA set forth in any one of SEQ ID NOS:1-35. In certain preferred embodiments the gene is selected from CASP2, ASPP1, TP53BP2, BNIP3, RTP801L, ACHE, ADRB1 and CAPNS1. In a currently preferred embodiment the siRNA is formulated for delivery as eye drops. In various embodiments the target ocular mRNA set forth in SEQ ID NOS:1-2.

Optic Neuritis

Optic neuritis is an inflammation of the optic nerve that may affect the part of the nerve and disc within the eyeball (papillitis) or the portion behind the eyeball (retrobulbar optic neuritis). Optic neuritis may be caused by any of the following: demyelinating diseases such as multiple sclerosis or post infectious encephalomyelitis; systemic viral or bacterial infections including complications of inflammatory diseases (e.g., sinusitis, meningitis, tuberculosis, syphilis, chorioretinitis, orbital inflammation); nutritional and metabolic diseases (e.g., diabetes, pernicious anemia, hyperthyroidism); Leber's Hereditary Optic Neuropathy, a rare form of inherited optic neuropathy which mainly affects young men; toxins (tobacco, methanol, quinine, arsenic, salicylates, lead); and trauma.

Optic Atrophy

Optic atrophy is a hereditary or acquired loss of vision disorder that results from the degeneration of the optic nerve and optic tract nerve fibers. It may be acquired via occlusions of the central retinal vein or artery, arteriosclerotic changes, may be secondary to degenerative retinal disease, may be a result of pressure against the optic nerve, or may be related to metabolic diseases (e.g., diabetes), trauma, glaucoma, or toxicity (to alcohol, tobacco, or other poisons). Degeneration and atrophy of optic nerve fibers is irreversible, although intravenous steroid injections have been seen to slow down the process in some cases.

Papilledema

A swelling of the optic disc (papilla), most commonly due to an increase in intracranial pressure (tumor induced), malignant hypertension, or thrombosis of the central retinal vein. The condition usually is bilateral, the nerve head is very elevated and swollen, and pupil response typically is normal. Vision is not affected initially and there is no pain upon eye movement. Secondary optic nerve atrophy and permanent vision loss can occur if the primary cause of the papilledema is left untreated.

Ischemic Optic Neuropathy (ION)

A severely blinding disease resulting from loss of the arterial blood supply to the optic nerve (usually in one eye), as a result of occlusive disorders of the nutrient arteries. Optic neuropathy can be anterior, which causes a pale edema of the optic disc, or posterior, in which the optic disc is not swollen and the abnormality occurs between the eyeball and the optic chiasm. Ischemic anterior optic neuropathy usually causes a loss of vision that may be sudden or occur over several days. Ischemic posterior optic neuropathy is uncommon, and the diagnosis depends largely upon exclusion of other causes, chiefly stroke and brain tumor.

Other diseases and conditions include dry eye, diabetic retinopathy, diabetic macular edema and retinitis pigmentosa.

Dry Eye

Dry eye, also known as keratoconjunctivitis sicca or keratitis sicca, is a common problem usually resulting from a decrease in the production of tear film that lubricates the eyes. Most patients with dry eye experience discomfort, and no vision loss; although in severe cases, the cornea may become damaged or infected.

Dry eye is a multifactorial disease of the tears and ocular surface that results in symptoms of discomfort, visual disturbance, and tear film instability with potential damage to the ocular surface. It is accompanied by increased osmolarity of the tear film and inflammation of the ocular surface.

The lacrimal gland is a multilobular tissue composed of acinar, ductal, and myoepithelial cells. The acinar cells account for 80% of the cells present in the lacrimal gland and are the site for synthesis, storage, and secretion of proteins. Several of these proteins have antibacterial (lysozyme, lactoferrin) or growth factor (epidermal growth factor, transforming growth factor α, keratocyte growth factor) properties that are crucial to the health of the ocular surface. The primary function of the ductal cells is to modify the primary fluid secreted by the acinar cells and to secrete water and electrolytes. The myoepithelial cells contain multiple processes, which surround the basal area of the acinar and ductal cells, and are believed to contract and force fluid out of the ducts and onto the ocular surface.

Mechanisms of Lacrimal Gland Dysfunction

Apoptosis, hormonal imbalance, production of autoantibodies, alterations in signaling molecules, neural dysfunction, and increased levels of proinflammatory cytokines have been proposed as possible mediators of lacrimal gland insufficiency. One of the primary symptoms of Sjögrens Syndrome is dry eye. Apoptosis of the acinar and ductal epithelial cells of the lacrimal glands has been proposed as a possible mechanism responsible for the impairment of secretory function (Manganelli and Fietta, Semin Arthritis Rheum. 2003. 33(1): 49-65). Without wishing to be bound by theory, apoptotic epithelial cell death may be due to activation of several apoptotic pathways involving Fas (Apo-1/CD95), FasL (FasL/CD95L), Bax, caspases, perform, and granzyme B. Cytotoxic T cells through the release of proteases, such as perform and granzyme B, or the interaction of FasL expressed by T cells with Fas on epithelial cells, can lead to apoptosis of the acinar cells.

The current treatment for dry eye is mainly local and symptomatic such as: tear supplementation with lubricants; tear retention with therapies such as punctal occlusion, moisture chamber spectacles or contact lenses; tear stimulation for example by secretagogues; biological tear substitutes; anti-inflammatory therapy (Cyclosporine, Corticosteroids, Tetracyclines); and dietary essential fatty acids.

In one aspect the present invention provides a method of attenuating expression of a target ocular mRNA in the eye of a subject suffering from dry-eye, comprising topically (non-invasively) administering to the surface of the eye of the subject an effective amount of at least one chemically modified siRNA and a pharmaceutically acceptable carrier. In some embodiments the target ocular mRNA is product of a human gene selected Table A2 set forth in SEQ ID NOS: 5, 8-10, 26-27, 30-44. In some embodiments the target ocular mRNA is selected from FAS, FAS ligand (FASL), p53, LRDD, PARP1, AIF (apoptosis inducing factor), NOS1, NOS2A, XIAP and SHC1-SHC. In certain preferred embodiments the target ocular mRNA is set forth in any one of SEQ ID NOS:36-44. In a currently preferred embodiment the siRNA is formulated for delivery as eye drops. In various embodiments the subject is suffering from Sjögrens syndrome. In some embodiments the siRNA sense and antisense strands are selected from sequences in Tables 16-17, set forth in SEQ ID NOS: 13225-15224.

In another aspect the present invention provides a method of treating dry-eye in a subject in need of treatment, comprising topically (non-invasively) administering to the surface of the eye of the subject a therapeutically effective amount of at least one chemically modified siRNA which inhibits expression of a target gene in the eye of the subject. In some embodiments the target gene is a human gene selected from Table A2, whose mRNA is set forth in any one of SEQ ID NOS: 5, 8-10, 26-27, or 30-44. In some embodiments the target gene is selected from FAS, FAS ligand (FASL), p53, LRDD, PARP1, AIF (apoptosis inducing factor), NOS1, NOS2A, XIAP and SHC1-SHC. In certain preferred embodiments the target gene mRNA is set forth in any one of SEQ ID NOS:36-44. In a currently preferred embodiment the siRNA is formulated for delivery as eye drops. In various embodiments the subject is suffering from Sjögrens syndrome. In some embodiments the siRNA sense and antisense strands are selected from sequences in Tables 16-17, set forth in SEQ ID NOS: 13225-15224.

Retinitis Pigmentosa

Retinitis pigmentosa (RP) represents a group of inherited disorders characterized by progressive peripheral vision loss and nyctalopia that can lead to central vision loss. There is currently no cure for retinitis pigmentosa, although the progression of the disease can be attenuated by dietary vitamin A supplementation.

Apoptosis in rod and cone photoreceptor cells is a critical process of retinal degeneration in RP and represent a major cause of adult blindness.

In one aspect the present invention provides a method of attenuating expression of a target ocular mRNA in the eye of a subject suffering from Retinitis pigmentosa (RP), comprising topically (non-invasively) administering to the surface of the eye of the subject an effective amount of at least one chemically modified siRNA and a pharmaceutically acceptable carrier. In some embodiments the target ocular mRNA is product of a gene selected from a gene listed in Table A4, the gene transcribed into mRNA set forth in any one of SEQ ID NOS: 3, 14, 26-35, 54-57. In some embodiments the target ocular mRNA is product of a gene selected from the group consisting of CASP1, CASP3, CASP12, RTP801, RTP801L, Calpain 51, PARP1, AIF, NOS1, NOS2, XIAP and SHC1-SHC. In a currently preferred embodiment the siRNA is formulated for delivery as eye drops. In certain preferred embodiments the siRNA targets mRNA set forth in SEQ ID NOS:56-57. In some embodiments the siRNA sense and antisense strands are selected from sequences in Table 11, set forth in SEQ ID NOS: 9517-10516.

In another aspect the present invention provides a method of treating Retinitis pigmentosa (RP) in a subject in need of treatment, comprising topically (non-invasively) administering to the surface of the eye of the subject a therapeutically effective amount of at least one chemically modified siRNA which inhibits expression of a target gene in the eye of the subject. In some embodiments the target gene is a human gene listed in Table A4, transcribed into mRNA set forth in any one of SEQ ID NOS: 3, 14, 26-35, 54-57. In some embodiments the gene is a human gene selected from selected from the group consisting of CASP1, CASP3, CASP12, RTP801, RTP801L, Calpain 51, PARP1, AIF, NOS1, NOS2, XIAP and SHC1-SHC. In a currently preferred embodiment the siRNA is formulated for delivery as eye drops. In certain preferred embodiments the siRNA targets and inhibits mRNA set forth in SEQ ID NOS:56-57. In some embodiments the siRNA sense and antisense strands are selected from sequences in Table 11, set forth in SEQ ID NOS: 9517-10516.

Diabetic Retinopathy

Diabetic retinopathy is a complication of diabetes and a leading cause of blindness. It occurs when diabetes damages the tiny blood vessels inside the retina. Diabetic retinopathy has four stages:

Mild Nonproliferative Retinopathy: microaneurysms in the retina's blood vessels.

Moderate Nonproliferative Retinopathy. As the disease progresses, some blood vessels that nourish the retina are blocked.

Severe Nonproliferative Retinopathy. Many more blood vessels are blocked, depriving several areas of the retina of a blood supply, which is overcome by the growth of new blood vessels.

Proliferative Retinopathy. The new blood vessels grow along the retina and along the surface of the vitreous gel. When the vessels leak blood, severe vision loss and even blindness can result.

During pregnancy, diabetic retinopathy may be a problem for women with diabetes.

In one aspect the present invention provides a method of attenuating expression of a target ocular mRNA in the eye of a subject suffering from diabetic retinopathy, comprising topically (non-invasively) administering to the surface of the eye of the subject an effective amount of at least one chemically modified siRNA and a pharmaceutically acceptable carrier. In some embodiments the target ocular mRNA is product of a human gene listed in Table A3 having mRNA set forth in any one of SEQ ID NOS:1-2, 3, 5, 6-7, 8-10, 12, 13, 24-25, 26-27, 30-35, 45-53. In a currently preferred embodiment the siRNA is formulated for delivery as eye drops. In certain preferred embodiment the target ocular mRNA set forth in any one of SEQ ID NOS:48-53. In some embodiments the siRNA sense and antisense strands are selected from sequences in Tables 4, 28-32 set forth in SEQ ID NOS: 2669-3648 and 25575-29594.

In another aspect the present invention provides a method of treating diabetic retinopathy in a subject in need of treatment, comprising topically (non-invasively) administering to the surface eye of the subject a therapeutically effective amount of at least one chemically modified siRNA which inhibits expression of a target gene in the eye of the subject. In some embodiments the target gene is a human gene listed in Table A3, having mRNA set forth in any one SEQ ID NOS: 1-2, 3, 5, 6-7, 8-10, 12, 13, 24-25, 26-27, 30-35, 45-53. In a currently preferred embodiment the siRNA is formulated for delivery as eye drops. In certain preferred embodiment the target ocular mRNA set forth in any one of SEQ ID NOS:48-53. In some embodiments the siRNA sense and antisense strands are selected from sequences in Tables 4, 28-32 set forth in SEQ ID NOS: 2669-3648 and 25575-29594.

Without wishing to be bound to theory, blood vessels damaged from diabetic retinopathy can cause vision loss in two ways: Fragile, abnormal blood vessels can develop and leak blood into the center of the eye, blurring vision. This is proliferative retinopathy and is the fourth and most advanced stage of the disease. Fluid can leak into the center of the macula, resulting in blurred vision. This condition is called macular edema. It can occur at any stage of diabetic retinopathy, although it is more likely to occur as the disease progresses and is known as diabetic macular edema (DME).

Age Related Macular Degeneration (AMD)

The most common cause of decreased best-corrected, vision in individuals over 65 years of age in the United States is the retinal disorder known as age-related macular degeneration (AMD). The area of the eye affected by AMD is the macula, a small area in the center of the retina, composed primarily of photoreceptor cells. As AMD progresses, the disease is characterized by loss of sharp, central vision. So-called "dry" AMD accounts for about 85%-90% of AMD patients and involves alterations in eye pigment distribution, loss of photoreceptors and diminished retinal function due to overall atrophy of cells. "Wet" AMD involves proliferation of abnormal choroidal vessels leading to clots or scars in the sub-retinal space. Thus, the onset of "wet" AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, Frontiers in Bioscience, e305-314, May 2003).

In one aspect the present invention provides a method of attenuating expression of a target ocular mRNA in the eye of a subject suffering from AMD or DME, comprising topically (non-invasively) administering to the surface of the eye of the subject an effective amount of at least one chemically modified siRNA and a pharmaceutically acceptable carrier. In some embodiments the target ocular mRNA is product of a human gene listed in Table A3, having mRNA set forth in any one of SEQ ID NOS:1-2, 3, 5, 6-7, 8-10, 12, 13, 24-25, 26-27, 30-35, 45-53. In a currently preferred embodiment the siRNA is formulated for delivery as eye drops. In certain preferred embodiment the target ocular mRNA is product of a human CTSD, RTP801 and BNIP3.

In another aspect the present invention provides a method of treating AMD or DME in a subject in need of treatment, comprising topically (non-invasively) administering to the surface of the eye of the subject a therapeutically effective amount of at least one chemically modified siRNA which inhibits expression of a target gene in the eye of the subject. In some embodiments the target gene is a human gene listed in Table A3, having mRNA set forth in any one of SEQ ID NOS:1-2, 3, 5, 6-7, 8-10, 12, 13, 24-25, 26-27, 30-35, 45-53. In a currently preferred embodiment the siRNA is formulated for delivery as eye drops. In certain preferred embodiment the target human gene is a human CTSD, RTP801 and BNIP3.

Additional Ocular Conditions to be Treated by Compounds of the Present Invention Viral and Bacterial Conditions Viral and bacterial conditions relating to ocular tissues can be treated by the compounds of the present invention. Conjunctivitis and other eyelid diseases or conditions can be treated, in particular by administering according to the methods of the present invention oligonucleotides such as siRNAs which target genes which are essential for replication and/or survival of the organisms which cause such conditions.

Vision Loss Associated with Tumors

In another aspect the present invention provides method of treating vision loss associated with a tumor in a subject in need thereof which comprises topically and non-invasively administering to the surface of the eye of the subject a therapeutically effective amount of at least one chemically modified siRNA which inhibits expression of at least one gene associated with the tumor in the subject in an amount effective to treat the vision loss.

Tumors that cause vision loss, according to the present invention, include both malignant neoplasms (cancers) and benign tumors. Tumors include tumors of any ocular tissue or any type of ocular cell, including, but not limited to, Choroidal tumors, Conjunctival tumors, Eyelid tumors, Infiltrative Intraocular tumors, Iris tumors, Metastatic Ocular tumors, Optic Nerve tumors, Orbital tumors and Retinal tumors. More specifically, a non exhaustive list of tumors and cancers which the present invention aims to treat includes Choroidal Tumors such as Choroidal Hemangioma, Choroidal Melanoma, Choroidal Metastasis, Choroidal Nevus, Choroidal Osteoma, Ciliary Body Melanoma and Nevus of Ota; Conjunctival Tumors such as Conjunctival Kaposi's Sarcoma, Epibulbar Dermoid, Lymphoma of the Conjunctiva, Melanoma and PAM with Atypia, Pigmented Conjunctival Tumors, Pingueculum, Pterygium, Squamous Carcinoma and Intraepithelial Neoplasia of the Conjunctiva; Eyelid Tumors such as Basal Cell Carcinoma, Capillary Hemangioma, Hydrocystoma, Nevus at the Eyelid Margin, Seborrheic Keratosis, Malignant Melanoma of the Eyelid, Sebaceous Carcinoma of the Eyelid and Squamous Carcinoma of the Eyelid; Infiltrative Intraocular Tumors such as Chronic Lymphocytic Leukemia, Infiltrative Choroidopathy and Intraocular Lymphoma; Iris Tumors such as Anterior Uveal Metastasis, Iris Cysts, Iris Melanocytoma, Iris Melanoma and Pearl Cyst of the Iris; Metastatic Ocular Tumors such as Metastatic Choroidal Melanoma; Optic Nerve Tumors such as Choroidal Melanoma Affecting the Optic Nerve, Circumpapillary Metastasis with Optic Neuropathy, Optic Nerve Melanocytoma and Optic Nerve Sheath Meningioma; Orbital Tumors such as Adenoid Cystic Carcinoma of the Lacrimal Gland, Cavernous Hemangioma of the Orbit, Lymphangioma of the Orbit, Orbital Mucocele, Orbital Pseudotumor, Orbital Rhabdomyosarcoma, Periocular Hemangioma of Childhood and Sclerosing Orbital Pseudotumor; Retinal Tumors such as Retinal Pigment Epithelial (RPE) Hypertrophy, Retinal Pigment Epithelium (RPE) Tumors, Retinoblastoma and von Hippel Angioma.

Pharmaceutical Compositions

While it may be possible for the oligonucleotide compounds of the present invention to be administered as the raw chemical, it is preferable to administer them as a pharmaceutical composition. Accordingly the present invention provides a pharmaceutical composition comprising one or more of the compounds of the invention; and a pharmaceutically acceptable carrier. This composition may comprise a mixture of two or more different oligonucleotides/siRNAs.

The invention further provides a pharmaceutical composition comprising at least one compound of the invention covalently or non-covalently bound to one or more compounds of the invention in an amount effective to inhibit one or more genes as disclosed above; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to down-regulate expression in of a human gene in an eye of a subject suffering from an eye disease or disorder.

The present invention also provides for a process of preparing a pharmaceutical composition, which comprises:

providing one or more compounds of the invention; and
admixing said compound with a pharmaceutically acceptable carrier.

The pharmaceutically acceptable carrier is preferably selected by one with skill in the art for ophthalmological administration.

In various embodiments the pharmaceutical composition of the invention comprises at least one siRNA compound of the invention, or salt thereof, up to 99% by weight, mixed with a physiologically acceptable ophthalmic carrier medium such as water, sodium chloride, buffer, saline (e.g. phosphate buffered saline (PBS)), mannitol, and the like, and combinations thereof, to form an aqueous, sterile ophthalmic suspension or solution.

The pharmaceutical composition further optionally comprises at least one ophthalmologically acceptable preservative, such as for example benzalkonium chloride. Further, the ophthalmic pharmaceutical composition may include an ophthalmologically acceptable surfactant to assist in dissolving the siRNA.

Ophthalmic pharmaceutical composition of the invention may be prepared by dissolving or admixing one or more of the interfering RNA with an ophthalmologically acceptable carrier, such as for example a physiologically acceptable isotonic aqueous buffer.

In a preferred embodiment, the siRNA compound used in the preparation of an ophthalmological composition is admixed with an ophthalmologically acceptable carrier in a pharmaceutically effective dose. In certain preferred embodiments the ophthalmologically acceptable carrier is PBS.

In some embodiments the pharmaceutical ophthalmic compositions of the invention further comprise additional pharmaceutically active agents or a combination of pharmaceutically active agent, such as non-steroidal anti-inflammatory drugs, corticosteroids, antibiotics, and the like.

Additionally, the invention provides a method of inhibiting the expression of a gene of the present invention by at least 20% as compared to a control comprising contacting an mRNA transcript of the gene of the present invention with one or more of the compounds of the invention. In some embodiments an active siRNA compound inhibits gene expression at a level of at least 20%, 30%, 40%, 50%, 60% or 70% as compared to control. In certain preferred embodiments inhibition is at a level of at least 75%, 80% or 90% as compared to control.

In one embodiment the oligoribonucleotide is inhibiting one or more of the genes of the present invention, whereby the inhibition is selected from the group comprising inhibition of gene function, inhibition of polypeptide and inhibition of mRNA expression.

In one embodiment the compound inhibits a polypeptide, whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridization or microarray hybridization, inter alia).

Combination Therapy

The compounds of the present invention can be administered alone or in combination with another therapeutic agent useful in treating an eye disorder or disease.

In some embodiments the pharmaceutical ophthalmic compositions of the invention further comprise additional pharmaceutically active agents or a combination of pharmaceutically active agent, such as oligonucleotide, e.g. siRNA, non-steroidal anti-inflammatory drug, corticosteroid, antibiotic, and the like.

In one embodiment, the co-administration of two or more therapeutic agents achieves a synergistic effect, i.e., a therapeutic affect that is greater than the sum of the therapeutic effects of the individual components of the combination. In another embodiment, the co-administration of two or more therapeutic agents achieves an additive effect.

The active ingredients that comprise a combination therapy may be administered together via a single dosage form or by separate administration of each active agent. In certain embodiments, the first and second therapeutic agents are administered in a single dosage form. The agents may be formulated into a single solution for topical administration. Alternatively, the first therapeutic agent and the second therapeutic agents may be administered as separate compositions. The first active agent may be administered at the same time as the second active agent or the first active agent may be administered intermittently with the second active agent. The length of time between administration of the first and second therapeutic agent may be adjusted to achieve the desired therapeutic effect. For example, the second therapeutic agent may be administered only a few minutes (e.g., 1, 2, 5, 10, 30, or 60 min) or several hours (e.g., 2, 4, 6, 10, 12, 24, or 36 hr) after administration of the first therapeutic agent. In certain embodiments, it may be advantageous to administer more than one dosage of one of the therapeutic agents between administrations of the second therapeutic agent. For example, the second therapeutic agent may be administered at 2 hours and then again at 10 hours following administration of the first therapeutic agent. Alternatively, it may be advantageous to administer more than one dosage of the first therapeutic agent between administrations of the second therapeutic agent. In certain embodiments it is preferred that the therapeutic effects of each active ingredient overlap for at least a portion of the duration of each therapeutic agent so that the overall therapeutic effect of the combination therapy is attributable in part to the combined or synergistic effects of the combination therapy.

Delivery

The siRNA molecules as disclosed herein are delivered to the target tissue of the eye by direct application of the molecules prepared with a carrier or a diluent.

The term "naked siRNA" refers to siRNA molecules that are free from any delivery vehicle or formulation that acts to assist, promote or facilitate entry into the cell, including viral sequences, viral particles, liposome formulations, lipofectin or precipitating agents and the like. For example, siRNA in PBS or an acceptable ophthalmological formulation is "naked siRNA". In certain embodiments of the invention the siRNA is delivered as naked siRNA. For certain applications, a formulation that increases the residence time of the siRNA in the eye or nasal passage may be desired, for example, by addition of a polymer or viscosity enhancing agent.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A review of the considerations to be taken into account in the preparation of a pharmaceutical composition for topical ocular delivery or intranasal delivery, can be found in Bar-Ilan and Neumann, in Textbook of Ocular Pharmacology, Zimmerman et al eds., Lippencott-Raven 1997.

Topical routes of administration are preferably employed for providing the subject with an effective dosage of the therapeutic siRNA compounds. Dosage forms may include dispersions, suspensions, solutions, ointments and the like. In certain preferred embodiments the pharmaceutical composition of the invention comprising at least one siRNA is delivered as eye drops. In another embodiment the pharmaceutical composition of the invention comprising at least one siRNA is delivered as a spray or mist. For example U.S. Pat. No. 4,052,985 discloses ophthalmic spray applicators.

In certain embodiments of the present invention the siRNA reaches its target cell locally, for example direct contact or by diffusion through cells, tissue or intracellular fluid. The siRNAs or pharmaceutical compositions of the present invention are administered and dosed in accordance with good medical practice, taking into account the clinical condition of the individual patient, the disease to be treated, scheduling of administration, patient age, sex, body weight and other factors known to medical practitioners.

The "therapeutically effective dose" for purposes herein is thus determined by such considerations as are known in the art. The dose must be effective to achieve improvement including but not limited to an improved course of disease, more rapid recovery, improvement of symptoms, elimination of symptoms and other indicators as are selected as appropriate measures by those skilled in the art. The siRNA of the invention can be administered in a single dose or in multiple doses.

In general, the active dose of compound for humans is in the range of from 1 ng/kg to about 20-100 mg/kg body weight per day, preferably about 0.01 mg/kg to about 2-10 mg/kg body weight per day, in a regimen of one dose per day or twice or three or more times per day for a single dose or multiple dose regimen. In certain embodiments the siRNA compounds are formulated for topical application to the eye as eye drops and comprise about 5 μg/μl to about 60 μg/μl by volume of the composition, about 6.6 μg/μl by volume of the composition, about 25 μg/μl by volume of the composition, about 33.3 μg/μl by volume of the composition, about 50 μg/μl by volume of the composition.

The pH of the formulation is about pH 5 to about pH 8, or about pH 5 to about pH 7, or from about pH 5 to about pH 6. In certain embodiments the pH is about Ph 5.9, about pH 6.15, about pH 6.25, about pH 6.3, about pH 6.5, about pH 7.25. The compounds of the present invention can be administered topically to the surface of the eye. It should be noted that the compound is preferably applied as the compound or as pharmaceutically acceptable salt active ingredient in combination with pharmaceutically acceptable carriers, solvents, diluents, excipients, adjuvants and or vehicles. As disclosed herein the preferred method of delivery is topical application of an ophthalmic composition to the eye.

Liquid forms may be prepared for drops or spray. The liquid compositions include aqueous solutions, with and without organic co-solvents, aqueous or oil suspensions, emulsions with edible oils, as well as similar pharmaceutical vehicles.

These compounds may be administered to humans and other animals for therapy by any suitable route of administration to the eye, as by, for example, a spray or drops, and topically, as by ointments, or drops.

Methods of Treatment

In one aspect, the present invention relates to a method for the treatment of a subject in need of treatment for an eye disease or disorder associated with expression of a gene listed in Tables A1-A4 in the eye of the subject, comprising topically and non-invasively administering to the subject an amount of a chemically modified siRNA which inhibits expression of at least one of the genes. In certain preferred embodiments more than one siRNA compound to one or more than one gene target is administered.

In preferred embodiments the subject being treated is a warm-blooded animal and, in particular, mammals including human.

The methods of the invention comprise topically and non-invasively administering to the eye of the subject one or more inhibitory compounds which down-regulate expression of the genes of Tables A1-A4; and in particular siRNA in a therapeutically effective dose so as to thereby treat the subject.

The term "treatment" refers to both therapeutic treatment and prophylactic or preventative measures, wherein the object is to prevent or slow down, attenuate the related eye disorder as listed above. Those in need of treatment include those already experiencing the disease or condition, those prone to having the disease or condition, and those in which the disease or condition is to be prevented. The compounds of the invention may be administered before, during or subsequent to the onset of the eye disease or condition or symptoms associated therewith. In cases where treatment is for the purpose of prevention, then the present invention relates to a method for delaying the onset of or averting the development of the disease or disorder.

Ocular disorders include Acute Zonal Occult Outer Retinopathy, Adie Syndrome, Age Related Macular Degeneration, Amblyopia, Aniridia, Anisocoria, Anophthalmos, Aphakia, Blepharitis, Blepharoptosis, Blepharospasm, Blindness, Cataract, Chalazion, Chorioretinitis, Choroideremia, Coloboma, Conjunctival Diseases, Conjunctivitis, Corneal Diseases, Corneal Dystrophies, Corneal Edema, Corneal Ulcer, Diabetic Macular Edema, Diabetic Retinopathy, Diplopia, Distichiasis, Dry Eye Syndromes, Duane Retraction Syndrome, Ectropion, Endophthalmitis, Entropion, Esotropia, Exfoliation Syndrome, Exotropia, Eye Abnormalities, Eye Neoplasms, General Fibrosis Syndrome, Glaucomas, Gyrate Atrophy, Hemianopsia, Hermanski-Pudlak Syndrome, Hordeolum, Horner Syndrome, Hyperopia, Hyphema, Iritis, Kearns-Sayer Syndrome, Keratitis, Keratoconus, Lacrimal Apparatus Diseases, Lacrimal Duct Obstruction, Lens Diseases, Macular Degeneration, Nystagmus, Pathologic, Ocular Motility Disorders, Oculomotor Nerve Diseases, Ophthalmoplegia, Optic Atrophies, Hereditary, Optic Nerve Diseases, Optic Neuritis, Ischemic Optic Neuropathy, Orbital Cellulitis, Papilledema, Presbyopia, Pterygium, Pupil Disorders, Refractive Errors, Retinal Detachment, Retinal Diseases, Retinal Vein Occlusion, Retinal Blastoma, Retinitis Pigmentosa, Retinopathy of Prematurity, Retinoschisis, Scleritis, Scotoma, Strabismus, Sjögrens Syndrome, Thygeson's Superficial Punctate Keratitis, Trachoma, Uveitis.

Oligonucleotides

The oligonucleotides useful in the methods disclosed herein are preferably double stranded oligonucleotides and siRNA compounds and include unmodified and chemically and/or structurally modified compounds.

The selection and synthesis of siRNA corresponding to known genes has been widely reported; see for example Ui-Tei et al., J Biomed Biotechnol. 2006; 65052; Chalk et al., BBRC. 2004, 319(1):264-74; Sioud & Leirdal, Met. Mol Biol. 2004, 252:457-69; Levenkova et al., Bioinform. 2004, 20(3):430-2; Ui-Tei et al., NAR. 2004, 32(3):936-48. For examples of the use and production of modified siRNA see for example Braasch et al., Biochem. 2003, 42(26):7967-75; Chiu et al., RNA. 2003, 9(9):1034-48; PCT Publication Nos. WO 2004/015107 and WO 02/44321 and U.S. Pat. Nos. 5,898,031 and 6,107,094.

The present invention provides double-stranded oligonucleotides (e.g. siRNAs), which down-regulate the expression of a desired gene. A siRNA of the invention is a duplex oligoribonucleotide in which the sense strand is derived from the mRNA sequence of the desired gene, and the antisense strand is complementary to the sense strand. In general, some deviation from the target mRNA sequence is tolerated without compromising the siRNA activity (see e.g. Czauderna et al., NAR. 2003, 31(11):2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

In some embodiments the siRNA is blunt ended, i.e. Z and Z' are absent, on one or both ends. More specifically, the siRNA may be blunt ended on the end defined by the 5'-terminus of the first strand and the 3'-terminus of the second strand, and/or the end defined by the 3'-terminus of the first strand and the 5'-terminus of the second strand.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 5 nucleotides.

The length of RNA duplex is from about 18 to about 40 ribonucleotides, preferably 19, 21 or 23 ribonucleotides. Further, the length of each strand may independently have a length selected from the group consisting of about 15 to about 40 bases, preferably 18 to 23 bases and more preferably 19, 21 or 23 ribonucleotides. In some embodiments a 20 or 22-mer molecule may be contemplated.

In certain embodiments the complementarity between said first strand and the target nucleic acid is perfect (100%). In some embodiments, the strands are substantially complementary, i.e. having one, two or up to three mismatches between said first strand and the target nucleic acid. Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 2-100 nucleobases, preferably about 2 to about 30 nucleobases.

In preferred embodiments of the compounds of the invention having alternating ribonucleotides modified in at least one of the antisense and the sense strands of the compound, for 19-mer and 23-mer oligomers the ribonucleotides at the 5' and 3' termini of the antisense strand are modified in their sugar residues, and the ribonucleotides at the 5' and 3' termini of the sense strand are unmodified in their sugar residues. For 21-mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, it is preferred that the middle nucleotide of the antisense strand is unmodified.

Additionally, the invention provides siRNA comprising a double stranded nucleic acid molecule wherein 1, 2, or 3 of the nucleotides in one strand or both strands are substituted thereby providing at least one base pair mismatch. The substituted nucleotides in each strand are preferably in the terminal region of one strand or both strands.

According to one preferred embodiment of the invention, the antisense and the sense strands of the oligonucleotide/siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

Any siRNA sequence disclosed herein can be prepared having any of the modifications/structures disclosed herein. The combination of sequence plus structure is novel and can be used in the treatment of the conditions disclosed herein.

siRNA Structures

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol Biol.; 2004, 252:457-69; Levenkova et al., Bioinform. 2004, 20(3):430-2; Ui-Tei et al., NAR. 2004, 32(3):936-48).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107, 094, teach chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in Drosophila embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl (2'-OMe) modifications. Holen et al (NAR. 2003, 31(9): 2401-07) report that an siRNA having small numbers of 2'-OMe modified nucleosides gave good activity compared to wild type but that the activity decreased as the numbers of 2'-OMe modified nucleosides was increased. Chiu and Rana (RNA. 2003, 9:1034-48) teach that incorporation of 2'-OMe modified nucleosides in the sense or antisense strand (fully modified strands) severely reduced siRNA activity relative to unmodified siRNA. The placement of a 2'-OMe group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107). The molecules of the present invention offer an advantage in that they are non-toxic and may be formulated as pharmaceutical compositions for treatment of various diseases.

The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. Molecules comprising one or more abasic moiety (unconventional or pseudonucleotide) are encompassed by the present invention, as well as molecules comprising alternating RNA and DNA nucleotides.

In addition, analogues of polynucleotides can be prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA) is replaced with a polyamide backbone which is similar to that found in peptides. PNA analogs have been shown to be resistant to enzymatic degradation and to have extended lives in vivo and in vitro.

Possible modifications to the sugar residue are manifold and include 2'-O alkyl, locked nucleic acid (LNA), glycol nucleic acid (GNA), threose nucleic acid (TNA), arabinoside, altritol (ANA) and other, 6-membered sugars including morpholinos, and cyclohexinyls. Further, said molecules may additionally contain modifications on the sugar, such as 2' alkyl, 2' fluoro, 2'O allyl, 2' amine and 2' alkoxy. Additional sugar modifications are discussed herein.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1): 439-447) and in PCT Patent Publication No. WO 2004/083430.

The compounds of the present invention can be synthesized using one or more inverted nucleotides, for example inverted thymidine or inverted adenine (for example see Takei, et al., 2002. JBC 277(26):23800-06).

Backbone modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, and phosphonoacetate derivatives. Certain structures include siRNA compounds having one or a plurality of 2'-5' internucleotide linkages (bridges or backbone).

Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

The molecules of the present invention may comprise siRNAs, synthetic siRNAs, shRNAs and synthetic shRNAs, in addition to other nucleic acid sequences or molecules which encode such molecules or other inhibitory nucleotide molecules.

The compounds of the present invention may further comprise an end modification. A biotin group may be attached to either the most 5' or the most 3' nucleotide of the first and/or second strand or to both ends. In a more preferred embodiment the biotin group is coupled to a polypeptide or a protein. It is also within the scope of the present invention that the polypeptide or protein is attached through any of the other aforementioned modifications.

The various end modifications as disclosed herein are preferably located at the ribose moiety of a nucleotide of the nucleic acid as disclosed herein. More particularly, the end modification may be attached to or replace any of the OH-groups of the ribose moiety, including but not limited to the 2'OH, 3'OH and 5'OH position, provided that the nucleotide thus modified is a terminal nucleotide. Inverted abasic or abasic are nucleotides, either deoxyribonucleotides or ribonucleotides which do not have a nucleobase moiety. This kind of compound is, inter alia, described in Sternberger, et al., (Antisense Nucleic Acid Drug Dev, 2002.12, 131-43).

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks. Further provided by the present invention is an siRNA encoded by any of the molecules disclosed herein, a vector encoding any of the molecules disclosed herein, and a pharmaceutical composition comprising any of the molecules disclosed herein or the vectors encoding them; and a pharmaceutically acceptable carrier.

Particular molecules to be administered according to the methods of the present invention are disclosed below under the heading "structural motifs". For the sake of clarity, any of these molecules can be administered according to any of the methods of the present invention.

Structural Motifs

As disclosed herein the siRNA compounds that are chemically and or structurally modified according to one of the following modifications set forth in Structures below or as tandem siRNA or RNAstar (see below) are useful in the methods of the present invention. Tables 1-36 provide sense and antisense oligonucleotide pairs, set forth in SEQ ID NOS: 59-33596, useful in preparing corresponding siRNA compounds.

In one aspect the present invention provides a compound set forth as Structure (A):

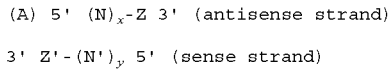

wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein each of x and y is an integer between 18 and 40;
wherein each of Z and Z' may be present or absent, but if present is 1-5 consecutive nucleotides covalently attached at the 3' terminus of the strand in which it is present; and
and wherein the sequence of $(N)_x$ comprises an antisense sequence substantially complementary to about 18 to about 40 consecutive ribonucleotides in the mRNA of a gene expressed in the retina and associated with an ocular disease or disorder. In some embodiments the mRNA is set forth in any one of SEQ ID NOS:1-58.

In certain embodiments the present invention provides a compound having structure B

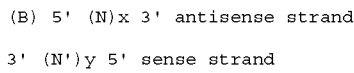

wherein each of $(N)_x$ and $(N')_y$ is an oligonucleotide in which each consecutive N or N' is an unmodified ribonucleotide or a modified ribonucleotide joined to the next N or N' by a covalent bond;
wherein each of x and y=19, 21 or 23 and $(N)_x$ and $(N')_y$ are fully complementary
wherein alternating ribonucleotides in each of $(N)_x$ and $(N')_y$ comprise 2'-OMe sugar modified ribonucleotides;
wherein the sequence of $(N')_y$ is a sequence complementary to $(N)x$; and wherein the sequence of $(N)_x$ comprises an antisense sequence substantially complementary to about 18 to about 40 consecutive ribonucleotides in the mRNA set forth in any one of SEQ ID NOS:1-58.

In some embodiments each of $(N)_x$ and $(N')_y$ is independently phosphorylated or non-phosphorylated at the 3' and 5' termini.

In certain embodiments of the invention, alternating ribonucleotides are modified in both the antisense and the sense strands of the compound.

In certain embodiments wherein each of x and y=19 or 23, each N at the 5' and 3' termini of $(N)_x$ is modified; and each N' at the 5' and 3' termini of $(N')_y$ is unmodified.

In certain embodiments wherein each of x and y=21, each N at the 5' and 3' termini of $(N)_x$ is unmodified; and each N' at the 5' and 3' termini of $(N')_y$ is modified.

In particular embodiments, when x and y=19, the siRNA consists of a 2'OMe sugar modified ribonucleotides on the first, third, fifth, seventh, ninth, eleventh, thirteenth, fifteenth, seventeenth and nineteenth nucleotide of the antisense strand $(N)_x$, and 2'-OMe sugar modified ribonucleotides in the second, fourth, sixth, eighth, tenth, twelfth, fourteenth, sixteenth and eighteenth nucleotide of the sense strand $(N')_y$. In various embodiments these particular siRNA compounds are blunt ended at both termini.

In some embodiments, the present invention provides a compound having Structure (C):

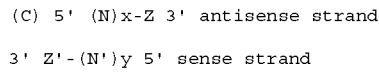

wherein each of N and N' is a nucleotide independently selected from an unmodified ribonucleotide, a modified ribonucleotide, an unmodified deoxyribonucleotide and a modified deoxyribonucleotide;
wherein each of (N)x and (N')y is an oligomer in which each consecutive nucleotide is joined to the next nucleotide by a covalent bond and each of x and y is an integer between 18 and 40;
wherein in (N)x the nucleotides are unmodified or (N)x comprises alternating 2' O Me sugar modified ribonucleotides and unmodified ribonucleotides; and wherein the ribonucleotide located at the middle position of (N)x being 2'OMe sugar modified or unmodified, preferably unmodified;
wherein (N')y comprises unmodified ribonucleotides further comprising one modified nucleotide at a terminal or penultimate position, wherein the modified nucleotide is selected from the group consisting of a mirror nucleotide, a bicyclic nucleotide, a 2'-sugar modified nucleotide, an altritol nucleotide, or a nucleotide joined to an adjacent nucleotide by an internucleotide linkage selected from a 2'-5' phosphodiester bond, a P-alkoxy linkage or a PACE linkage;
wherein if more than one nucleotide is modified in (N')y, the modified nucleotides may be consecutive;
wherein each of Z and Z' may be present or absent, but if present is 1-5 deoxyribonucleotides covalently attached at the 3' terminus of any oligomer to which it is attached;
wherein the sequence of $(N')_y$ comprises a sequence substantially complementary to (N)x; and wherein the sequence of $(N)_x$ comprises an antisense sequence substantially complementary to about 18 to about 40 consecutive ribonucleotides in the mRNA set forth in any one of SEQ ID NOS:1-58.

In particular embodiments, x=y=19 and in (N)x each modified ribonucleotide is a 2'-OMe sugar modified and the ribonucleotide located at the middle of (N)x is unmodified. Accordingly, in a compound wherein x=19, (N)x comprises 2'-O-methyl sugar modified ribonucleotides at positions 1, 3, 5, 7, 9, 11, 13, 15, 17 and 19. In other embodiments, (N)x comprises 2'-OMe sugar modified ribonucleotides at positions 2, 4, 6, 8, 11, 13, 15, 17 and 19 and may further comprise at least one abasic or inverted abasic pseudo-nucleotide for example in position 5. In other embodiments, (N)x comprises 2'-OMe modified ribonucleotides at positions 2, 4, 8, 11, 13, 15, 17 and 19 and may further comprise at least one abasic or inverted abasic pseudo-nucleotide for example in position 6. In other embodiments, (N)x comprises 2'-OMe modified ribonucleotides at positions 2, 4, 6, 8, 11, 13, 17 and 19 and may further comprise at least one abasic or inverted abasic pseudo-nucleotide for example in position 15. In other embodiments, (N)x comprises 2'-OMe modified ribonucleotides at positions 2, 4, 6, 8, 11, 13, 15, 17 and 19 and may further comprise at least one abasic or inverted abasic pseudo-nucleotide for example in position 14. In other embodiments, (N)x comprises 2'-OMe modified ribonucleotides at positions 1, 2, 3, 7, 9, 11, 13, 15, 17 and 19 and may further comprise at least one abasic or inverted abasic pseudo-nucleotide for example in position 5. In other embodiments, (N)x comprises 2'-OMe modified ribonucleotides at positions 1, 2, 3, 5, 7, 9, 11, 13, 15, 17 and 19 and may further comprise at least one abasic or inverted abasic pseudo-nucleotide for example in position 6. In other embodiments, (N)x comprises 2'-OMe modified ribonucleotides at positions 1, 2, 3, 5, 7, 9, 11, 13, 17 and 19 and may further comprise at least one abasic or inverted abasic pseudo-nucleotide for example in position 15. In other embodiments, (N)x comprises 2'-OMe modified ribonucleotides at positions 1, 2, 3, 5, 7, 9, 11, 13, 15, 17 and 19 and may further comprise at least one abasic or inverted abasic pseudo-nucleotide for example in position 14. In other embodiments, (N)x comprises 2'-OMe modified ribonucleotides at positions 2, 4, 6, 7, 9, 11, 13, 15, 17 and 19 and may further comprise at least one abasic or inverted abasic pseudo-nucleotide for example in position 5. In other embodiments, (N)x comprises 2'-OMe modified ribonucleotides at positions 1, 2, 4, 6, 7, 9, 11, 13, 15, 17 and 19 and may further comprise at least one abasic or inverted abasic pseudo-nucleotide for example in position 5. In other embodiments, (N)x comprises 2'-OMe modified ribonucleotides at positions 2, 4, 6, 8, 11, 13, 14, 16, 17 and 19 and may further comprise at least one abasic or inverted abasic pseudo-nucleotide for example in position 15. In other embodiments, (N)x comprises 2'-OMe modified ribonucleotides at positions 1, 2, 3, 5, 7, 9, 11, 13, 14, 16, 17 and 19 and may further comprise at least one abasic or inverted abasic pseudo-nucleotide for example in position 15. In other embodiments, (N)x comprises 2'-OMe modified ribonucleotides at positions 2, 4, 6, 8, 11, 13, 15, 17 and 19 and may further comprise at least one abasic or inverted abasic pseudo-nucleotide for example in position 7. In other embodiments, (N)x comprises 2'-OMe sugar modified ribonucleotides at positions 2, 4, 6, 11, 13, 15, 17 and 19 and may further comprise at least one abasic or inverted abasic pseudo-nucleotide for example in position 8. In other embodiments, (N)x comprises 2'-OMe sugar modified ribonucleotides at positions 2, 4, 6, 8, 11, 13, 15, 17 and 19 and may further comprise at least one abasic or inverted abasic pseudo-nucleotide for example in position 9. In other embodiments, (N)x comprises 2'-OMe sugar modified ribonucleotides at positions 2, 4, 6, 8, 11, 13, 15, 17 and 19 and may further comprise at least one abasic or inverted abasic pseudo-nucleotide for example in position 10. In other embodiments, (N)x comprises 2'-OMe sugar modified ribonucleotides at positions 2, 4, 6, 8, 13, 15, 17 and 19 and may further comprise at least one abasic or inverted abasic pseudo-nucleotide for example in position 11. In other embodiments, (N)x comprises 2'-OMe sugar modified ribonucleotides at positions 2, 4, 6, 8, 11, 13, 15, 17 and 19 and may further comprise at least one abasic or inverted abasic pseudo-nucleotide for example in position 12. In other embodiments, (N)x comprises 2'-OMe sugar modified ribonucleotides at positions 2, 4, 6, 8, 11, 15, 17 and 19 and may further comprise at least one abasic or inverted abasic pseudo-nucleotide for example in position 13.

In yet other embodiments (N)x comprises at least one nucleotide mismatch relative to the target gene. In certain preferred embodiments, (N)x comprises a single nucleotide mismatch on position 5, 6, or 14. In one embodiment of Structure (C), at least two nucleotides at either or both the 5' and 3' termini of (N')y are joined by a 2'-5' phosphodiester bond. In certain preferred embodiments x=y=19 or x=y=23; in (N)x the nucleotides alternate between 2'-OMe sugar modified ribonucleotides and unmodified ribonucleotides, and the ribonucleotide located at the middle of (N)x being unmodified; and three nucleotides at the 3' terminus of (N')y are joined by two 2'-5' phosphodiester bonds (set forth herein as Structure I). In other preferred embodiments, x=y=19 or x=y=23; in (N)x the nucleotides alternate between 2'-OMe sugar modified ribonucleotides and unmodified ribonucleotides, and the ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N)y is 2'-OMe sugar modified. In another preferred embodiment, in (N)x the nucleotides alternate between 2'-OMe sugar modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-methyl (3'-OMe) modifications.

In certain preferred embodiments of Structure C, x=y=19 and in (N')y, at least one position comprises an abasic or inverted abasic pseudo-nucleotide, preferably five positions comprises an abasic or inverted abasic pseudo-nucleotides. In various embodiments, the following positions comprise an abasic or inverted abasic: positions 1 and 16-19, positions 15-19, positions 1-2 and 17-19, positions 1-3 and 18-19, positions 1-4 and 19 and positions 1-5. (N')y may further comprise at least one LNA nucleotide.

In certain preferred embodiments of Structure C, x=y=19 and in (N')y the nucleotide in at least one position comprises a mirror nucleotide, a deoxyribonucleotide and a nucleotide joined to an adjacent nucleotide by a 2'-5' internucleotide bond.

In certain preferred embodiments of Structure C, x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. In certain embodiments (N')y further comprises a 5' terminal cap nucleotide such as 5'-O-methyl DNA or an abasic or inverted abasic pseudo-nucleotide as an overhang.

In yet other embodiments (N')y comprises at least one nucleotide mismatch relative to the target gene. In certain preferred embodiments, (N')y comprises a single nucleotide mismatch on position 6, 14, or 15.

In yet other embodiments (N')y comprises a DNA at position 15 and L-DNA at one or both of positions 17 and 18. In that structure, position 2 may further comprise an L-DNA or an abasic pseudo-nucleotide.

Other embodiments of Structure C are envisaged wherein x=y=21 or wherein x=y=23; in these embodiments the modifications for (N')y discussed above instead of being on positions 15, 16, 17, 18 are on positions 17, 18, 19, 20 for 21 mer and on positions 19, 20, 21, 22 for 23 mer; similarly the modifications at one or both of positions 17 and 18 are on one or both of positions 19 or 20 for a 21 mer and one or both of positions 21 and 22 for a 23 mer. All modifications in the 19 mer are similarly adjusted for the 21 and 23 mers.

According to various embodiments of Structure (C), in (N')y 2, 3, 4, 5, 6, 7, 8, 9, 10, 11, 12, 13 or 14 consecutive ribonucleotides at the 3' terminus are linked by 2'-5' internucleotide linkages In one preferred embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'-O-methyl sugar modification. In certain preferred embodiments of Structure C, x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16, 17, 18, 16-17, 17-18, or 16-18 in (N')y are joined by a 2'-5' internucleotide bond.

In certain embodiments (N')y comprises an L-DNA at position 2 and 2'-5' internucleotide bonds at positions 16, 17, 18, 16-17, 17-18, or 16-18. In certain embodiments (N')y comprises 2'-5' internucleotide bonds at positions 16, 17, 18, 16-17, 17-18, or 16-18 and a 5' terminal cap nucleotide.

According to various embodiments of Structure (C), in (N')y 2, 3, 4, 5, 6, 7, 8, 9, 10, 11, 12, 13 or 14 consecutive nucleotides at either terminus or 2-8 modified nucleotides at each of the 5' and 3' termini are independently mirror nucleotides. In some embodiments the mirror nucleotide is an L-ribonucleotide. In other embodiments the mirror nucleotide is an L-deoxyribonucleotide. The mirror nucleotide may further be modified at the sugar or base moiety or in an internucleotide linkage.

In one preferred embodiment of Structure (C), the 3' terminal nucleotide or two or three consecutive nucleotides at the 3' terminus of (N')y are L-deoxyribonucleotides.

In other embodiments of Structure (C), in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one series of preferred embodiments, three, four or five consecutive nucleotides at the 5' terminus of (N')y comprise the 2'-OMe modification. In another preferred embodiment, three consecutive nucleotides at the 3' terminus of (N')y comprise the 2'-O-methyl modification.

In some embodiments of Structure (C), in (N')y 2, 3, 4, 5, 6, 7, 8, 9, 10, 11, 12, 13 or 14 consecutive ribonucleotides at either or 2-8 modified nucleotides at each of the 5' and 3' termini are independently bicyclic nucleotide. In various embodiments the bicyclic nucleotide is a locked nucleic acid (LNA). A 2'-O,4'-C-ethylene-bridged nucleic acid (ENA) is a species of LNA (see below).

In various embodiments (N')y comprises modified nucleotides at the 5' terminus or at both the 3' and 5' termini.

In some embodiments of Structure (C), at least two nucleotides at either or both the 5' and 3' termini of (N')y are joined by P-ethoxy backbone modifications. In certain preferred embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle position of (N)x being unmodified; and four consecutive nucleotides at the 3' terminus or at the 5' terminus of (N')y are joined by three P-ethoxy backbone modifications. In another preferred embodiment, three consecutive nucleotides at the 3' terminus or at the 5' terminus of (N')y are joined by two P-ethoxy backbone modifications.

In some embodiments of Structure (C), in (N')y 2, 3, 4, 5, 6, 7 or 8, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one preferred embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one specific embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified, or the ribonucleotides in (N)x being unmodified In another embodiment of Structure (C), the present invention provides a compound wherein x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA.

In another embodiment of Structure (C), five consecutive nucleotides at the 5' terminus of (N')y comprise the 2'-O-methyl sugar modification and two consecutive nucleotides at the 3' terminus of (N')y are L-DNA.

In yet another embodiment, the present invention provides a compound wherein x=y=19 or x=y=23; (N)x consists of unmodified ribonucleotides; three consecutive nucleotides at the 3' terminus of (N')y are joined by two 2'-5' phosphodiester bonds and three consecutive nucleotides at the 5' terminus of (N')y are LNA such as ENA.

According to other embodiments of Structure (C), in (N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some preferred embodiments in (N')y, 1 or 2 consecutive nucleotides at each of the 5' and 3' termini are PACE nucleotides. Examples of PACE nucleotides and analogs are disclosed in U.S. Pat. Nos. 6,693,187 and 7,067,641 both incorporated by reference.

In additional embodiments, the present invention provides a compound having Structure (D):

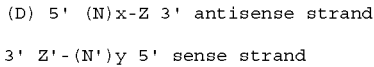

(D) 5' (N)x-Z 3' antisense strand

3' Z'-(N')y 5' sense strand wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein (N)x comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein (N')y comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')y is a sequence substantially complementary to (N)x; and wherein the sequence of $(N)_x$ comprises an antisense sequence having substantial complementarity to about 18 to about 40 consecutive ribonucleotides in the mRNA set forth in any one of SEQ ID NOS:1-58.

In one embodiment of Structure (D), x=y=19 or x=y=23; (N)x comprises unmodified ribonucleotides in which two consecutive nucleotides linked by one 2'-5' internucleotide linkage at the 3' terminus; and (N')y comprises unmodified ribonucleotides in which two consecutive nucleotides linked by one 2'-5' internucleotide linkage at the 5' terminus.

In some embodiments, x=y=19 or x=y=23; (N)x comprises unmodified ribonucleotides in which three consecutive nucleotides at the 3' terminus are joined together by two 2'-5' phosphodiester bonds; and (N')y comprises unmodified ribonucleotides in which four consecutive nucleotides at the 5' terminus are joined together by three 2'-5' phosphodiester bonds (set forth herein as Structure II).

According to various embodiments of Structure (D) 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are linked by 2'-5' internucleotide linkages.

According to one preferred embodiment of Structure (D), four consecutive nucleotides at the 5' terminus of (N')y are joined by three 2'-5' phosphodiester bonds and three consecutive nucleotides at the 3' terminus of (N')x are joined by two 2'-5' phosphodiester bonds. Three nucleotides at the 5' terminus of (N')y and two nucleotides at the 3' terminus of (N')x may also comprise 3'-O-methyl modifications.

According to various embodiments of Structure (D), 2, 3, 4, 5, 6, 7, 8, 9, 10, 11, 12, 13 or 14 consecutive nucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently mirror nucleotides. In some embodiments the mirror is an L-ribonucleotide. In other embodiments the mirror nucleotide is L-deoxyribonucleotide.

In other embodiments of Structure (D), 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one preferred embodiment of Structure (D), five consecutive nucleotides at the 5' terminus of (N')y comprise the 2'-O-methyl modification and five consecutive nucleotides at the 3' terminus of (N')x comprise the 2'-O-methyl modification. In another preferred embodiment of Structure (D), ten consecutive nucleotides at the 5' terminus of (N')y comprise the 2'-O-methyl modification and five consecutive nucleotides at the 3' terminus of (N')x comprise the 2'-β-methyl modification. In another preferred embodiment of Structure (D), thirteen consecutive nucleotides at the 5' terminus of (N')y comprise the 2'-O-methyl modification and five consecutive nucleotides at the 3' terminus of (N')x comprise the 2'-O-methyl modification.

In some embodiments of Structure (D), in (N')y 2, 3, 4, 5, 6, 7, 8, 9, 10, 11, 12, 13 or 14 consecutive ribonucleotides starting at the ultimate or penultimate position of the 3' terminus of (N)x and 2, 3, 4, 5, 6, 7, 8, 9, 10, 11, 12, 13 or 14 consecutive ribonucleotides starting at the ultimate or penultimate position of the 5' terminus of (N')y are independently a bicyclic nucleotide. In various embodiments the bicyclic nucleotide is a locked nucleic acid (LNA) such as a 2'-O,4'-C-ethylene-bridged nucleic acid (ENA).

In various embodiments of Structure (D), (N')y comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In various embodiments of Structure (D), (N)x comprises a modified nucleotide selected from a bicyclic nucleotide, a 2' sugar modified nucleotide, a mirror nucleotide, an altritol nucleotide or a nucleotide joined to an adjacent nucleotide by an internucleotide linkage selected from a 2'-5' phosphodiester bond, a P-alkoxy linkage or a PACE linkage;

In embodiments wherein each of the 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In one specific embodiment of Structure (D), five consecutive nucleotides at the 5' terminus of (N')y comprise the 2'-O-methyl modification and two consecutive nucleotides at the 3' terminus of (N')y are L-DNA. In addition, the compound may further comprise five consecutive 2'-β-methyl modified nucleotides at the 3' terminus of (N')x.

In various embodiments of Structure (D), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (E):

(E) 5' (N)x-Z 3' antisense strand

3' Z'-(N')y 5' sense strand wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein (N)x comprises unmodified ribonucleotides further comprising one modified nucleotide at the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein (N')y comprises unmodified ribonucleotides further comprising one modified nucleotide at the 3' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')y is a sequence substantially complementary to (N)x; and wherein the sequence of (N)$_x$ comprises an antisense sequence having substantial complementarity to about 18 to about 40 consecutive ribonucleotides in the mRNA set forth in any one of SEQ ID NOS:1-58.

In certain preferred embodiments the ultimate nucleotide at the 5' terminus of (N)x is unmodified.

According to various embodiments of Structure (E) 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are linked by 2'-5' internucleotide linkages.

According to various embodiments of Structure (E), 2, 3, 4, 5, 6, 7, 8, 9, 10, 11, 12, 13 or 14 consecutive nucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive nucleotides starting at the ultimate or penultimate position of the 3' terminus of (N')y are independently mirror nucleotides. In some embodiments the mirror is an L-ribonucleotide. In other embodiments the mirror nucleotide is L-deoxyribonucleotide.

In other embodiments of Structure (E), 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (E), in (N')y 2, 3, 4, 5, 6, 7, 8, 9, 10, 11, 12, 13 or 14 consecutive ribonucleotides starting at the ultimate or penultimate position of the 5' terminus of (N)x, preferably starting at the 5' penultimate position, and 2, 3, 4, 5, 6, 7, 8, 9, 10, 11, 12, 13 or 14 consecutive ribonucleotides starting at the ultimate or penultimate position of the 3' terminus of (N')y are independently a bicyclic nucleotide. In various embodiments the bicyclic nucleotide is a locked nucleic acid (LNA) such as a 2'-O,4'-C-ethylene-bridged nucleic acid (ENA).

In various embodiments of Structure (E), (N')y comprises modified nucleotides selected from a bicyclic nucleotide, a 2' sugar modified nucleotide, a mirror nucleotide, an altritol nucleotide, a nucleotide joined to an adjacent nucleotide by a P-alkoxy backbone modification or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In various embodiments of Structure (E), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where both 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (E), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (F):

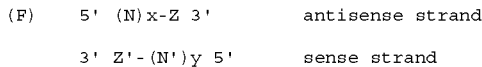

wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein each of (N)x and (N')y comprise unmodified ribonucleotides in which each of (N)x and (N')y independently comprise one modified nucleotide at the 3' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;
wherein in each of (N)x and (N')y modified and unmodified nucleotides are not alternating;
wherein each of Z and Z' may be present or absent, but if present is 1-5 deoxyribonucleotides covalently attached at the 3' terminus of any oligomer to which it is attached;
wherein the sequence of (N')y is a sequence substantially complementary to (N)x; and wherein the sequence of (N)$_x$ comprises an antisense sequence having substantial complementarity to about 18 to about 40 consecutive ribonucleotides in mRNA set forth in any one of SEQ ID NOS:1-58.

In some embodiments of Structure (F), x=y=19 or x=y=23; (N')y comprises unmodified ribonucleotides in which two consecutive nucleotides at the 3' terminus comprises two consecutive mirror deoxyribonucleotides; and (N)x comprises unmodified ribonucleotides in which one nucleotide at the 3' terminus comprises a mirror deoxyribonucleotide (set forth as Structure III).

According to various embodiments of Structure (F) 2, 3, 4, 5, 6, 7, 8, 9, 10, 11, 12, 13 or 14 consecutive ribonucleotides independently beginning at the ultimate or penultimate position of the 3' termini of (N)x and (N')y are linked by 2'-5' internucleotide linkages.

According to one preferred embodiment of Structure (F), three consecutive nucleotides at the 3' terminus of (N')y are joined by two 2'-5' phosphodiester bonds and three consecutive nucleotides at the 3' terminus of (N')x are joined by two 2'-5' phosphodiester bonds.

According to various embodiments of Structure (F), 2, 3, 4, 5, 6, 7, 8, 9, 10, 11, 12, 13 or 14 consecutive nucleotides independently beginning at the ultimate or penultimate position of the 3' termini of (N)x and (N')y are independently mirror nucleotides. In some embodiments the mirror nucleotide is an L-ribonucleotide. In other embodiments the mirror nucleotide is an L-deoxyribonucleotide.

In other embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In some embodiments of Structure (F), 2, 3, 4, 5, 6, 7, 8, 9, 10, 11, 12, 13 or 14 consecutive ribonucleotides independently beginning at the ultimate or penultimate position of the 3' termini of (N)x and (N')y are independently a bicyclic nucleotide. In various embodiments the bicyclic nucleotide is a locked nucleic acid (LNA) such as a 2'-O,4'-C-ethylene-bridged nucleic acid (ENA).

In various embodiments of Structure (F), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at both the 3' and 5' termini.

In various embodiments of Structure (F), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 3' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (F), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (

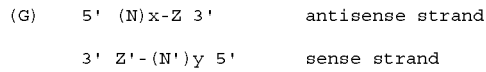

wherein each of N and N' is a nucleotide selected from an unmodified ribonucleotide, a modified ribonucleotide, an unmodified deoxyribonucleotide or a modified deoxyribonucleotide;
wherein each of (N)x and (N')y is an oligomer in which each consecutive nucleotide is joined to the next nucleotide by a covalent bond and each of x and y is an integer between 18 and 40;
wherein each of (N)x and (N')y comprise unmodified ribonucleotides in which each of (N)x and (N')y independently comprise one modified nucleotide at the 5' terminal or penultimate position wherein the modified nucleotide is selected from the group consisting of a bicyclic nucleotide, a 2' sugar modified nucleotide, a mirror nucleotide, a nucleotide joined to an adjacent nucleotide by a P-alkoxy backbone modification or a nucleotide joined to an adjacent nucleotide by a 2'-5' phosphodiester bond;
wherein for (N)x the modified nucleotide is preferably at penultimate position of the 5' terminal;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of (N')$_y$ is a sequence substantially complementary to (N)x; and wherein the sequence of (N)$_x$ comprises an antisense sequence having substantial complementarity to about 18 to about 40 consecutive ribonucleotides in the mRNA set forth in any one of SEQ ID NOS:1-58.

In some embodiments of Structure (G), x=y=19.

According to various embodiments of Structure (G) 2, 3, 4, 5, 6, 7, 8, 9, 10, 11, 12, 13 or 14 consecutive ribonucleotides independently beginning at the ultimate or penultimate position of the 5' termini of (N)x and (N')y are linked by 2'-5' internucleotide linkages. For (N)x the modified nucleotides preferably starting at the penultimate position of the 5' terminal.

According to various embodiments of Structure (G), 2, 3, 4, 5, 6, 7, 8, 9, 10, 11, 12, 13 or 14 consecutive nucleotides independently beginning at the ultimate or penultimate position of the 5' termini of (N)x and (N')y are independently mirror nucleotides. In some embodiments the mirror nucleotide is an L-ribonucleotide. In other embodiments the mirror nucleotide is an L-deoxyribonucleotide. For (N)x the modified nucleotides preferably starting at the penultimate position of the 5' terminal.

In other embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe). In some preferred embodiments the consecutive modified nucleotides preferably begin at the penultimate position of the 5' terminus of (N)x.

In one preferred embodiment of Structure (G), five consecutive ribonucleotides at the 5' terminus of (N')y comprise a 2'-O-methyl modification and one ribonucleotide at the 5' penultimate position of (N')x comprises a 2'-O-methyl modification. In another preferred embodiment of Structure (G), five consecutive ribonucleotides at the 5' terminus of (N')y comprise a 2'-O-methyl modification and two consecutive ribonucleotides at the 5' terminal position of (N')x comprise a 2'-O-methyl modification.

In some embodiments of Structure (G), 2, 3, 4, 5, 6, 7, 8, 9, 10, 11, 12, 13 or 14 consecutive ribonucleotides independently beginning at the ultimate or penultimate position of the 5' termini of (N)x and (N')y are bicyclic nucleotides. In various embodiments the bicyclic nucleotide is a locked nucleic acid (LNA) such as a 2'-O,4'-C-ethylene-bridged nucleic acid (ENA). In some preferred embodiments the consecutive modified nucleotides preferably begin at the penultimate position of the 5' terminus of (N)x.

In various embodiments of Structure (G), (N')y comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In various embodiments of Structure (G), (N)x comprises a modified nucleotide selected from a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage at the 5' terminus or at each of the 3' and 5' termini.

In one embodiment where each of 3' and 5' termini of the same strand comprise a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond. In various embodiments of Structure (G), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In additional embodiments, the present invention provides a compound having Structure (H):

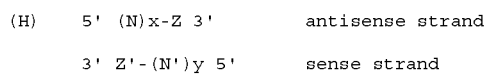

(H)  5' (N)x-Z 3'        antisense strand

3' Z'-(N')y 5'       sense strand wherein each of N and N' is a nucleotide selected from an unmodified ribonucleotide, a modified ribonucleotide, an unmodified deoxyribonucleotide or a modified deoxyribonucleotide;

wherein each of (N)x and (N')y is an oligomer in which each consecutive nucleotide is joined to the next nucleotide by a covalent bond and each of x and y is an integer between 18 and 40;

wherein (N)x comprises unmodified ribonucleotides further comprising one modified nucleotide at the 3' terminal or penultimate position or the 5' terminal or penultimate position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein (N')y comprises unmodified ribonucleotides further comprising one modified nucleotide at an internal position, wherein the modified nucleotide is selected from the group consisting of a bicyclic nucleotide, a 2' sugar modified nucleotide, a mirror nucleotide, an altritol nucleotide, or a nucleotide joined to an adjacent nucleotide by an internucleotide linkage selected from a 2'-5' phosphodiester bond, a P-alkoxy linkage or a PACE linkage;

wherein in each of (N)x and (N')y modified and unmodified nucleotides are not alternating;

wherein each of Z and Z' may be present or absent, but if present is 1-5 deoxyribonucleotides covalently attached at the 3' terminus of any oligomer to which it is attached;

wherein the sequence of (N')$_y$ is a sequence substantially complementary to (N)x; and wherein the sequence of (N)$_x$ comprises an antisense sequence having substantial complementarity to about 18 to about 40 consecutive ribonucleotides in mRNA set forth in any one of SEQ ID NOS:1-58.

In one embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or both termini of (N)x are independently 2' sugar modified nucleotides, bicyclic nucleotides, mirror nucleotides, altritol nucleotides or nucleotides joined to an adjacent nucleotide by a 2'-5' phosphodiester bond and 2, 3, 4, 5, 6, 7, 8, 9, 10, 11, 12, 13 or 14 consecutive internal ribonucleotides in (N')y are independently 2' sugar modified nucleotides, bicyclic nucleotides, mirror nucleotides, altritol nucleotides or nucleotides joined to an adjacent nucleotide by a 2'-5' phosphodiester bond. In some embodiments the 2' sugar modification comprises the presence of an amino, a fluoro, an alkoxy or an alkyl moiety. In certain embodiments the 2' sugar modified ribonucleotide comprises a methoxy moiety (2'-OMe).

In another embodiment of Structure (H), 2, 3, 4, 5, 6, 7, 8, 9, 10, 11, 12, 13 or 14 consecutive ribonucleotides independently beginning at the ultimate or penultimate position of the 3' terminus or the 5' terminus or 2-8 consecutive nucleotides at each of 5' and 3' termini of (N')y are independently 2' sugar modified nucleotides, bicyclic nucleotides, mirror nucleotides, altritol nucleotides or nucleotides joined to an adjacent nucleotide by a 2'-5' phosphodiester bond, and 2, 3, 4, 5, 6, 7, 8, 9, 10, 11, 12, 13 or 14 consecutive internal ribonucleotides in (N)x are independently 2' sugar modified nucleotides, bicyclic nucleotides, mirror nucleotides, altritol nucleotides or nucleotides joined to an adjacent nucleotide by a 2'-5' phosphodiester bond.

In one embodiment wherein each of 3' and 5' termini of the same strand comprises a modified nucleotide, the modification at the 5' and 3' termini is identical. In another embodiment, the modification at the 5' terminus is different from the modification at the 3' terminus of the same strand. In one specific embodiment, the modified nucleotides at the 5' terminus are mirror nucleotides and the modified nucleotides at the 3' terminus of the same strand are joined by 2'-5' phosphodiester bond.

In various embodiments of Structure (H), the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In one preferred embodiment of Structure (H), x=y=19; three consecutive ribonucleotides at the 9-11 nucleotide positions 9-11 of (N')y comprise 2'-O-methyl modification and five consecutive ribonucleotides at the 3' terminal position of (N')x comprise 2'-O-methyl modification.

In one aspect the present invention provides a compound having Structure (I) set forth below:

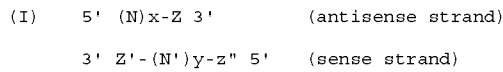

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent, but if present is a capping moiety covalently attached at the 5' terminus of (N')y;
wherein x=18 to 27;
wherein y=18 to 27;
wherein (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide;
wherein in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond; and
wherein the sequence of (N)x is substantially complementary to the sequence of (N')y; and wherein the sequence of $(N)_x$ comprises an antisense sequence having substantial complementarity to about 18 to about 40 consecutive ribonucleotides in mRNA set forth in any one of SEQ ID NOS:1-58.

In some embodiments x=y=19. In other embodiments x=y=23. In some embodiments the at least one unconventional moiety is present at positions 15, 16, 17, or 18 in (N')y. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18.

In other embodiments the unconventional moiety is an abasic moiety. In various embodiments (N')y comprises at least five abasic ribose moieties or abasic deoxyribose moieties.

In yet other embodiments (N')y comprises at least five abasic ribose moieties or abasic deoxyribose moieties and at least one of N' is an LNA.

In some embodiments of Structure (IX) (N)x comprises nine alternating modified ribonucleotides. In other embodiments of Structure (I) (N)x comprises nine alternating modified ribonucleotides further comprising a 2'O modified nucleotide at position 2. In some embodiments (N)x comprises 2'-OMe sugar modified ribonucleotides at the odd numbered positions 1, 3, 5, 7, 9, 11, 13, 15, 17, 19. In other embodiments (N)x further comprises a 2'-OMe sugar modified ribonucleotide at one or both of positions 2 and 18. In yet other embodiments (N)x comprises 2'-OMe sugar modified ribonucleotides at positions 2, 4, 6, 8, 11, 13, 15, 17, 19.

In various embodiments z" is present and is selected from an abasic ribose moiety, a deoxyribose moiety; an inverted abasic ribose moiety, a deoxyribose moiety; C6-amino-Pi; a mirror nucleotide.

In another aspect the present invention provides a compound having Structure (J) set forth below:

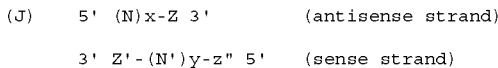

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;

wherein Z and Z' may be present or absent, but if present is independently 1-5 consecutive nucleotides covalently attached at the 3' terminus of the strand in which it is present; wherein z" may be present or absent but if present is a capping moiety covalently attached at the 5' terminus of (N')y;
wherein x=18 to 27;
wherein y=18 to 27;
wherein (N)x comprises modified or unmodified ribonucleotides, and optionally at least one unconventional moiety;
wherein in (N')y at least one unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond; and
wherein the sequence of (N)x is substantially complementary to the sequence of (N')y; and
wherein the sequence of $(N)_x$ comprises an antisense sequence having substantial complementarity to about 18 to about 40 consecutive ribonucleotides in mRNA set forth in any one of SEQ ID NOS:1-58.

In some embodiments x=y=19. In other embodiments x=y=23. In some preferred embodiments (N)x comprises modified and unmodified ribonucleotides, and at least one unconventional moiety.

In some embodiments in (N)x the N at the 3' terminus is a modified ribonucleotide and (N)x comprises at least 8 modified ribonucleotides. In other embodiments at least 5 of the at least 8 modified ribonucleotides are alternating beginning at the 3' end. In some embodiments (N)x comprises an abasic moiety in one of positions 5, 6, 7, 8, 9, 10, 11, 12, 13, 14 or 15.

In some embodiments the at least one unconventional moiety in (N')y is present at positions 15, 16, 17, or 18. In some embodiments the unconventional moiety is selected from a mirror nucleotide, an abasic ribose moiety and an abasic deoxyribose moiety. In some preferred embodiments the unconventional moiety is a mirror nucleotide, preferably an L-DNA moiety. In some embodiments an L-DNA moiety is present at position 17, position 18 or positions 17 and 18. In other embodiments the at least one unconventional moiety in (N')y is an abasic ribose moiety or an abasic deoxyribose moiety.

In various embodiments of Structure (X) z" is present and is selected from an abasic ribose moiety, a deoxyribose moiety; an inverted abasic ribose moiety, a deoxyribose moiety; C6-amino-Pi; a mirror nucleotide.

In yet another aspect the present invention provides a compound having Structure (K) set forth below:

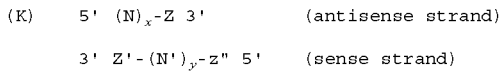

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein Z and Z' may be present or absent, but if present is independently 1-5 consecutive nucleotides covalently attached at the 3' terminus of the strand in which it is present;
wherein z" may be present or absent but if present is a capping moiety covalently attached at the 5' terminus of (N')y;
wherein x=18 to 27;
wherein y=18 to 27;

wherein (N)x comprises a combination of modified or unmodified ribonucleotides and unconventional moieties, any modified ribonucleotide having a 2'-O-methyl on its sugar;
wherein (N')y comprises modified or unmodified ribonucleotides and optionally an unconventional moiety, any modified ribonucleotide having a 2' OMe on its sugar;
wherein the sequence of (N)x is substantially complementary to the sequence of (N')y; and
wherein the sequence of $(N)_x$ comprises an antisense sequence having substantial complementarity to about 18 to about 40 consecutive ribonucleotides in mRNA set forth in any one of SEQ ID NOS:1-58; and wherein there are less than 15 consecutive nucleotides complementary to the mRNA.

In some embodiments x=y=19. In other embodiments x=y=23. In some preferred embodiments the at least one preferred one unconventional moiety is present in (N)x and is an abasic ribose moiety or an abasic deoxyribose moiety. In other embodiments the at least one unconventional moiety is present in (N)x and is a non-base pairing nucleotide analog. In various embodiments (N')y comprises unmodified ribonucleotides. In some embodiments (N)x comprises at least five abasic ribose moieties or abasic deoxyribose moieties or a combination thereof. In certain embodiments (N)x and/or (N')y comprise modified ribonucleotides which do not base pair with corresponding modified or unmodified ribonucleotides in (N')y and/or (N)x.

In various embodiments the present invention provides an siRNA set forth in Structure (L):

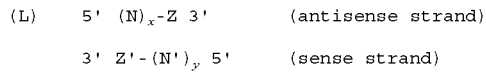

wherein each of N and N' is a nucleotide selected from an unmodified ribonucleotide, a modified ribonucleotide, an unmodified deoxyribonucleotide and a modified deoxyribonucleotide;
wherein each of $(N)_x$ and $(N')_y$ is an oligonucleotide in which each consecutive N or N' is joined to the next N or N' by a covalent bond;
wherein Z and Z' are absent;
wherein x=y=19;
wherein in (N')y the nucleotide in at least one of positions 15, 16, 17, 18 and 19 comprises a nucleotide selected from an abasic pseudo-nucleotide, a mirror nucleotide, a deoxyribonucleotide and a nucleotide joined to an adjacent nucleotide by a 2'-5' internucleotide bond;
wherein (N)x comprises alternating modified ribonucleotides and unmodified ribonucleotides each modified ribonucleotide being modified so as to have a 2'-O-methyl on its sugar and the ribonucleotide located at the middle position of (N)x being modified or unmodified, preferably unmodified; and
wherein the sequence of (N)x is substantially complementary to the sequence of (N')y; and wherein the sequence of $(N)_x$ comprises an antisense sequence having substantial complementarity to about 18 to about 40 consecutive ribonucleotides in mRNA set forth in any one of SEQ ID NOS:1-58.

In some embodiments of Structure (L), in (N')y the nucleotide in one or both of positions 17 and 18 comprises a modified nucleotide selected from an abasic pseudo-nucleotide, a mirror nucleotide and a nucleotide joined to an adjacent nucleotide by a 2'-5' internucleotide bond. In some embodiments the mirror nucleotide is selected from L-DNA and L-RNA. In various embodiments the mirror nucleotide is L-DNA.

In various embodiments (N')y comprises a modified nucleotide at position 15 wherein the modified nucleotide is selected from a mirror nucleotide and a deoxyribonucleotide.

In certain embodiments (N')y further comprises a modified nucleotide or pseudo nucleotide at position 2 wherein the pseudo nucleotide may be an abasic pseudo-nucleotide analog and the modified nucleotide is optionally a mirror nucleotide.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)x further comprises 2'O-Me modified ribonucleotides at one or both positions 2 and 18. In other embodiments (N)x comprises 2'-OMe sugar modified ribonucleotides at positions 2, 4, 6, 8, 11, 13, 15, 17, 19.

Other embodiments of Structures (L), (I) and (J) are envisaged wherein x=y=21 or wherein x=y=23; in these embodiments the modifications for (N')y discussed above instead of being in positions 17 and 18 are in positions 19 and 20 for 21-mer oligonucleotide and 21 and 22 for 23 mer oligonucleotide; similarly the modifications in positions 15, 16, 17, 18 or 19 are in positions 17, 18, 19, 20 or 21 for the 21-mer oligonucleotide and positions 19, 20, 21, 22, or 23 for the 23-mer oligonucleotide. The 2'-OMe modifications on the antisense strand are similarly adjusted. In some embodiments (N)x comprises 2'-OMe sugar modified ribonucleotides at the odd numbered positions (5' to 3'; positions 1, 3, 5, 7, 9, 12, 14, 16, 18, 20 for the 21 mer oligonucleotide [nucleotide at position 11 unmodified] and 1, 3, 5, 7, 9, 11, 13, 15, 17, 19, 21, 23 for the 23 mer oligonucleotide [nucleotide at position 12 unmodified]. In other embodiments (N)x comprises 2'-OMe sugar modified ribonucleotides at positions 2, 4, 6, 8, 10, 12, 14, 16, 18, 20 [nucleotide at position 11 unmodified for the 21 mer oligonucleotide and at positions 2, 4, 6, 8, 10, 13, 15, 17, 19, 21, 23 for the 23 mer oligonucleotide [nucleotide at position 12 unmodified].

In some embodiments (N')y further comprises a 5' terminal cap nucleotide. In various embodiments the terminal cap moiety is selected from an abasic pseudo-nucleotide analog, an inverted abasic pseudo-nucleotide analog, an L-DNA nucleotide, and a C6-imine phosphate (C6 amino linker with phosphate at terminus).

In other embodiments the present invention provides a compound having Structure (M) set forth below:

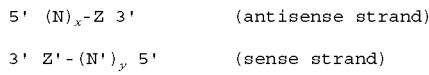

wherein each of N and N' is selected from a pseudo-nucleotide and a nucleotide;
wherein each nucleotide is selected from an unmodified ribonucleotide, a modified ribonucleotide, an unmodified deoxyribonucleotide and a modified deoxyribonucleotide;
wherein each of (N)x and (N')y is an oligonucleotide in which each consecutive N or N' is joined to the next N or N' by a covalent bond;
wherein Z and Z' are absent;
wherein x=18 to 27;
wherein y=18 to 27;
wherein the sequence of (N)x is substantially complementary to the sequence of (N')y; and wherein the sequence of (N)x comprises an antisense sequence having substantial complementarity to about 18 to about 40 consecutive ribonucleotides in mRNA set forth in any one of SEQ ID NOS:1-58;
wherein at least one of N is selected from an abasic pseudo nucleotide, a non-pairing nucleotide analog and a nucleotide mismatch to the mRNA of a target gene in a position of (N)x such that (N)x comprises less than 15 consecutive nucleotides complementary to the mRNA of a target gene.

In other embodiments the present invention provides a double stranded compound having Structure (N) set forth below:

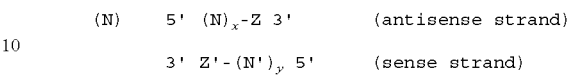

wherein each of N and N' is a nucleotide selected from an unmodified ribonucleotide, a modified ribonucleotide, an unmodified deoxyribonucleotide and a modified deoxyribonucleotide;
wherein each of (N)x and (N')y is an oligonucleotide in which each consecutive N or N' is joined to the next N or N' by a covalent bond;
wherein Z and Z' are absent;
wherein each of x and y is an integer between 18 and 40;
wherein the sequence of (N)x is substantially complementary to the sequence of (N')y; and
wherein the sequence of (N)x comprises an antisense sequence having substantial complementarity to about 18 to about 40 consecutive ribonucleotides in mRNA set forth in any one of SEQ ID NOS:1-58;
wherein (N)x, (N')y or (N)x and (N')y comprise non base-pairing modified nucleotides such that (N)x and (N')y form less than 15 base pairs in the double stranded compound.

In other embodiments the present invention provides a compound having Structure (O) set forth below:

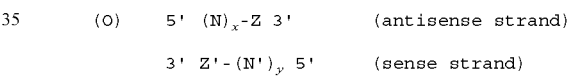

wherein each of N is a nucleotide selected from an unmodified ribonucleotide, a modified ribonucleotide, an unmodified deoxyribonucleotide and a modified deoxyribonucleotide;
wherein each of N' is a nucleotide analog selected from a six membered sugar nucleotide, seven membered sugar nucleotide, morpholino moiety, peptide nucleic acid and combinations thereof;
wherein each of (N)x and (N')y is an oligonucleotide in which each consecutive N or N' is joined to the next N or N' by a covalent bond;
wherein Z and Z' are absent;
wherein each of x and y is an integer between 18 and 40;
wherein the sequence of (N)x is substantially complementary to the sequence of (N')y; and
wherein the sequence of (N)x comprises an antisense sequence having substantial complementarity to about 18 to about 40 consecutive ribonucleotides in mRNA set forth in any one of SEQ ID NOS:1-58.

In other embodiments the present invention provides a compound having Structure (P) set forth below:

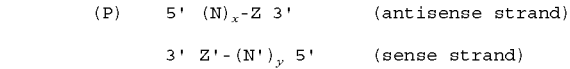

wherein each of N and N' is a nucleotide selected from an unmodified ribonucleotide, a modified ribonucleotide, an unmodified deoxyribonucleotide and a modified deoxyribonucleotide;

wherein each of (N)$_x$ and (N')$_y$ is an oligonucleotide in which each consecutive N or N' is joined to the next N or N' by a covalent bond;

wherein Z and Z' are absent;

wherein each of x and y is an integer between 18 and 40;

wherein one of N or N' in an internal position of (N)x or (N')y or one or more of N or N' at a terminal position of (N)x or (N')y comprises an abasic moiety or a 2' modified nucleotide;

wherein the sequence of (N)x is substantially complementary to the sequence of (N')y; and wherein the sequence of (N)$_x$ comprises an antisense sequence having substantial complementarity to about 18 to about 40 consecutive ribonucleotides in mRNA set forth in any one of SEQ ID NOS:1-58.

In various embodiments (N')y comprises a modified nucleotide at position 15 wherein the modified nucleotide is selected from a mirror nucleotide and a deoxyribonucleotide.

In certain embodiments (N')y further comprises a modified nucleotide at position 2 wherein the modified nucleotide is selected from a mirror nucleotide and an abasic pseudo-nucleotide analog.

In various embodiments the antisense strand (N)x comprises 2'O-Me modified ribonucleotides at the odd numbered positions (5' to 3'; positions 1, 3, 5, 7, 9, 11, 13, 15, 17, 19). In some embodiments (N)x further comprises 2'O-Me modified ribonucleotides at one or both positions 2 and 18. In other embodiments (N)x comprises 2'-OMe sugar modified ribonucleotides at positions 2, 4, 6, 8, 11, 13, 15, 17, 19.

The Structural motifs (A)-(P) described above are useful with any oligonucleotide pair (sense and antisense strands) to a mammalian or non-mammalian gene. In some embodiments the mammalian gene is a human gene preferably selected from the genes provided in Tables A1-A4, with mRNA set forth in SEQ ID NOS:1-58. In certain preferred embodiments the sense and antisense oligonucleotides of the siRNA are selected from any one of siRNA pairs set forth in SEQ ID NOS:59-33,596. Table A5 below shows certain preferred sense and antisense oligonucleotide pairs.

TABLE A5

| TARGET GENE | SENSE (N')y 5'-3' | ANTISENSE (N)x 5'-3' |
|---|---|---|
| P53 | GAGAAUAUUCACCCUUCA | UGAAGGGUGAAAUAUUCUC |
| CASP2 | GCCAGAAUGUGGAACUCCU | AGGAGUUCCACAUUCUGGC |
| RTP801 | GUGCCAACCUGAUGCAGCU | AGCAGCAUCAGGUUGGCAC |
| RTP801 | UACUGUAGCAUGAAACAAA | UUUGUUUCAUGCUACAGUA |
| RTP801 | CAGUACUGUAGCAUGAAAC | GUUUCAUGCUACAGUACUG |
| TP53BP2 | CACCCAGAGAACAUUUAUU | AAUAAAUGUUCUCUGGGUG |
| CYBA | UGGGGACAGAAGUACAUGA | UCAUGUACUUCUGUCCCCA |
| RAC1 | GAGUCCUGCAUCAUUUGAA | UUCAAAUGAUGCAGGACUC |
| SPP1 | GUGCCAUACCAGUUAAACA | UGUUUAACUGGUAUGGCAC |
| SPP1 | GCAAAAUGAAAGAGAACAU | AUGUUCUCUUUCAUUUUGC |
| ASPP1 | CGAACUCAGAGAAAUGUAA | UUACAUUUCUCUGAGUUCG |
| ASPP1 | GGAGAAAAACGUACUGAAA | UUUCAGUACGUUUUUCUCC |
| SOX9 | CCUUCAUGAAGAUGACCGA | UCGGUCAUCUUCAUGAAGG |

For all the above Structures (A)-(P), in various embodiments x=y and each of x and y is 19, 20, 21, 22 or 23. In preferred embodiments, x=y=19. In additional embodiments the compound comprises modified ribonucleotides in alternating positions wherein each N at the 5' and 3' termini of (N)x are modified in their sugar residues and the middle ribonucleotide is not modified, e.g. ribonucleotide in position 10 in a 19-mer strand, position 11 in a 21 mer and position 12 in a 23-mer strand.

In some embodiments where x=y=21 or x=y=23 the position of modifications in the 19 mer are adjusted for the 21 and 23 mers with the proviso that the middle nucleotide of the antisense strand is preferably not modified.

For all the above Structures (A)-(P), in some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 2' termini position using cleavable or non-cleavable phosphate groups. These particular siRNA compounds are also blunt ended and are non-phosphorylated at the termini; however, comparative experiments have shown that siRNA compounds phosphorylated at one or both of the 3'-termini have similar activity in vivo compared to the non-phosphorylated compounds.

For all the above Structures (A)-(P), in some embodiments, the compound is blunt ended, for example wherein both Z and Z' are absent. In an alternative embodiment, the compound comprises at least one 3' overhang, wherein at least one of Z or Z' is present. Z and Z' independently comprises one or more covalently linked modified or non-modified nucleotides, for example inverted dT or dA; dT, LNA, mirror nucleotide and the like. In some embodiments each of Z and Z' are independently selected from dT and dTdT. siRNA in which Z and/or Z' is present have similar activity and stability as siRNA in which Z and Z' are absent.

In certain embodiments for all the above-mentioned Structures, the compound comprises one or more locked nucleic acids (LNA) also defined as bridged nucleic acids or bicyclic nucleotides. Preferred locked nucleic acids are 2'-O, 4'-C-ethylene nucleosides (ENA) or 2'-O, 4'-C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allart, et al., 1998. Nucleosides & Nucleotides 17:1523-1526; Herdewijn et al., 1999. Nucleosides & Nucleotides 18:1371-1376; Fisher et al., 2007, NAR 35(4):1064-1074; all incorporated herein by reference).

The present invention explicitly excludes compounds in which each of N and/or N' is a deoxyribonucleotide (D-A, D-C, D-G, D-T). In certain embodiments (N)x and (N')y may comprise independently 1, 2, 3, 4, 5, 6, 7, 8, or 9 deoxyribonucleotides. In certain embodiments the present invention provides a compound wherein each of N is an unmodified ribonucleotide and the 3' terminal nucleotide or 2, 3, 4, 5, 6, 7, 8, 9, 10, 11, 12, 13 or 14 consecutive nucleotides at the 3' terminus of (N')y are deoxyribonucleotides. In yet other embodiments each of N is an unmodified ribonucleotide and the 5' terminal nucleotide or 2, 3, 4, 5, 6, 7, 8, 9, 10, 11, 12, 13 or 14 consecutive nucleotides at the 5' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide. In certain embodiments the 3' terminal nucleotide or 2, 3, 4, 5, 6, 7, 8, 9, 10, 11, 12 13 or 14 consecutive nucleotides at the 3' terminus of (N')y and the terminal 5' nucleotide or 2, 3, 4, 5, 6, 7, 8, 9, 10, 11, 12 13 or 14 consecutive nucleotides at the 5' terminus of (N)x are deoxyribonucleotides. The present invention excludes compounds in which each of N and/or N' is a deoxyribonucleotide. In some embodiments the 5' terminal nucleotide of N or 2 or 3 consecutive of N and 1, 2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

Unless otherwise indicated, in preferred embodiments of the structures discussed herein the covalent bond between each consecutive N and N' is a phosphodiester bond.

An additional novel molecule provided by the present invention is an oligonucleotide comprising consecutive nucleotides wherein a first segment of such nucleotides encode a first inhibitory RNA molecule, a second segment of such nucleotides encode a second inhibitory RNA molecule, and a third segment of such nucleotides encode a third inhibitory RNA molecule. Each of the first, the second and the third segment may comprise one strand of a double stranded RNA and the first, second and third segments may be joined together by a linker. Further, the oligonucleotide may comprise three double stranded segments joined together by one or more linker.

Thus, one molecule provided by the present invention is an oligonucleotide comprising consecutive nucleotides which encode three inhibitory RNA molecules; said oligonucleotide may possess a triple stranded structure, such that three double stranded arms are linked together by one or more linker, such as any of the linkers presented hereinabove. This molecule forms a "star"-like structure, and may also be referred to herein as RNAstar. Such structures are disclosed in PCT patent publication WO 2007/091269, assigned to the assignee of the present invention and incorporated herein in its entirety by reference.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain preferred embodiments a covalent bond is a phosphodiester bond. Covalent bond encompasses non-phosphorous-containing internucleoside linkages, such as those disclosed in WO 2004/041924 inter alia. Unless otherwise indicated, in preferred embodiments of the structures discussed herein the covalent bond between each consecutive N and N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to a target sequence. In other embodiments (N)x is substantially complementary to a target sequence.

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

The structures disclosed herein, when integrated into antisense and corresponding sense nucleic acid sequences to any target gene, provides siRNA compound useful in reducing expression of that target gene. The target gene is a mammalian or non-mammalian gene. The methods of the invention comprise topically and non-invasively administering to the eye of the subject one or more siRNA compounds which inhibit expression of a target gene in the eye of the subject.

siRNA Synthesis

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver; Kap. 7: 183-208.

Other synthetic procedures are known in the art e.g. the procedures as described in Usman et al., J. Am. Chem. Soc., 1987, 109:7845; Scaringe et al., NAR, 1990, 18:5433; Wincott et al., NAR 1995, 23:2677-2684; and Wincott et al., Methods Mol. Bio., 1997, 74:59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., Science 1992, 256:9923; International Patent Publication No. WO 93/23569; Shabarova et al., NAR 1991, 19:4247; Bellon et al., Nucleosides & Nucleotides, 1997, 16:951; Bellon et al., Bioconjugate Chem 1997, 8:204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology, as described for example in US Patent Publication No. 2004/0019001 (McSwiggen), and in PCT Patent Publication No. WO 2007/091269 (assigned to the assignee of the present invention and incorporated herein in its entirety by reference) wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides.

Thus, the siRNA molecules may be covalently or non-covalently bound or joined by a linker to form a tandem siRNA compound. Such tandem siRNA compounds comprising two siRNA sequences are typically about 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention. A tandem compound comprising two or more siRNAs sequences of the invention is envisaged.

Additionally, the siRNA disclosed herein or any nucleic acid molecule comprising or encoding such siRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any of the siRNA compounds.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of the genes of the invention.

RNA Interference

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

RNA interference (RNAi) is based on the ability of dsRNA species to enter a cytoplasmic protein complex, where it is then targeted to the complementary cellular RNA and specifically degrade it. The RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al., Genes Dev., 2001, 15(2): 188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., Nature, 2001, 409(6818): 363-6; Lee et al., Nature, 2003, 425(6956):415-9). The RISC protein complex recognizes these fragments and complementary mRNA. The whole process is culminated by endonuclease cleavage of target mRNA (McManus & Sharp, Nature Rev Genet, 2002, 3(10):737-47; Paddison & Hannon, Curr Opin Mol Ther. 2003, 5(3):217-24). (For additional information on these terms and proposed mechanisms, see for example Bernstein et al., RNA 2001, 7(11):1509-21; Nishikura, Cell 2001, 107(4):415-8 and PCT publication WO 01/36646).

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods to generate siRNAs capable of specifically targeting numerous endogenously and exogenously expressed genes.

The invention has been described in an illustrative manner, and it is to be understood that the terminology used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

Throughout this application, various publications, including United States patents, are referenced by author and year and patents by number. The disclosures of these publications and patents and patent applications in their entireties are hereby incorporated by reference into this application in order to more fully describe the state of the art to which this invention pertains.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., Molecular cloning: A laboratory manual, Cold Springs Harbor Laboratory, New-York (1989, 1992), and in Ausubel et al., Current Protocols in Molecular Biology, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683, 202; 4,801,531; 5,192,659 and 5,272,057 and incorporated herein by reference. Polymerase chain reaction (PCR) was carried out as in standard PCR Protocols: A Guide To Methods And Applications, Academic Press, San Diego, Calif. (1990). In situ PCR in combination with Flow Cytometry (FACS) can be used for detection of cells containing specific DNA and mRNA sequences (Testoni et al., Blood 1996, 87:3822.) Methods of performing RT-PCR are well known in the art.

Cell Culture

HeLa cells (American Type Culture Collection) were cultured as described in Czauderna, et al. (NAR, 2003. 31:670-82). Human keratinocytes were cultured at 37° C. in Dulbecco's modified Eagle medium (DMEM) containing 10% FCS. The mouse cell line, B16V (American Type Culture Collection), was cultured at 37° C. in Dulbecco's modified Eagle medium (DMEM) containing 10% FCS. Culture conditions were as described in (Methods Find Exp Clin Pharmacol. 1997, 19(4):231-9).

In each case, the cells were subject to the experiments as described herein at a density of about 50,000 cells per well and the double-stranded nucleic acid according to the present invention was added at a concentration of 20 nM, whereby the double-stranded nucleic acid was complexed using 1 μg/ml of a proprietary lipid as described below.

In the histochemical/microscopic figures, arrows were added to draw attention to staining of the tissue.

Animal Models

Model Systems of Glaucoma and of Retinal Ganglion Cells (RGC) Death

ONC Model in Rats

Various animal models are useful for studying the effect of siRNA therapeutics in treating glaucoma. In the optic nerve crush model in rats the orbital optic nerve (ON) of anesthetized rats is exposed through a supraorbital approach, the meninges severed and all axons in the ON transected by crushing with forceps for 10 seconds, 2 mm from the lamina cribrosa. Testing active inhibitors of the invention (such as siRNA) for treating or preventing glaucoma is performed, for example, in the animal models described by Pease et al. (J. Glaucoma, 2006, 15(6):512-9. Manometric calibration and comparison of TonoLab and TonoPen tonometers in rats with experimental glaucoma and in normal mice).

Optic nerve crush (ONC) model in adult Wistar rats is also an accepted model for studying Retinal Ganglion Cells (RGC) death. The onset and kinetics of RGC death in this model are very reproducible; RGC apoptosis begins on day 4-5 after the ONC; massive RGC loss (about 50-60%) is observed on days 7-10 after the ONC; and 95% of the RGC loss is occurs by week 3-4 after the ONC. This model allows for establishment of the neuroprotective efficacy of test drugs in vivo.

In some non-limiting examples, siRNA compounds directed to genes shown in Tables A1-A4 are tested in this animal model which show that these siRNA compounds treat and/or prevent glaucoma and/or RGC death when topically and non-invasively delivered to the eye.

IOP Model in Rats

Intraocular pressure (IOP) is a measurement of the fluid pressure inside the eye. This fluid, called aqueous humor, is circulated and then drained out via specialized outflow pathways. If the drainage system does not function properly, as in prevalent forms of glaucoma, pressure inside the eye builds up. A model of ocular hypertension in Brown Norway rats developed by Dr. J. Morrison and collaborators at the Casey Eye Institute (Portland, Oreg.) is used in this study. The Morrison model involves injection of hypertonic saline into an episcleral vein, leading to blockade of the aqueous humor outflow pathways. This procedure leads to gradual increase of eye pressure and progressive death of RGCs. Importantly, inner retinal atrophy, optic nerve degeneration, and optic nerve head remodeling observed in this model are similar to that seen in human glaucoma. Thus, the Morrison model is considered the best pre-clinical rodent model of glaucoma.

In Vivo Axotomy Model in Rats

In this model RGC apoptosis is induced by axotomy of the optic nerve (ON) in adult Sprague-Dawley rats. The onset and kinetics of RGC death in this model system are very reproducible and allow for the establishment of the neuroprotective efficacy of non-invasively administered siRNA compound in vivo. Using this method, the time course of RGC death follows a predictable course: cell death begins on day 5 and proceeds to the rapid loss of more than 90% of these neurons by 2 weeks.

Vehicle Formulations and Exemplary Eye Drop Formulations

The aqueous eye drop formulation optionally contain various additives incorporated ordinarily, such as buffering agents (e.g., phosphate buffers, borate buffers, citrate buffers, tartarate buffers, acetate buffers, amino acids, sodium acetate, sodium citrate and the like), isotonicities (e.g., saccharides such as sorbitol, glucose and mannitol, polyhydric alcohols such as glycerin, concentrated glycerin, polyethylene glycol and propylene glycol, salts such as sodium chloride), preservatives or antiseptics (e.g., benzalkonium chloride, benzethonium chloride, p-oxybenzoates such as methyl p-oxybenzoate or ethyl p-oxybenzoate, benzyl alcohol, phenethyl alcohol, sorbic acid or its salts, thimerosal, chlorobutanol and the like), solubilizing aids or stabilizing agents (e.g., cyclodextrins and their derivative, water-soluble polymers such as polyvinyl pyrrolidone) surfactants such as polysorbate 80 (Tween 80)), pH modifiers (e.g., hydrochloric acid, acetic acid, phosphoric acid, sodium hydroxide, potassium hydroxide, ammonium hydroxide and the like), chelating agents (e.g., sodium edetate, sodium citrate, condensed sodium phosphate) and the like.

The eye drop formulation in the form of an aqueous suspension may also contain suspending agents (e.g., polyvinyl pyrrolidone, glycerin monostearate) and dispersing agents (e.g., surfactants such as tyloxapol and polysorbate 80, ionic polymers such as sodium alginate), in addition to the additives listed above, thereby ensuring that the eye drop formulation is a further uniform microparticulate and satisfactorily dispersed aqueous suspension.

The ophthalmic ointment may comprise a known ointment base, such as purified lanolin, petrolatum, plastibase, liquid paraffin, polyethylene glycol and the like.

Exemplary Eye Drop Formulation 1:

Formulation of siRNA compounds in PBS ("naked siRNA formulation") is typically prepared by dissolving dry siRNA in PBS. The formulation comprises at least one siRNA compound typically present in an amount ranging from about 5 µg/µl to about 60 µg/µl by volume of the composition.

In a non-limiting example formulation of an siRNA compound in PBS was prepared as follows: Under sterile conditions, 500 mg of dry siRNA were dissolved in 25 ml of sterile double distilled water (DDW), to achieve a clear 20 mg/ml solution. The solution was stored at −80° C. until use. The 20 mg/ml stock solution in DDW was then brought to a working concentration of 100 µg/3 µl, in PBS, as follows: 325 µl of 20 mg/ml stock of siRNA solution (6.5 mg) were precipitates by 0.15M NaCl and EtOH, and dried under a tissue culture laminar (sterile conditions). 6.5 mg of dry siRNA were dissolved in 130 µl PBS to form eye drop formulation 1.

Exemplary Eye Drop Formulation 2:

In some embodiments at least one siRNA compound is formulated in tris(hydroxymethyl)aminomethane (TRIS) 1M, pH 8.0 (available e.g. from Sigma (catalog #T-1503)).

In a non-limiting example 121.1 g of TRIS base (Sigma #T1503) were dissolved in 700 ml of ddH$_2$O. Desired pH 8 was achieved with addition of concentrated HCl. DDW was added to have final 1 L solution. Under sterile conditions, 42.426 mg of siRNA compound powder were dissolved in 2.1 ml of sterile double distilled water, to achieve a clear 20 mg/ml (1.5 mM) stock solution. The stock solution was stored at −80° C. until use. Under sterile conditions, corresponding amounts of siRNA stock were lyophilized and re-suspended in corresponding amount of 1M TRIS pH 8.

Exemplary Eye Drop Formulation 3:

The concentration of the viscosity-enhancing agents to be used is typically within the range of about 0.05 to about 5.0% (w/v), and more desirably, from about 0.1 to about 3.0% (w/v). One preferred ophthalmic composition comprises from about 0.01 to about 0.075% (w/v) of an active ingredient; from about 0.15 to about 2.5% (w/v) of polyoxyl 40 stearate; from about 0.1 to about 3.0% (w/v) of a cellulose thickening agent selected from 25 hydroxypropyl methylcellulose or hydroxyethylcellulose; and from about 0.0001% to about 0.01% (w/v) of an anti-oxidant selected from butylated hydroxytoluene or sodium thiosulfate.

The combination of the surfactants such as polyoxyl 40 stearate or polyoxyethylene cetyl ether or polyoxyethylene octylphenyl ether with siRNA yields an eye-drop preparation causing less irritation to the eyes, providing better distribution in the eyes and having higher stability. The inclusion of an anti-oxidant and a cellulose-thickening agent further improves the distribution of the active therapeutic agent (i.e. siRNA) in the eyes and the stability.

Other excipients may also be added, such as for example an isotonic agent, buffer, preservative, and or pH-controlling agent. Sterile purified water in appropriate amounts is present to obtain the desired eye-drop preparation.

The pH of the ophthalmic composition is within the range, which is normally used for ophthalmic preparations, as known in the art, but is desirably within the range of 5 to 8. The formulation further comprises at least one siRNA compound typically present in an amount ranging from about 6.6 µg/µl to about 50 µg/µl by volume of the composition.

Exemplary Eye Drop Formulation 4:

In the topical delivery of drugs to the lens, drug retention on the eye surface is considered to be important. Without wishing to be bound to theory, increased retention on the ocular surface leads to increased ocular absorption of a drug through the cornea into the aqueous humor and subsequently the lens.

In some embodiments a topical suspension is preferred. Non-limiting examples of topical suspensions include: (1) hydroxypropyl methylcellulose (HPMC, 0.5% w/v), (2) xanthan gum (0.5% w/v), (3) gellan gum (0.5% w/v), (4) carbopol (0.25% w/v), and (5) carbopol (0.25% w/v)-hydroxypropyl methylcellulose (HPMC) (0.25% w/v). Viscosity measurements are conducted with a viscometer.

The formulation further comprises at least one siRNA compound typically present in an amount ranging from about 5 µg/µl to about 60 µg/µl by volume of the composition.

Exemplary Eye Drop Formulation 5:

In ophthalmic compositions, a chelating agent is optionally used to enhance preservative effectiveness. Suitable chelating agents are those known in the art, and, while not intending to be limiting, edetate (EDTA) salts like edetate disodium, edetate calcium disodium, edetate sodium, edetate trisodium, and edetate dipotassium are examples of useful chelating agents. It is understood that EDTA refers to a species having four carboxylic acid functional groups, and that these carboxylic acid groups may be protonated or deprotonated (i.e. in the salt form) depending upon the pH of the composition it is in.

Buffers are commonly used to adjust the pH to a desirable range for ophthalmic use. Generally, a pH of around 5-8 is desired, however, this may need to be adjusted due to considerations such as the stability or solubility of the therapeutically active agent or other excipients.

Another commonly used excipient in ophthalmic compositions is a viscosity-enhancing, or a thickening agent. Thickening agents are used for a variety of reasons, ranging from improving the form of the formulation for convenient administration to improving the contact with the eye to improve bioavailability. The viscosity-enhancing agent comprises a polymer containing hydrophilic groups such as monosaccharides, polysaccharides, ethylene oxide groups, hydroxyl groups, carboxylic acids or other charged functional groups. While not intending to limit some examples useful viscosity-enhancing agents are sodium carboxymethylcellulose, hydroxypropylmethylcellulose, povidone, polyvinyl alcohol, and polyethylene glycol.

The formulation further comprises at least one siRNA compound typically present in an amount ranging from about 5 µg/µl to about 60 µg/µl by volume of the composition.

Exemplary Eye Drop Formulation 6 ("Formulation A"):

Formulation "A": Prepare 2 Solutions, A and B.

Preparation of Solution A: 4% solution of methylcellulose in water. 0.4 g of methylcellulose 25 (ScienceLab.com, Cat# SLM2050) dissolved in the final volume of 10 ml of apyrogenic water for injections (WFI) in 50 mL sterile tube (Norbook, Cat#7082-51). Put small sterile stirrer inside and close the cap. Keep in boiling water bath while stirring for at least 5 minutes until methylcellulose forms an opalescent solution.

Preparation of Solution B: 2% Glycerol; 0.02% (v/v) EDTA solution. Add 333.3 uL of 60% glycerol (Sigma, Cat# G6279) & 2 µl 0.5M EDTA, pH=8 (Sigma, Cat# E9884) (final—100 uM) to 9.665 ml WFI (Norbook, Cat#7082-51). Final volume—10 mL.

Prepare 2× (in regard to working concentration) solution of siRNA in Solution B. Note: if stock siRNA volume is substantially high, the final volume of Solution B is better kept lower than 10 mL to allow volume adjustment later in 2× siRNA solution.

Preparation of Working siRNA Solution:

Cool solution A in hand ~till 40-50° C. (still liquid) and mix the desired volume with an equal volume of 2× solution of siRNA in Solution B.

Final siRNA formulation contains 2% methylcellulose, 1% glycerol and 0.01% (v/v) (50 uM) EDTA in WFI. Final pH should be ~7.4 and osmomolarity—similar to human tear film. Concentration of siRNA in final formulation is 33.3 mg/ml.

Must be prepared fresh once a week and aliquoted into the portions for daily usage. The aliquots are kept at 4° C. Before application, the dose is warmed for 20-30 min at room temperature.

The final concentration of the methylcellulose is about 0.1% to about 3% w/v about 0.1% to about 2% w/v, about 0.1%-1.5% w/v methylcellulose, preferably about 2% w/v. The final concentration of glycerol is about 0.1% to about 5% v/v, about 0.5% to about 2%, preferably about 1% v/v. The final concentration of EDTA is about 0.001% to about 0.05%, about 0.005% to about 0.01%, preferably about 0.01% w/v.

Exemplary Eye Drop Formulation 7:

In some embodiments siRNA is formulated in a commercially available lubricant eye drop formulation. Non-limiting example of commercially available lubricant eye drop formulation is Systane® available from Alcon Inc. Such commercially available lubricant eye drop formulations typically comprise polyethylene glycol and/or propylene glycol, an antiseptic and/or antiviral agent such as boric acid, a gelling agent such as hydroxypropyl guar, potassium chloride and/or sodium chloride and/or magnesium chloride and/or calcium chloride and/or zinc chloride, preservatives such as Polyquad® and purified water. Under sterile conditions, 300 mg of siRNA powder is dissolved in 15 ml of sterile double distilled water, to achieve a clear 20 mg/ml solution. The solution is stored at (−)80° C. until use. The 20 mg/ml stock solution in double distilled water is then brought to a working concentration of 100 µg/3 µl, in formulation, as follows:

To obtain a final formulated quantity of 1.7 mg siRNA: 85 µl of 20 mg/ml stock of siRNA (1.7 mg), is precipitated by 0.15M NaCl and EtOH, dried under the tissue culture laminar (sterile conditions).

To achieve a siRNA solution of 33.3 mg/ml 1.7 mg dry siRNA is dissolved in 51 µL Systane®.

siRNA Compounds Induce Knockdown (KD) of Target Genes

Example 1

In Vitro Testing of siRNA Compounds

About $1.5-2\times10^5$ tested cells (HeLa cells and/or 293T cells for siRNA targeting human genes and NRK52 (normal rat kidney proximal tubule cells) cells and/or NMuMG cells (mouse mammary epithelial cell line) for siRNA targeting the rat/mouse gene) were seeded per well in 6 wells plate (70-80% confluent).

About 24 hours later, cells were transfected with siRNA compounds using the Lipofectamine™ 2000 reagent (Invitrogen) at final concentrations of 5 nM or 20 nM. The cells were incubated at 37° C. in a $CO_2$ incubator for 72 h.

As positive control for transfection phosphatase and tensin homolog (PTEN)-Cy3 labeled siRNA compounds were used. Various chemically modified blunt ended siRNA compounds having alternating modified and unmodified ribonucleotides (modified at the 2' position of the sugar residue in both the antisense and the sense strands, wherein the moiety at the 2' position is methoxy) and wherein the ribonucleotides at the 5' and 3' termini of the antisense strand are modified in their sugar residues, and the ribonucleotides at the 5' and 3' termini of the sense strand are unmodified in their sugar residues were tested. Another siRNA compound comprised a blunt ended structure having an antisense with an alternating pattern of methoxy moieties and a sense strand with three ribonucleotides linked by two 2'S' bridges at the 3' terminus; and another siRNA compound comprising antisense and sense strands having three ribonucleotides linked by 2'5' bridges at the 3' terminus was used. Some of the tested compounds comprised a blunt ended structure having an antisense with an alternating pattern of methoxy moieties and a sense strand with one or two L-nucleotides at the 3' terminal or 3' penultimate positions.

GFP siRNA compounds were used as negative control for siRNA activity. At 72 h after transfection cells were harvested and RNA was extracted from cells. Transfection efficiency was tested by fluorescent microscopy. The percent of inhibition of gene expression using specific preferred siRNA structures was determined using qPCR analysis of a target gene in cells expressing the endogenous gene.

In general, the siRNAs having specific sequences that were selected for in vitro testing were specific for human and a second species such as non-human primate, rat or rabbit genes. Similar results are obtained using siRNAs having these RNA sequences and modified as described herein.

siRNAs targeted at genes related to apoptosis and neuroprotection were tested by a similar procedure and found active and able to induce knock down of their corresponding target genes.

siRNA Prepared for Non-Invasive Administration and Administered by Eye Drops is Delivered to the Target Retinal Tissue in-vivo Example 2

Distribution of CY3-Labeled siRNA in Murine Optic Tissue (siRNA Formulated in PBS) as Monitored by Fluorescence Microscopy and Confocal Microscopy The current study showed siRNA delivery in-vivo to the lacrimal gland and ocular structures via a topical ocular route.

Abbreviations: E.D.=Eye Drops; ISH=In-situ Hybridization

The objective of this study was to test the delivery of DDIT4-Cy3 labeled siRNA (siRNA compound targeting the RTP801 gene) to the lacrimal gland via non-invasive topical ocular route. The topical ocular route has been evaluated for the delivery of siRNA into the lacrimal gland, anterior chamber of the eye, the retina and the optic nerve.

Materials and Methods

TABLE C1

Animals

| | |
|---|---|
| Species/strain: | Mice/ICR, males |
| Age: | 6-10 weeks |
| Body Weight Range: | 27-32 gr |
| Group Size: | 2 |
| Total number of animals: | 26 |

DDIT4-Cy3 siRNA (siRNA against mouse RTP801) formulated as 20 m-/ml stock solution in PBS and stored at $-80°$ C. until use.

Experimental Procedure

The study included 6 experimental groups as described in Table C2 hereinbelow: Mice were treated with a single siRNA DDIT4-Cy3 as follows:

Group V (A and B): dose regime: 50 µg/mouse/3 µl/eye, administration route: Right Eye drops (E.D.);

Group Am-V-A, Am3-VIII, Am3-IX: dose regime: 50 µg/mouse/3 µl/eye, administration route: both eyes, Eye drops (E.D.);

Group VI-A: dose regime: 20 µg/mouse/3 µl/eye, administration route: Right eye, Eye drops (E.D.);

Group VII, Am-VII: non-treated control.

TABLE C2

Study Design

| Group | SiRNA Type | Dose µg/mouse | Injected Volume (µl) | Route | Time point (hrs) | Group Size |
|---|---|---|---|---|---|---|
| V-A | DDIT4-Cy3 | 50.00 Right Eye | 3.00 | E.D. | 1 | 2 |
| Am-V-A | DDIT4-Cy3 | 50.00 per eye/ Both Eyes | 3.00 | E.D. | 1 | 2 |
| V-B | DDIT4-Cy3 | 50.00 Right Eye | 3.00 | E.D. | 4 | 2 |
| VI-A | DDIT4-Cy3 | 20.00 Right Eye | 3.00 | E.D. | 1 | 2 |
| VII | None | none | None | none | | 5 |
| Am-VII | None | none | None | none | | 1 |
| Am3-VIII | DDIT4-Cy3 | 50.00 per eye/ Both Eyes | 3.00 | E.D. | 4 | 2 |
| Am3-IX | DDIT4-Cy3 | 50.00 per eye/ Both Eyes | 3.00 | E.D. | 24 | 2 |

The siRNA doses were prepared under sterile conditions. siRNA aliquots were thawed for at least 30 min at room temperature prior to administration. Total amount per aliquot (per each mouse) included an additional 20% of the calculated volume. The designated siRNA dose was delivered in 3 µl (Experimental groups V-VI) volume per eye.

Anesthesia: Mice were anesthetized with Ketamine/Xylazine mix as follows: 0.85 ml Ketamine+0.15 ml Xylazine+0.9 ml Saline, 0.1 ml mix solution/20 gr body weight (BW).

Eye drop (E.D.) delivery: A 3 µl sample volume was slowly dropped in the treated eye (corneal surface) using a blunt pipette tip; the animals were placed in a warm environment to prevent anesthesia-induced hypothermia, and were returned to cages after regaining consciousness.

Scheduled euthanasia: Following treatment, mice from all groups were euthanized according to the study design (Table C2, Time point termination).

Termination step was accomplished by cardiac puncture and blood collection; collected serum/plasma was stored ($-20°$ C.) for further siRNA blood detection analysis.

Tissue Collection: Left and right eyes including optic nerve, lacrimal glands (left and right) from all animals were excised, brain (front and middle parts of the brain, frontal oriented sections) from animals of groups, V-A one from group VII, Am3-VIII, Am3-IX were excised, embedded in optimal cutting temperature (OCT) compound and sectioned with a cryostat into 8 µm slices that were placed on microscope slides (Superfrost/Plus™). Sections were fixed in 95% EtOH for 7 minutes then counter stained with DAPI (1 µg/ml), incubated for 1 minute in absolute EtOH, incubated for 5 minutes in xylene, air dried and mounted.

Tissue Evaluation: Delivery of siRNA was evaluated using light microscopy and digital imaging. A tissue fragment was considered positive (i.e., successful Cy3 DDIT4 siRNA intracellular incorporation) only where histological (microscopic) examination showed a clear fluorescence signal within specific cells or structures such as acinar alone or in combination with ductal cells of the lacrimal gland. Background DAPI staining assisted in identification of tissue structure: in the case of anterior eye chamber structures such as cornea, angle, ciliary body or posterior eye chamber such as retina (retinal pigmentum epithelium cells (RPE), retinal ganglion cells (RGC)). Delivery was considered positive if histological examination would show that all animals within one experimental group showed the same fluorescence signal within the investigated cell type/tissue. (i.e. time points or route administration).

Results & Discussion

All cryosections were analyzed under light microscopy (bright field, BF) and fluorescence confocal microscopy. The fluorescent signal was visualized in the following tissues:

Retina by E.D. Delivery (Retinal Pigment Epithelial Cells, Retinal Ganglion Cells)

FIGS. 1A-1B: Representative images of Cy3 labeled DDIT4 siRNA incorporated into mice retina.

FIG. 1A: Fluorescent microscopy (upper panel, magnification ×40) of the retina 1 hour after E.D. administration. Right arrow identifies Cy3 stained retinal ganglion cells (RGC), left arrow identifies Cy3 stained retinal pigmentum epithelium cells (RPE). Confocal microscopy (lower panel, magnification ×60) of the retinal ganglion cells layer. The lower set of 9 views show Cy3 labeled tissue (Left), bright filed (BF, center) and a merge of the two (M, right). Arrows point to the labeled RGCs.

Figures in 1B: Confocal microscopy of the retina 4 hours after E.D. administration (upper ×40, lower ×60). Cy3 staining of the RGC is prominent.

Eye Drop Delivery of siRNA to the Lacrimal Glands (Acinar Cells, Ductal Cells)

FIGS. 2A-2D: Representative images of Cy3 labeled DDIT4 siRNA incorporated into ductal and acinar cells of the murine lacrimal gland.

Figure 2A:
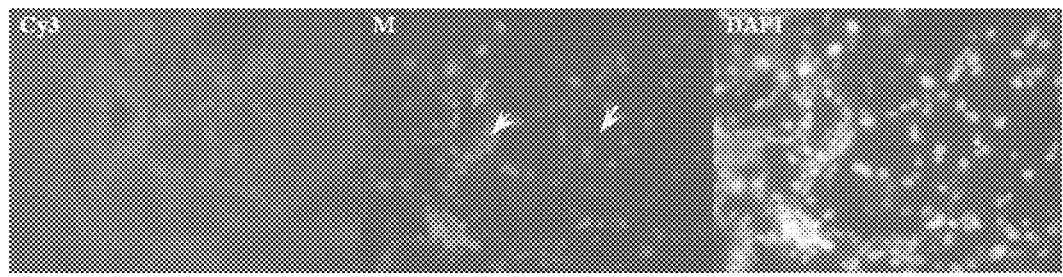
FIGS. 2A-2D: Representative images of Cy3 labeled DDIT4 siRNA incorporated into ductal and acinar cells of the murine lacrimal gland following eye drop administration.

FIG. 2A: Fluorescent microscopy of the lacrimal gland 1 hour after E.D. administration (M=merged DAPI-Cy3 staining). Center arrow points to acinar cells, right arrow indicates ductal epithelial cells, the gray left arrow points to the lacrimal duct (magnification ×60)

Figure 2B:
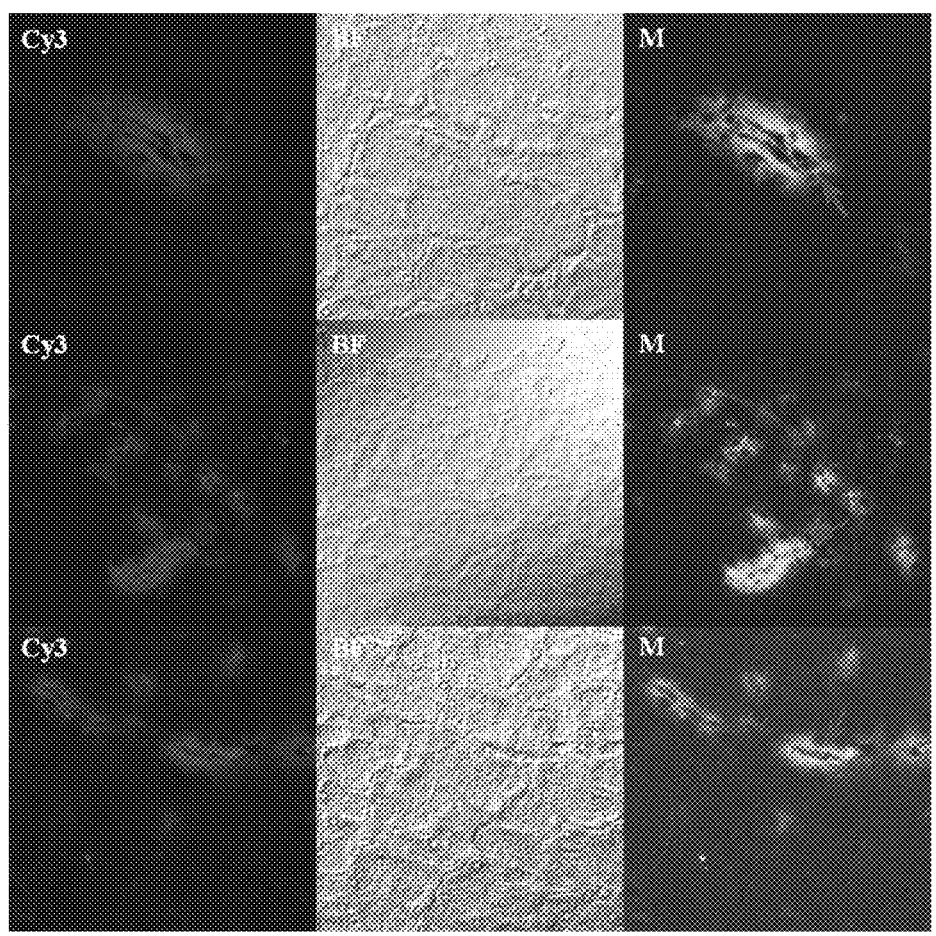

FIG. 2B: Confocal microscopy of the lacrimal gland 1 hour after E.D administration (upper ×40 and lower panel ×60). Arrow in merged image M is pointing to lacrimal duct.

Figure 2C:
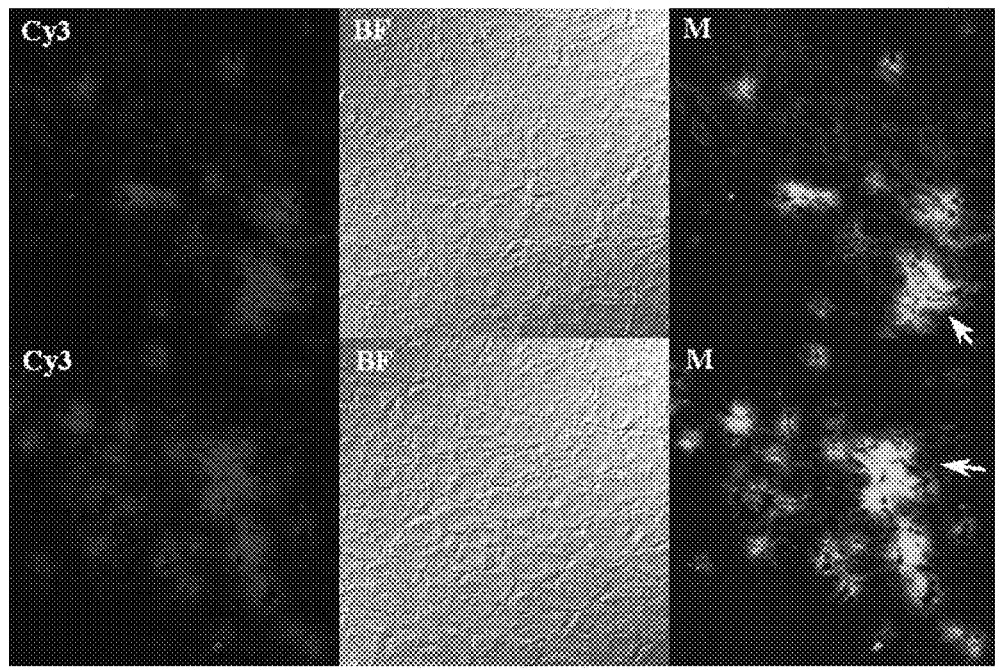
Figure 2D:
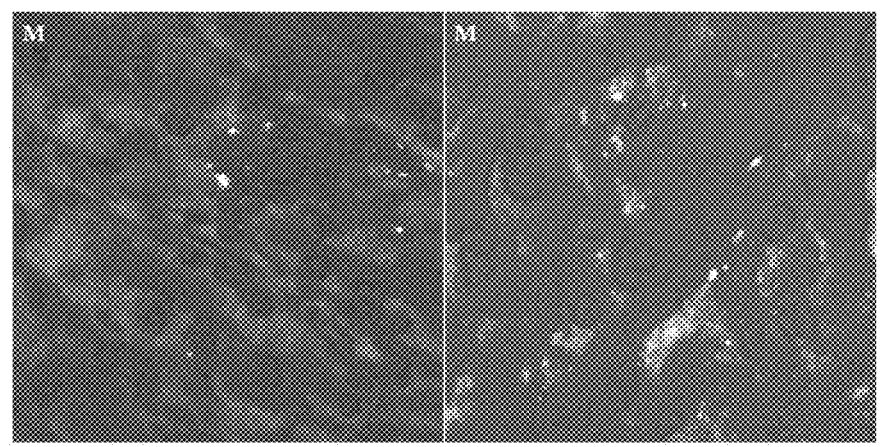

FIG. 2C: Confocal microscopy of the lacrimal gland 1 hour E.D administration (×40). Arrows are pointing to acinar cells FIG. 2D: Confocal microscopy of the lacrimal gland 4 hours after E.D. (×60).

FIGS. 3A-3C show time course of accumulation of Cy3-siRNA in rat choroid after administration by eye drops, following 1 and 4 hours post administration. Choroid, outer nuclear layer, RPE and outer segment layer of photoreceptor cells show Cy3 staining.

Figure 4:
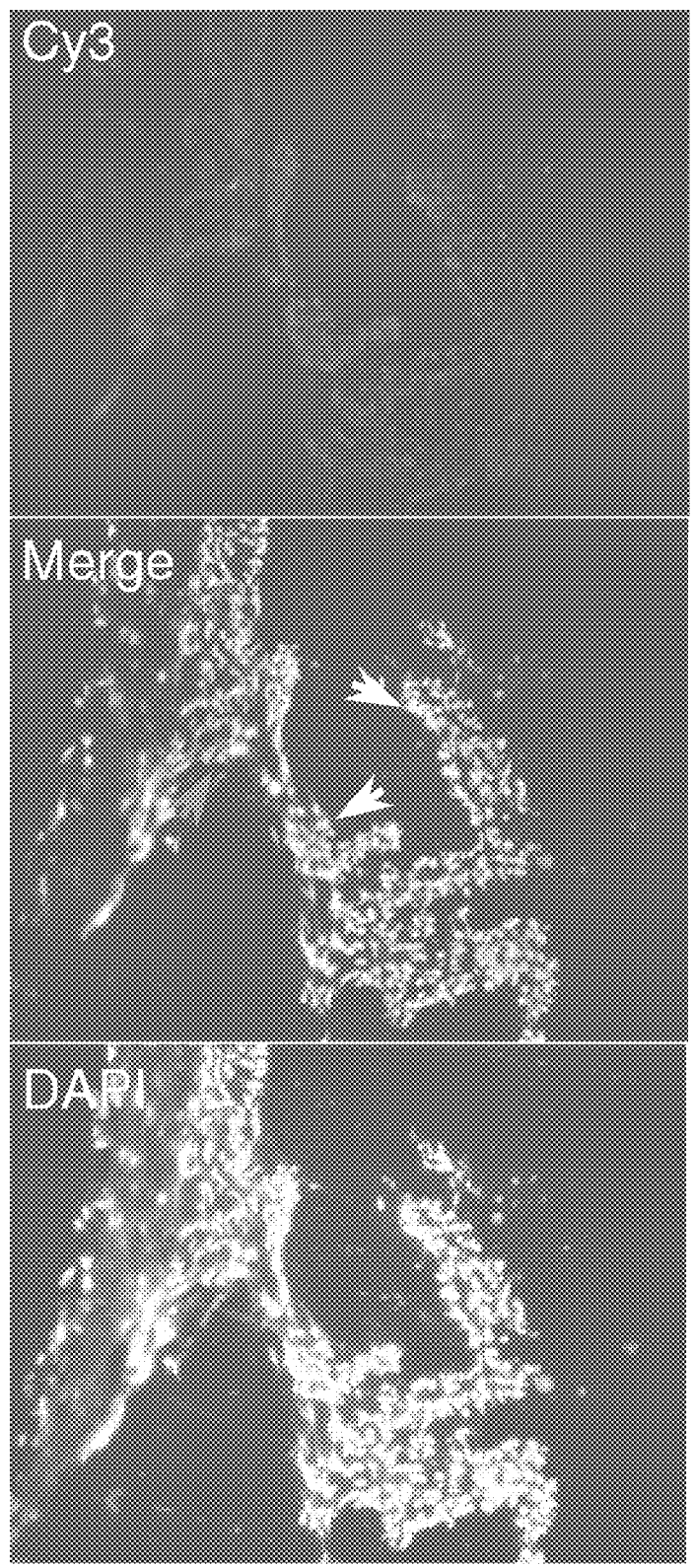
FIG. 4: Cy3-siRNA delivery to the trabecular meshwork and ciliary body one hour after eye drop administration to the eye.

FIG. 4 shows Cy3-siRNA delivery to the trabecular meshwork end ciliary body one hour after administration by eye drops.

Different chemically modified siRNA (structural motives) were tested with mouse Cy3-labeled siRNA. Similar tissue distribution to that shown above was observed for all structures tested: Structure B having alternating natural ribonucleotides and 2'O-Me sugar modified ribonucleotides on both strands; Structure I having alternating natural ribonucleotides and 2'O-Me sugar modified ribonucleotides on the antisense strand and three ribonucleotides linked by 2'5' internucleotide linkages at the 3' end of the sense strand; and a structure having three ribonucleotides linked by 2'5' internucleotide linkages at the 3' end of each of the antisense and sense strands.

Example 3

Examination of Topical Ocular Route Delivery of Formulated siRNA in Rats (siRNA Formulated in PBS or in Methyl Cellulose 2% ("Formulation A"))

In the current study the ocular delivery of DDIT4-Cy3 siRNA formulated either in PBS or in Formulation A and applied by Eye Drops was studied in rats.

Experimental Design:
1) Group I, II, III, IV, V: dose regime: siRNA formulated in Formulation A; 100 μg/rat/3 μl/eye, administration route: Bilateral Eye drops (E.D.);
2) Group Ia, IIa, IIIa, IVa, Va: dose regime: siRNA formulated in PBS; 100 μg/rat/3 μl/eye, administration route: Bilateral Eye drops (E.D.);
3) Group VI: control group treated with the formulation vehicle of Formulation A (no siRNA); 100 μg/rat/3 μl/eye, administration route: Bilateral Eye drops (E.D.);
4) Group VII: intact control The siRNA doses were prepared under sterile conditions. siRNA aliquots were thawed for at least 30 minutes at room temperature prior to administration. Total amount per aliquot (per each mouse) included an additional 20% of the calculated volume. The designated siRNA dose was delivered in 3 μl volume per eye.

Anesthesia: Rats from groups I-VII were anesthetized with Equithesine (4 ml/kg)

Termination step: At study termination, animals were deeply anesthetized by Equithesine (4 ml/kg). Thereafter, rats were intracortically perfused with fresh 10% neutral buffered formalin using peristaltic pump standard regime.

Tissue Collection: Left and right eyes including optic nerve from all animals were enucleated, perforated and post fixed in 10% neutral buffered formalin for an additional 1 hour in room temperature with slow rotation, cryoprotected stepwise by sucrose gradient at 4° C. overnight, following cryoprotection in optimal cutting temperature (OCT) compound at 4° C. overnight with rotation, embedded in OCT compound and sectioned with a cryostat into 12 μm slices that were placed on microscope slides (Superfrost/Plus). Sections were counter stained with DAPI (1 μg/ml) and mounted.

Delivery of siRNA was evaluated using light microscopy and digital imaging. A tissue fragment was considered positive (i.e., a successful Cy3 DDIT4__1 siRNA transfer in anterior eye chamber, retina and optic nerve delivery was considered positive) if histological examination would show that all animals within one experimental group showed the same fluorescent signal within the specific tissue/cell type.

Results: All cryosections were analyzed under light microscopy (bright field, BF) and fluorescence confocal microscopy. The fluorescent signal was visualized in retinal pigment epithelial cells and retinal ganglion cells. Notably, compounds formulated in PBS reached maximum distribu-

TABLE C3

Study Design

| Group | siRNA | Dose μg/eye | Route of Adm. (Bilateral) | Adm. Volume (μl) | Formulation | Termination time | Group Size |
|---|---|---|---|---|---|---|---|
| I | DDIT4__1-Cy3 | 100.00 | E.D. | 3.00 | Formulated | 30 min. | 1 |
| Ia | DDIT4__1-Cy3 | 100.00 | E.D. | 3.00 | PBS | 30 min. | 1 |
| II | DDIT4__1-Cy3 | 100.00 | E.D. | 3.00 | Formulated | 1 hour | 1 |
| IIa | DDIT4__1-Cy3 | 100.00 | E.D. | 3.00 | PBS | 1 hour | 1 |
| III | DDIT4__1-Cy3 | 100.00 | E.D. | 3.00 | Formulated | 3 hours | 1 |
| IIIa | DDIT4__1-Cy3 | 100.00 | E.D. | 3.00 | PBS | 3 hours | 1 |
| IV | DDIT4__1-Cy3 | 100.00 | E.D. | 3.00 | Formulated | 6 hours | 1 |
| Iva | DDIT4__1-Cy3 | 100.00 | E.D. | 3.00 | PBS | 6 hours | 1 |
| V | DDIT4__1-Cy3 | 100.00 | E.D. | 3.00 | Formulated | 24 hours | 1 |
| Va | DDIT4__1-Cy3 | 100.00 | E.D. | 3.00 | PBS | 24 hours | 1 |
| VI | N/A | N/A | E.D. | 3.00 | vehicle | 1 hours | 1 |
| VII | N/A Intact control | N/A | N/A | N/A | N/A | N/A | 1 | tion in ocular tissues 3 hours after administration, and were cleared from said tissues at the 6 hour time point. However, compounds formulated in Formulation A were maximally distributed in ocular tissues at 24 hours after administration.

Example 4

Ocular Distribution of siRNA (Formulated in PBS) in the Cynomolgus Monkey

TABLE C4

Experimental Design

| Group | Animal number | Compound | Dose Volume | Termination after administration | Processing at termination Eyes |
|---|---|---|---|---|---|
| 1 | 101 | Cy3-DDIT4_1 | 500 ug/20 ul/eye | 1 hour | 4% PFA |
| 2 | 251 | DDIT4_1 | 500 ug/20 ul/eye | 1 hour | Snap frozen in liquid nitrogen |
| 3 | 351 | Cy3-DDIT4_1 | 500 ug/20 ul/eye | 5 hours | 4% PFA |
| 4 | 401 | DDIT4_1 | 500 ug/20 ul/eye | 5 hours | Snap frozen in liquid nitrogen |

ED = Eye Drops, topically

The aim of this study was to investigate the tissue distribution of siRNA formulated in PBS following single topical ocular administration to the surface of the eye of the Cynomolgus *Macaca fascicularis* monkey. All tissues were snap frozen in triplicate ~1 to ~2 g samples or as a whole, as appropriate.

RNA Purification

Frozen samples were grinded to a fine powder under liquid nitrogen. A small amount of the powdered tissue was used for RNA extraction. The rest of the tissues were stored at −80° C. for further usage. PolyA RNA was extracted from each sample with MicroPoly(A)Purist mRNA purification Kit (#1919) and processed according to manufacturer's protocol for poly(A)RNA isolation from tissues or cells. The final yields and spectral characteristics of the RNA are summarized below in Table C5.

TABLE C5 polyA RNA from monkey

| Tissue | 260/280 | 260/230 | Concentration µg/µl | Yield µg |
|---|---|---|---|---|
| Lymph Node | 1.58 | 0.92 | 0.104 | 1.55 |
| Spleen | 1.74 | 1.27 | 0.175 | 2.62 |

One µg from the spleen and 0.7 µg from the lymph node polyA RNA preparations were used for cDNA synthesis using random primer. Casp2 gene was successfully amplified from both cDNA preparations Results are summarized below in Table C6.

TABLE C6

| | Results | | | | |
|---|---|---|---|---|---|
| Treatment | Tissue analysed | Termination | Av | SD | Group size |
| ED(REDD14) | Neuronal Retina | 1 h | 0.2 | [+/−0] | 1 (2 eyes) |
| ED(REDD14) | Neuronal Retina | 5 h | 0.05 | [+/−0.03] | 1 (2 eyes) |
| ED(REDD14) | RPE | 1 h | 0.62 | [+/−0.05] | 1 (2 eyes) |
| ED(REDD14) | RPE | 5 h | 0.1 | [+/−0.07] | 1 (2 eyes) |
| ED(REDD14) | optic nerve | 1 h | 8.9 | [+/−2.6] | 1 (2 eyes) |
| ED(REDD14): | optic nerve | 5 h | 3 | [+/−1.9] | 1 (2 eyes) |

Conclusion: SiRNA formulated in PBS following single topical ocular administration to the surface of the eye of the Cynomolgus *Macaca fascicularis* monkey reaches the neuronal retina and can be measured by the qPCR S&L method.

Example 5

Delivery of siRNA (Formulated in TRIS) to Target Retinal Tissue in Mice

Examination of topical delivery of siRNA molecules labeled with different fluorophores.

Topical delivery to Mice of 20 ug of different fluorescently-labeled siRNAs formulated in tris(hydroxymethyl) aminomethane (TRIS) 1M, pH 8, 1 hr post-administration.

siRNAs tested:

Cy3-QM5; Cy3-DDIT4; Cy3.5-DDIT4; DDIT4_1 Dy-649/C6; FITC-CNL_1; 3'Cy3-CNL_1; Cy3-Casp2_4 L-DNA; Cy3-AS-Casp2_4; TGASEII-FAM; HNOEL-FAM. (QM5 is a rat/mouse siRNA that targets p53; CNL is control scrambled siRNA)

Exemplary chemically modified Casp2 siRNA compounds were as follows:

1. Sense: GCCAGAAUGUGGAACUC2pC2pU, 17 and 18 are 2'-5'-bridge

Antisense: mAGmGAmGUmUCmCAmCAmUUm-CUmGGmC-cy3

2. Sense: GCCAGAAUGUGGAACUC; LdC; LdT 18 and 19 are L-DNA

Antisense: mAGmGAmGUmUCmCAmCAmUUm-CUmGGmC-cy3

3. Sense: GCCAGAAUGUGGAACUC; LdC; U18 is an L-DNA moiety

Antisense: mAGmGAmGUmUCmCAmCAmUUm-CUmGGmC-cy3

LdC, LdT refer to L-DNA nucleotides, mA, mC, Mg, Mu refer to 2'O-methoxy ribonucleotides.

Formulated (formulated compound): siRNA in 1M Tris pH 8.0 Of the following siRNA's: QM5-Cy3#1, QM5-Cy3#10, DDIT4_1-Cy3, DDIT4_1Cy3.5, Redd14(DDIT4_1) Dy-649/C6, FITC-CNL_1 RD/CNL_1FD, scrambled3'Cy3CNL 1, Cy3-AS-CASP2_4-Struc-L-DNA-s (2 residues at 3' of sense)-plus-alt AS, Cy3AS-CASP2_4-Struc2-5-s (2 residues at 3' of sense)-plus-alt AS, TGASEII-FAM, HNOEL-FAM.

TABLE C7

Formulations

| siRNA | IDO | Final | siRNA Stock | Preparation |
|---|---|---|---|---|
| QM5-Cy3#1 | 116937 | 40 μg | 20 mg/ml | 2 μl stock were lyophilized and resuspended in 7 μl 1M Tris pH 8 |
| QM5-Cy3#10 | 116938 | 40 μg | 20 mg/ml | 2 μl stock were lyophilized and resuspended in 7 μl 1M Tris pH 8 |
| DDIT4_1-Cy3 | 117821 | 40 μg | 20 mg/ml | 2 ul stock were lyophilized and resuspended in 7 μl 1M Tris pH 8 |
| DDIT4_1-Cy3.5 | 112206 | 40 μg | 20 mg/ml | 2 ul stock were lyophilized and resuspended in 7 μl 1M Tris pH 8 |
| Redd14(DDIT4_1) Dy-649/C6 | 114029 | 40 μg | 20 mg/ml | 2 μl stock were lyophilized and resuspended in 7 μl 1M Tris pH 8 |
| FITC-CNL_1RD/CNL_1 FD | 110357 | 40 μg | 20 mg/ml | 2 μl stock were lyophilized and resuspended in 7 μl 1M Tris pH 8 |
| scarmbled3'Cy3-CNL_1 | 110910 | 40 μg | 20 mg/ml | 2 μl stock were lyophilized and resuspended in 7 μl 1M Tris pH 8 |
| Cy3-AS-CASP2_4-Struc-L-DNA-s(2 residues at 3' of sense)-plus-alt AS | 122994 | 40 μg | 20 mg/ml | 2 μl stock were lyophilized and resuspended in 7 μl 1M Tris pH 8 |
| Cy3-AS-CASP2_4-Struc2-5-s(2 residues at 3' of sense)-plus-alt AS | 122979 | 40 μg | 20 mg/ml | 2 μl stock were lyophilized and resuspended in 7 μl 1M Tris pH 8 |
| TGASEII-FAM | 75755 | 11.62 μg | 0.75 μg/μl | 15.5 μl stock were lyophilized and resuspended in 2 μl 1M Tris pH 8 |
| HNOEL-FAM | 75757 | 4.48 μg | 1.4 μg/μl | 3.2 μl stock were lyophilized and resuspended in 0.784 μl 1M Tris pH 8 |
| DDIT4_1-Cy3 | 117821 | 40 μg | 20 mg/ml | 2 μl stock + 0.7 ul PBSx 120 + 4.3 μl DDW |

Description of the test material: Under sterile conditions, corresponding amount of siRNA stock were lyophilized and re-suspended in corresponding amount of 1M Tris pH8 (see Table C7).

Quantity supplied: One vile for each tested siRNA (Synthesized by Biospring, AG)

Storage Conditions: frozen until use. Prior to use, samples were thawed and kept at room temperature for 30 minutes.

Control Article(S)

Positive Control—DDIT4_1-Cy3 in PBS, Batch #: 117821

Description of the test material: Under sterile conditions, 42.426 mg of DDIT4_1-Cy3 powder (BioSpring) were dissolved in 2.1 ml of sterile double distilled water, to achieve a clear 20 mg/ml (1.5 mM) solution. The solution was stored at −80° C. until use.

Vehicle—1M Tris pH 8.0—Outsourcing from Sigma (catalog #T-1503). 121.1 g of TRIS base (Sigma # T1503) were dissolved in 700 ml of ddH$_2$O. Desire pH 8 was achieved with concentrated HCl. DDW was added to have final 1 L solution.

Vehicle—PBSX10—Outsourcing from Biological Industries (catalog #02-023-5A; (For 10×PBS) Batch #:619113)

Test System

Animals:
Species: Mice; Strain: RTP-801WT; CMF-608WT
Source: Harlan Laboratories, Jerusalem, Israel.
Age: 8-12 weeks; Body Weight Range: 17-28 gr
Sex: males; Group Size: 1; Total number of animals: 14
Animal Husbandry: Diet: Animals were provided an ad libitum commercial rodent diet and free access to drinking water. Environment: (i) Acclimatization of at least 5 days. (ii) All the animals were confined in a limited access facility with environmentally-controlled housing conditions throughout the entire study period, and maintained in accordance with approved standard operating procedures (SOPs).

Experimental Design

General: The study included 14 experimental groups as described in Table C8:

Experimental groups 1-12 siRNA delivered by eye drops, group 13 the vehicle [TRIS 1M pH8 treated control delivered by eye drops and group 14 (non-treated control). Mice were treated with a single siRNA as follows:

Groups 1-9 and 12: dose regime: 20 μg/eye/3 μl/SiRNA, group 10: dose regime 5.81 μg/eye/3 μl/siRNA, group 11: dose regime 2.24 μg/eye/3 μl/siRNA administration route: Eye Drop (E.D.);
Group 13: vehicle (TRIS 1M pH8) 3 μl/eye control
Group 14: none treated control

TABLE C8

Study Design

| Group | SiRNA type/bilateral | Dose μg/eye | Volume (μl) | Route | Time point (hrs) | Group Size |
|---|---|---|---|---|---|---|
| 1 | QM5-Cy3#1 | 20 | 3.00 | E.D. | 1 | 1 |
| 2 | QM5-Cy3#10 | 20 | 3.00 | E.D. | 1 | 1 |
| 3 | DDIT4_1-Cy3 | 20 | 3.00 | E.D. | 1 | 1 |
| 4 | DDIT4_1-Cy3.5 | 20 | 3.00 | E.D. | 1 | 1 |

TABLE C8-continued

Study Design

| Group | SiRNA type/bilateral | Dose μg/eye | Volume (μl) | Route | Time point (hrs) | Group Size |
|---|---|---|---|---|---|---|
| 5 | DDIT4__1 Dy-649/C6 | 20 | 3.00 | E.D. | 1 | 1 |
| 6 | FITC-CNL__1RD/CNL__1FD | 20 | 3.00 | E.D. | 1 | 1 |
| 7 | scarmbled3'cy3-CNL__1 | 20 | 3.00 | E.D. | 1 | 1 |
| 8 | Cy3-AS-CASP2__4-Struc-L-DNA-s(2 residues at 3' of sense)-plus-alt AS | 20 | 3.00 | E.D. | 1 | 1 |
| 9 | CY3-AS-CASP2__4-Struc2-5-s(2 residues at 3' of sense)-plus-alt AS | 20 | 3.00 | E.D. | 1 | 1 |
| 10 | TGASEII-FAM | 5.81 | 3.00 | E.D. | 1 | 1 |
| 11 | HNOEL-FAM | 2.24 | 3.00 | E.D. | 1 | 1 |
| 12 | DDIT4__1-Cy3 in PBS vehicle (positive control) | 20 | 3.00 | E.D. | 1 | 1 |
| 13 | Vehicle (TRIS 1M pH 8) (negative control) | N/A | 3.00 | E.D. | 1 | 1 |
| 14 | Non treated (negative control) | N/A | 3.00 | E.D. | 1 | 1 |

The siRNA doses for delivery were prepared under sterile conditions and stored at −20° C. siRNA aliquots were thawed for at least 30 minutes at room temperature prior to administration. Total amount per aliquot (per each eye) included an additional 20% of the calculated volume. The designated siRNA dose was delivered in 3.5 μl (Experimental groups 1 to 9 and 12) volume per eye. The designated siRNA dose was delivered in 3.4 μl (Experimental groups 10 and 11) volume per eye.

Anesthesia: Mice were anesthetized with Ketamine/Xylazine mixture as follows (0.85 ml Ketamine+0.15 ml Xylazine+0.9 ml Saline, 0.1 ml mix solution/20 gr BW).

Eye drop delivery: A 3 μl volume sample was slowly dropped in each eye (corneal surface) by blunt pipette tip; the animals were placed in a warm environment to prevent anesthesia-induced hypothermia, and were returned to its cage after it regaining consciousness.

Scheduled euthanasia: Mice from all groups were terminated according to the study design (Table C8, Time points termination).

Termination step was accomplished by cervical dislocation.

Tissue Collection: Left and right eyes including optic nerve, from all animals were enucleated, the retina was transversal dissected with the blade, the lens/vitreous were gently removed. The remaining eye cup was fixed with 4% PFA (in PBS pH 7.4) for 30 minutes, then infiltrated with 30% sucrose for 3 hours at 4° C. Washed 3×5 minutes with ice cold PBS pH7.4. It was then embedded in optimal cutting temperature (OCT) compound and sectioned longitudinal with a cryostat into 4 μm slices that were placed on microscope slides (Superfrost/Plus). Sections were counter stained with DAPI (1 μg/ml) and mounted.

A whole blood drop from all animals, was smeared on the slide with the cover slip, and covered. It was then glued with nail polish Evaluation Delivery of siRNA was evaluated using light microscopy and digital imaging. A tissue fragment was considered positive (i.e., a successful siRNA transfer\ intracellular incorporation occurred) only if histological (microscopic) examination showed clear fluorescence signal within specific cells or structures of the anterior or posterior chamber, and retina. Background DAPI staining was assisted in identification of tissue structure. Delivery was considered positive if histological examination was consistent within the group (bilateral identical cell type or structural staining), i.e. the histological examination would show the same fluorescent signal in all cell types/tissues (anterior eye chamber, retina and optic nerve) of the same experimental group.

Results

Figure 5A:
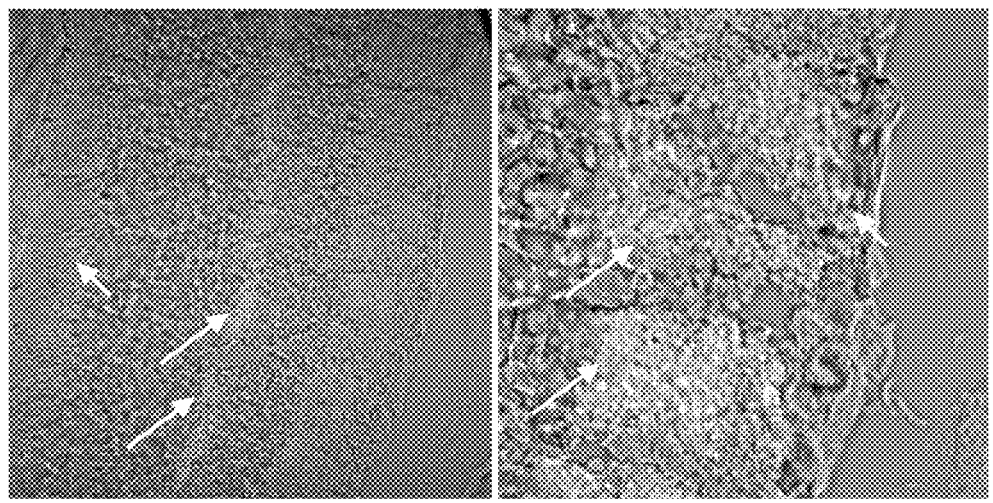
FIGS. 5A-5B: Confocal microscopy (magnification ×60) of the retina 1 hour after eye drop administration of QM5—siRNA targeted at the p53 gene. SiRNA in retina (retinal pigment epithelial cells, retinal ganglion cells) is shown by Cy3 fluorescence.
Figure 5B:
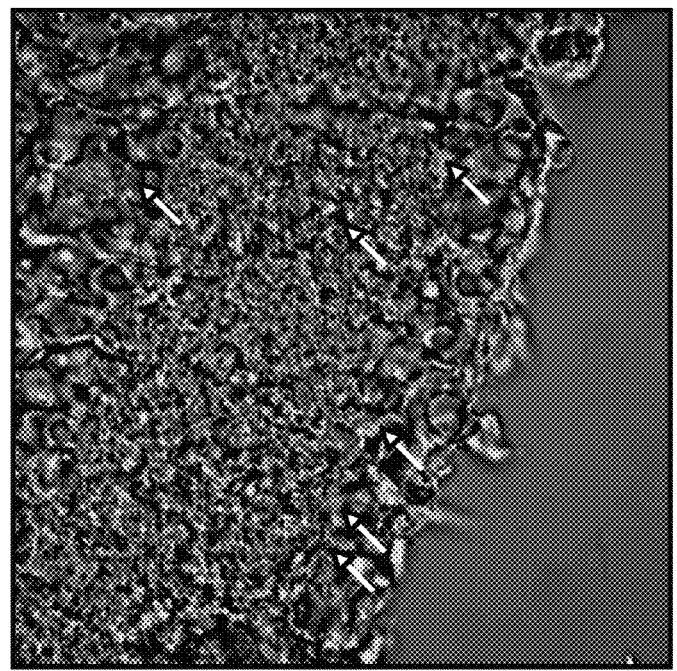

FIGS. 5A-5B: Confocal microscopy (magnification ×60) of the retina 1 hour after eye drop administration of QM5—siRNA targeted at the p53 gene. SiRNA in retina (retinal pigment epithelial cells, retinal ganglion cells) is shown by Cy3 fluorescence.

Figure 6A:
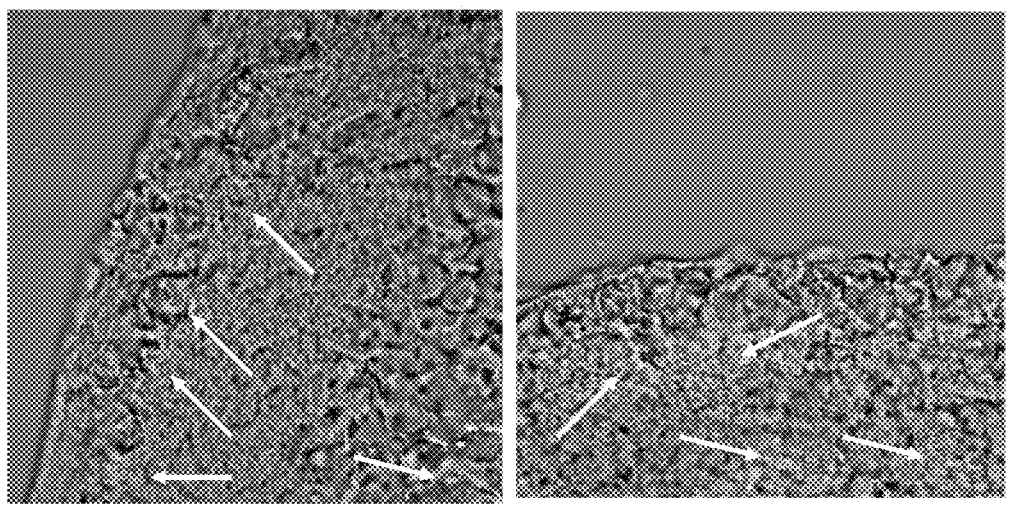
FIGS. 6A-6B are representative images of Cy3 labeled DDIT4 siRNA incorporated into mice retina.
Figure 6B:
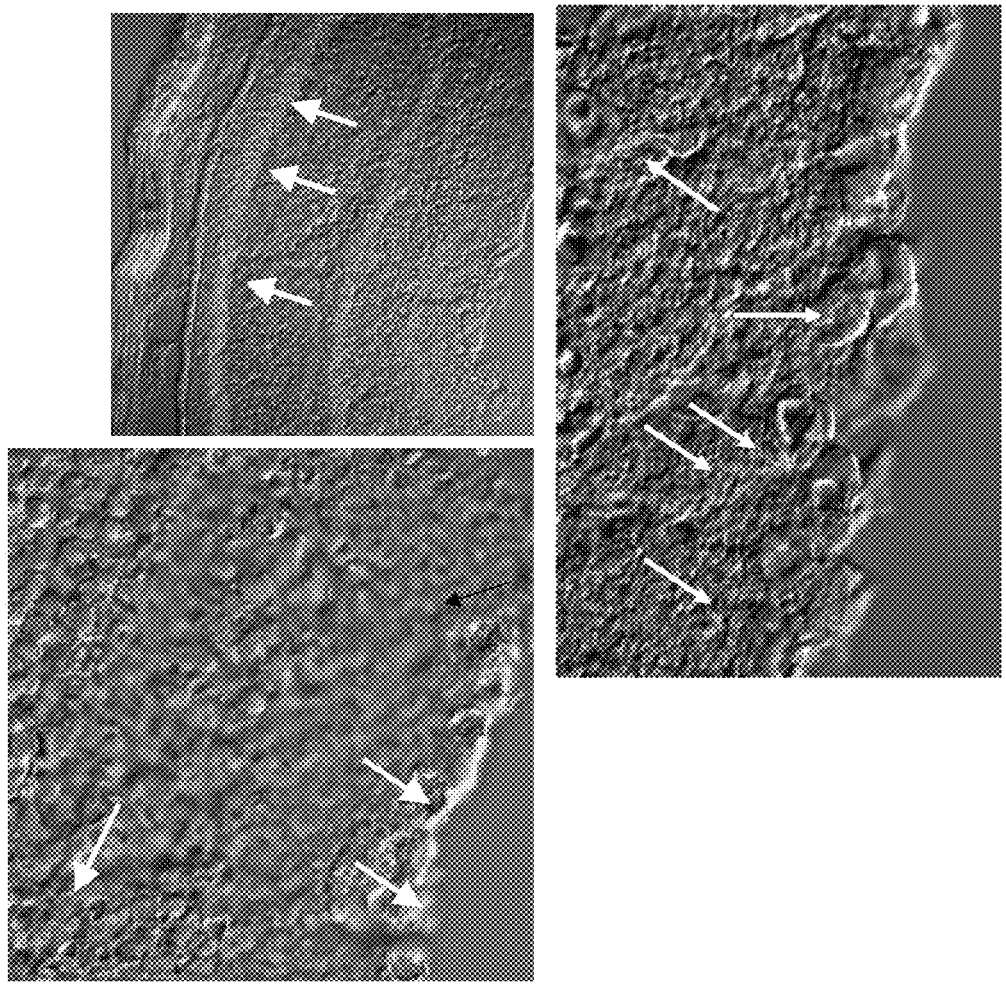

FIGS. 6A-6B are representative images of Cy3 labeled DDIT4 siRNA incorporated into mice retina.

FIG. 6B shows accumulation of DDIT4__1 Cy3-siRNA 1 hour post administration by eye drops. Choroid, outer nuclear layer, RPE and outer segment layer of photoreceptor cells show Cy3 staining.

Figure 7:
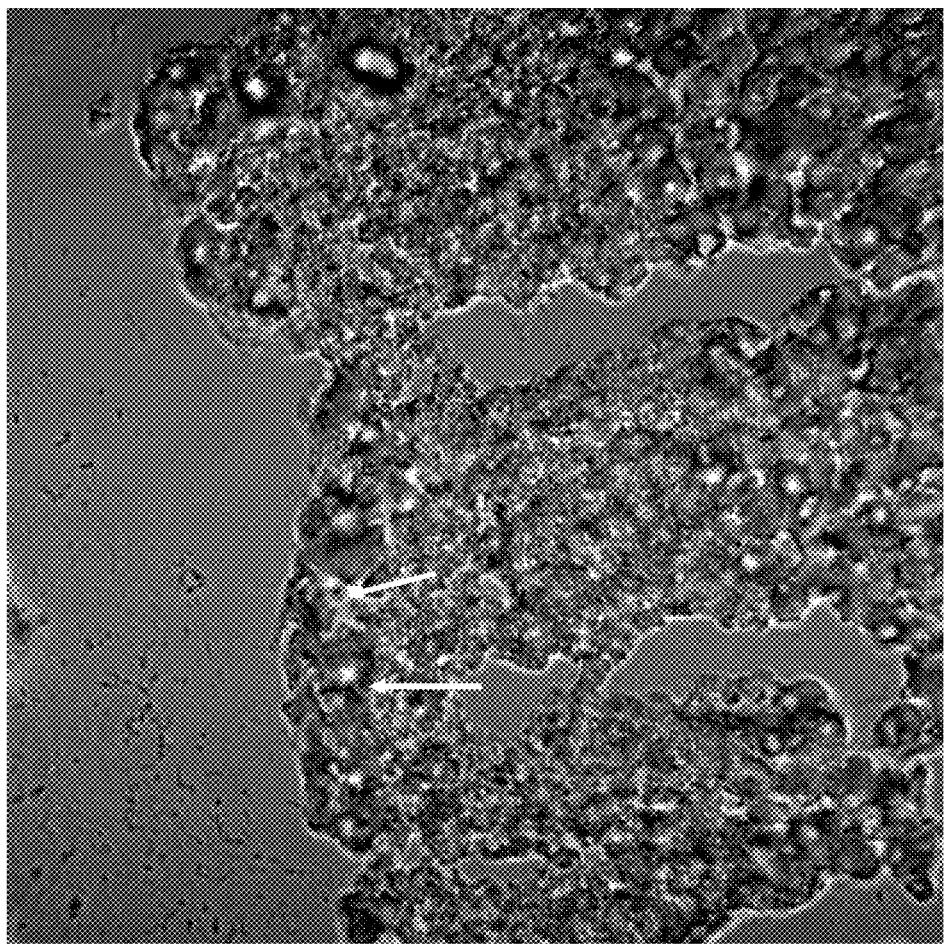
FIG. 7 shows accumulation of DDIT4_1 Dy-649/C6-siRNA 1 hour post administration by eye drops in RGC cells by use of Dy-649/C6 staining.

FIG. 7 shows accumulation of DDIT4__1 Dy-649/C6-siRNA 1 hour post administration by eye drops in RGC cells by use of Dy-649/C6 staining.

Figure 8A:
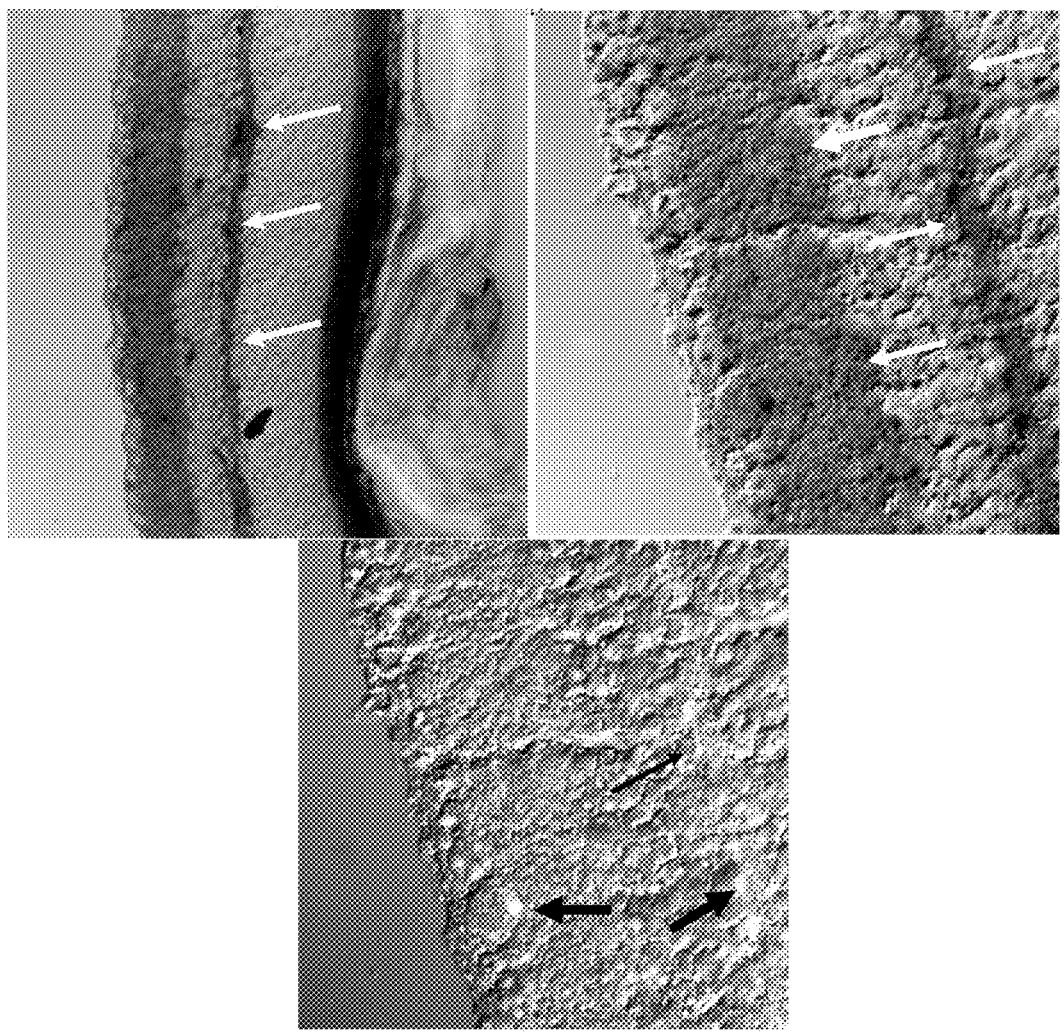
FIG. 8A-8C represent control siRNA FITC-CNL_1RD/CNL_1FD and scarmbled3' cy3-CNL_1 delivery to retinal tissues by different staining methods.
Figure 8B:
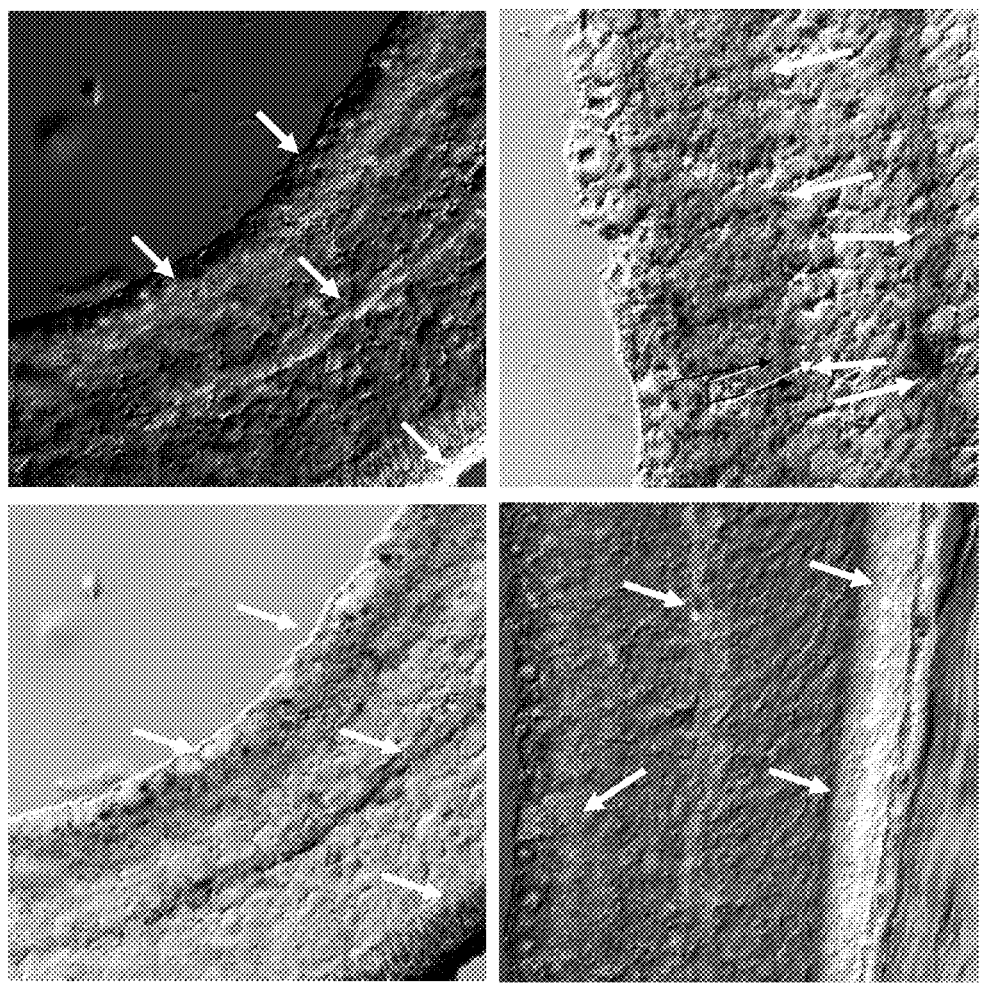
Figure 8C:
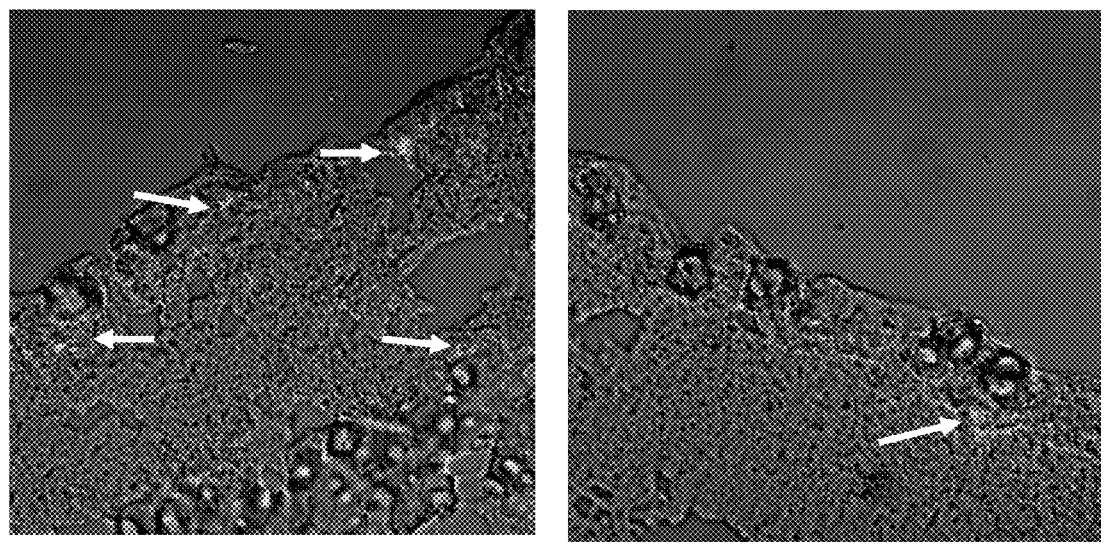
Figure 9A:
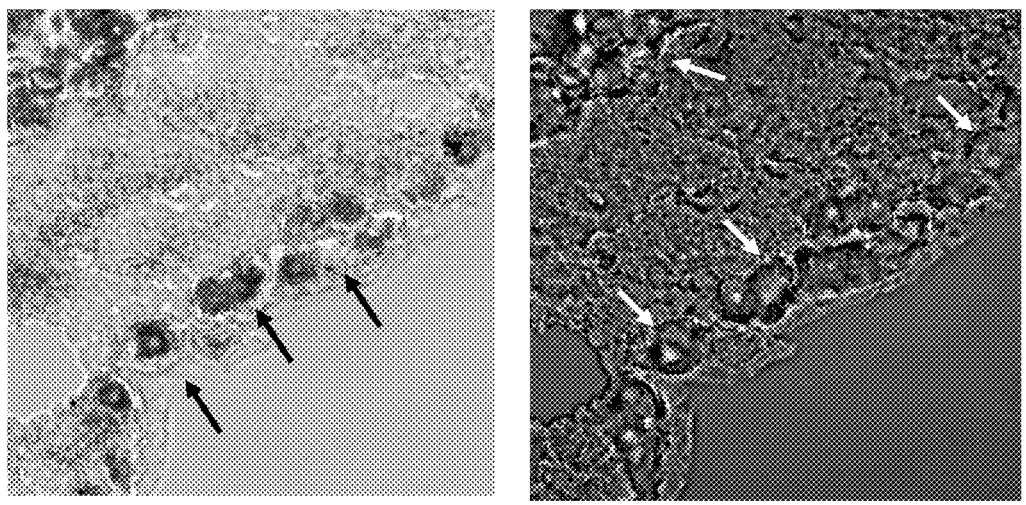
FIGS. 9A-9B show delivery of different structures of Casp2 to the mouse retinal tissues.
Figure 9B:
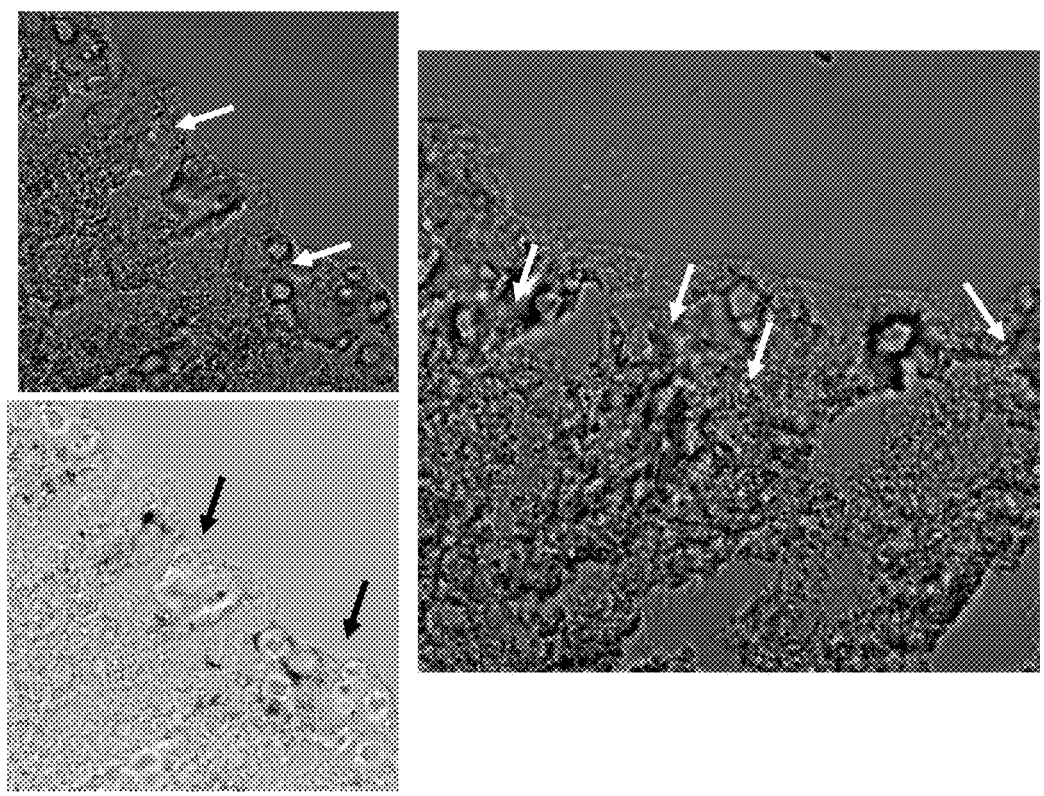

FIG. 8A-8C represent control siRNA FITC-CNL__1RD/CNL__1FD and scarmbled3' cy3-CNL__1 delivery to retinal tissues by different staining methods. FIGS. 9A and 9B show delivery of different structures of Casp2 to the mouse retinal tissues.

Figure 10A:
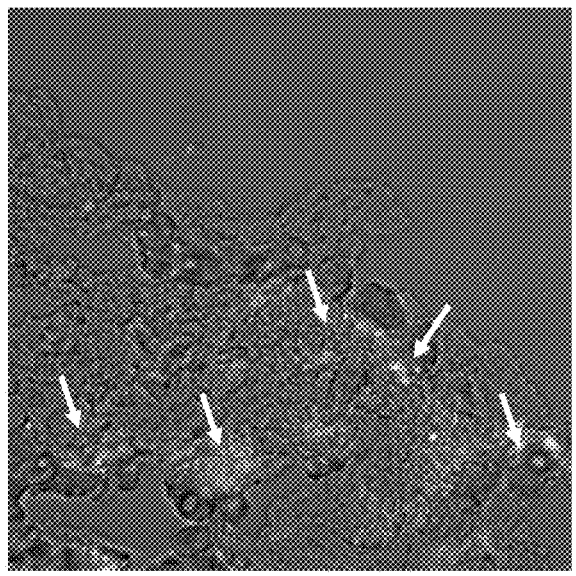
FIGS. 10A-10B show TGASEII-FAM and HNOEL-FAM delivery.
Figure 10B:
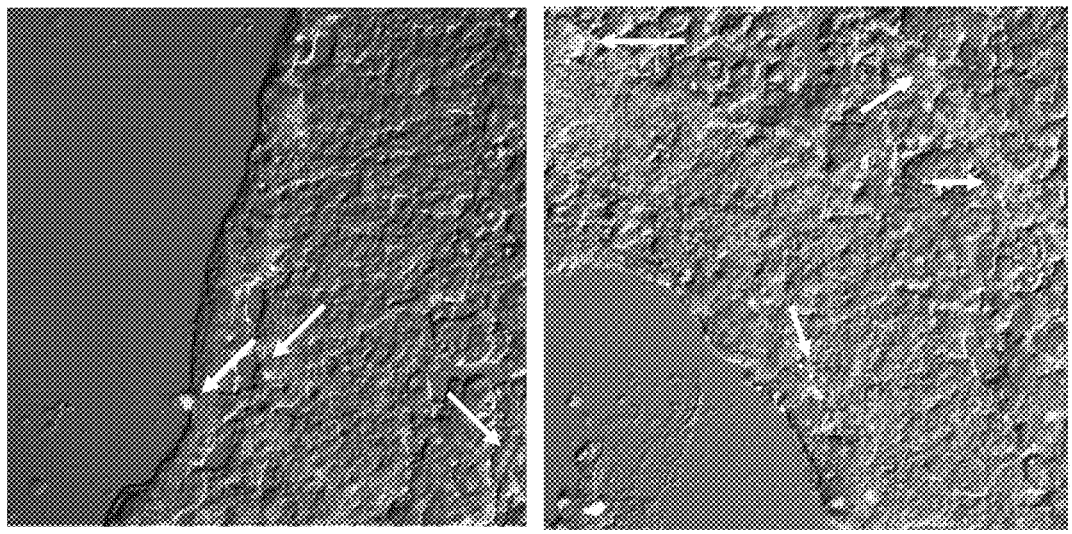

FIGS. 10A and 10B show TGASEII-FAM and HNOEL-FAM delivery.

Figure 11:
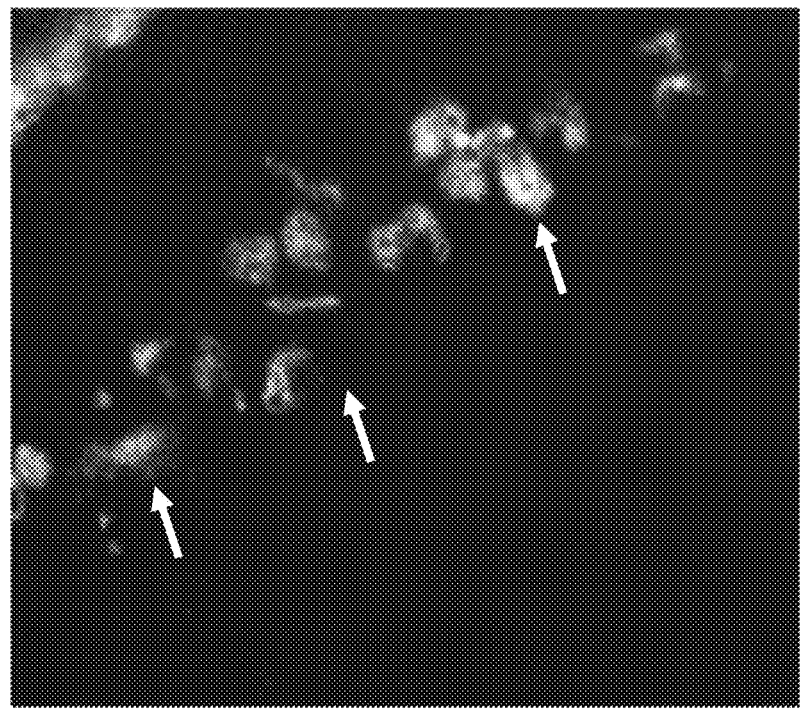
FIG. 11 shows retinal delivery of siRNA against p53 in PBS as positive control group.
Figure 11:
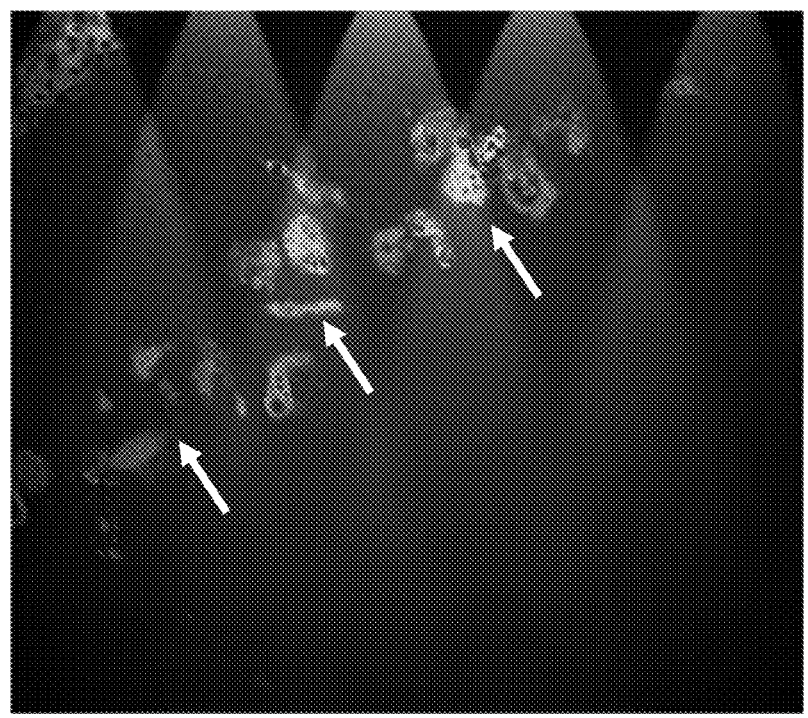
Figure 12A:
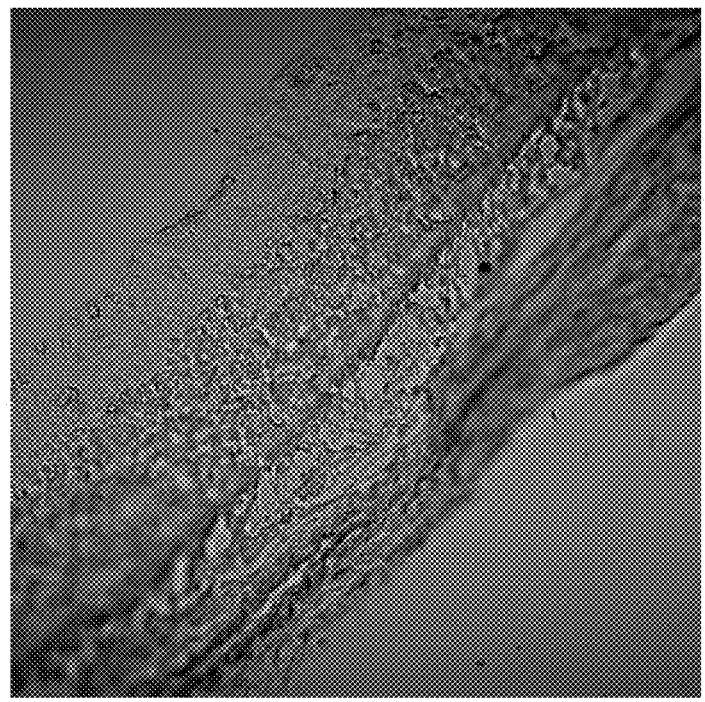
FIGS. 12A-12B show that in intact animals or when administering ED without siRNA no fluorescent signal is obtained in the retina.
Figure 12B:
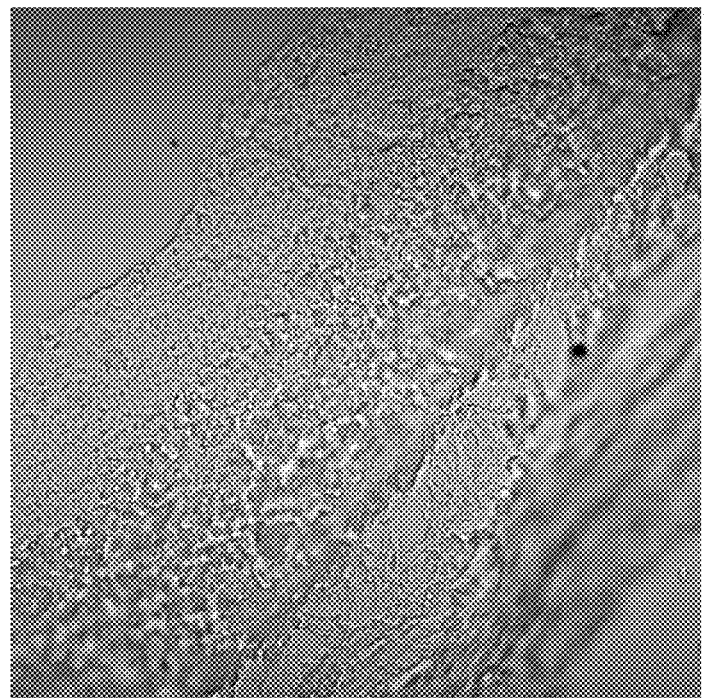
Figure 13A:
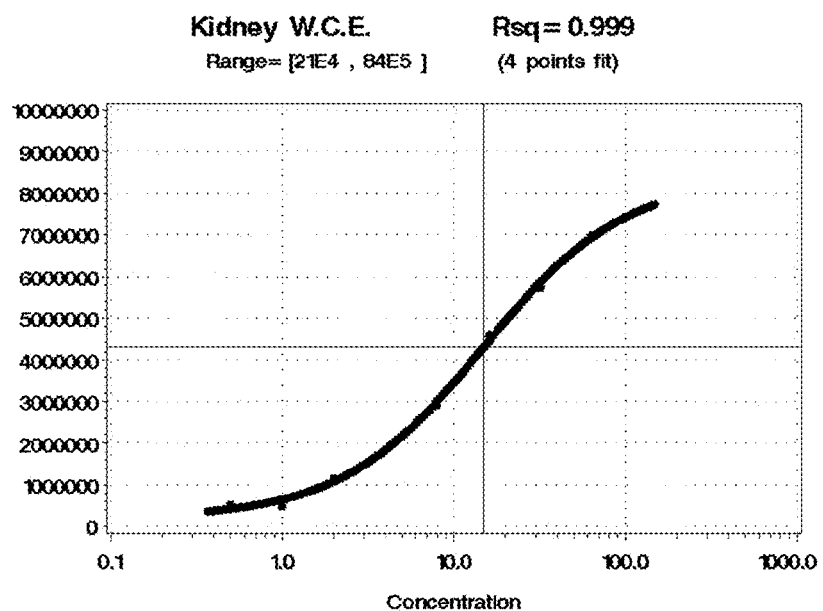
FIG. 13A shows different dilutions of kidney protein extract and measurement of p53 protein levels by specific ELISA assay creating a standard curve.
Figure 13B:
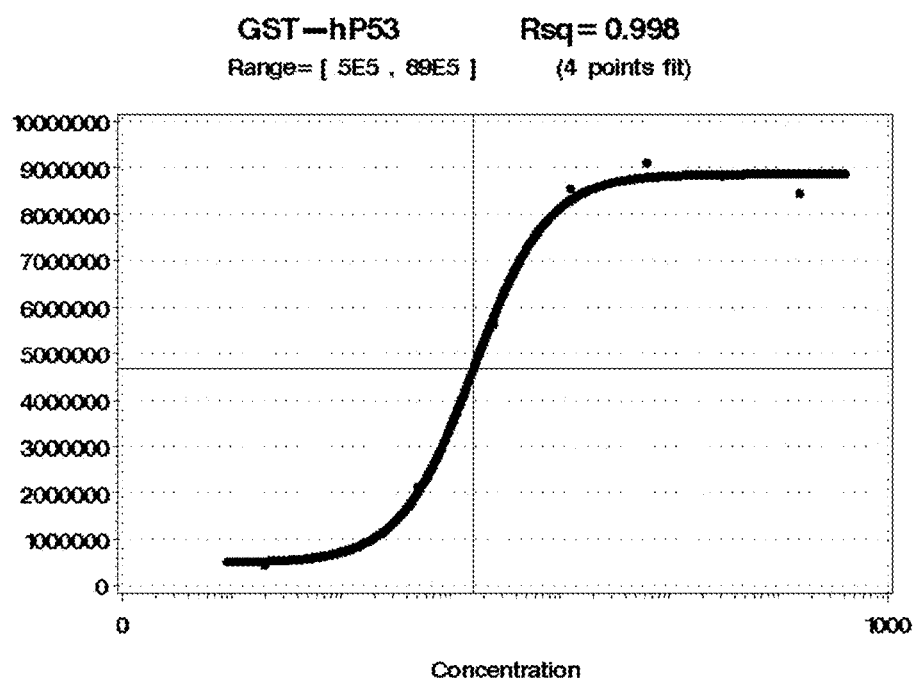
FIG. 13B shows ELISA standard curve based on purified fused GST-hp53 protein.
Figure 13C:
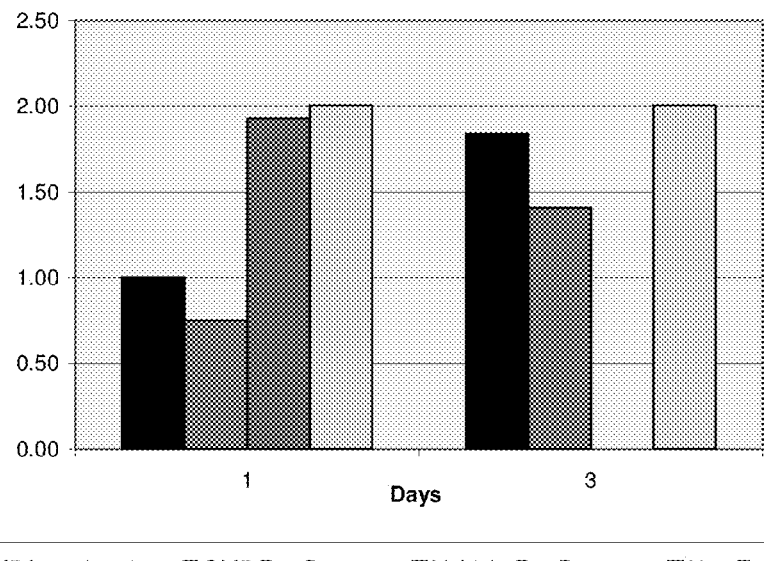
FIG. 13C is a graphical representation of the results provided in Table C14 and depicting the effect of treatments with an siRNA compound targeting the p53 gene (QM5), administered intravitreally or by application of eye drops, on the expression of p53 as measured in retinal protein extracts using an ELISA test. p53 protein levels in the retina were calculated according to standard curve shown in FIG. 13A.
Figure 13D:
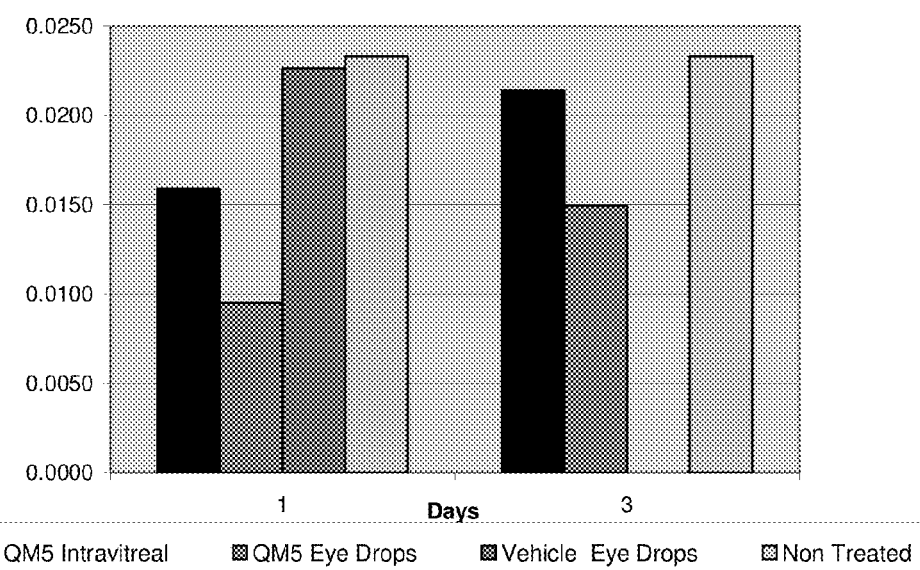
FIG. 13D is a graphical representation of the results provided in Table C16 and depicting the effect of treatments with an siRNA compound targeting the p53 gene (QM5), administered intravitreally or by application of eye drops, on expression of p53 as measured in retinal protein extracts using an ELISA standard curve based on purified fused GST-hp53 protein. p53 protein levels in the retina were calculated according to standard curve shown in FIG. 13B.

FIG. 11 shows retinal delivery of siRNA against p53 in PBS as positive control group and FIGS. 12A and 12B show that in intact animals or when administering ED without siRNA no fluorescent signal is obtained in the retina.

Conclusion: No sequence dependent differences, neither fluorophore nor gene dependent differences in the delivery to the retina were found. The study showed efficient delivery of Cy3 conjugated siRNA compounds directed to CASP2, RTP801, TIGASEII and p53 target genes, to ocular structures: RGC, RPE, photoreceptors, choroid.

Example 6

Quantification of Delivery of Casp2 siRNA
(Formulated in PBS or in MC 2% (Formulation "A")) to Target Retinal Tissue in Rats In-Vivo Examination of different eye Drop formulations for the delivery of siRNA to the retina. The objective of the study was the determination of CASP2_4_S510 siRNA quantity in rat retina at time points 1, 3, 6 & 24 hours following single topical administration in different eye drops (ED) formulations.

Test Article

Substance (unformulated compound): CASP2_4_S510 (siRNA Against CASP2)

Supplied by Agilent (Manufacturer's catalog #QPI-1007, Batch #: Q02F08002N)

Description of the test material: CASP2_4_S510: S—inverted-Abasic 5'-cap, L-DNA 18/AS-AL. A 19-mer chemically modified blunt-ended duplex having two separate strands, with a sense strand (SEN) comprising unmodified ribonucleotides (upper case letters), an L-deoxyribonucleotide at position 18 (bold, underlined) and inverted deoxyabasic moiety (iB) present at the 5' terminus of the SEN strand; and with an antisense strand (AS) comprising unmodified ribonucleotides (upper case letters), and 2'OMe sugar modified ribonucleotides (lower case letters) at positions 2, 4, 6, 8, 11, 13, 15, 17 and 19 as shown in Formula I:

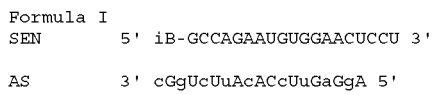

```
Formula I
SEN     5' iB-GCCAGAAUGUGGAACUCCU 3'

AS      3' cGgUcUuAcACcUuGaGgA 5'
```

Storage Conditions: −80° C.

siRNA formulated in PBS: 33.3 mg/ml CASP2_4_S510 in PBS (solution for eye drops)

Description of the test material: Under sterile conditions, 300 mg dry CASP2_4_S510 siRNA were dissolved in 15 ml of sterile double distilled water, to achieve a clear 20 mg/ml solution. The solution was stored at −80° C. until use. The 20 mg/ml stock solution in DDW was then brought to a working concentration of 100 µg/3 µl, in PBS, as follows:

6.5 mg CASP2_4_S510 siRNA: 325 µl of 20 mg/ml stock of CASP2_4 (6.5 mg), were precipitated by 0.15M NaCl and EtOH, and dried under the tissue culture laminar (sterile conditions). siRNA solution 33.3 mg/ml: 6.5 mg dry siRNA were dissolved in 195 µl PBS×1 Quantity prepared: 6.5 mg/195 µl aliquoted into 4 tubes. Storage Conditions: freshly prepared siRNA formulated in Formulation A: 33.3 mg/ml solution of CASP2_4_S510 siRNA in 2% (w/v) methylcellulose & 1% (v/v) sterile glycerol & 0.01% (w/v) EDTA solution in pyrogen free water (solution for eye drops)

Description of the test material: Under sterile conditions, 300 mg dry CASP2_4_S510 siRNA were dissolved in 15 ml of sterile double distilled water, to achieve a clear 20 mg/ml solution. The solution was stored at −80° C. until use. The 20 mg/ml stock solution in DDW was brought to a working concentration of 100 µg/3 µl, in formulation, as follows:

6.5 mg CASP2_4_S510 siRNA: 325 µl of 20 mg/ml stock of CASP2_4 (6.5 mg), were precipitated by 0.15M NaCl and EtOH, and dried under the tissue culture laminar (sterile conditions).

siRNA solution 33.3 mg/ml: 6.5 mg dry siRNA were dissolved in 195 µl Formulation A solution Quantity prepared: 6.5 mg/19411 aliquoted into 4 tubes Storage Conditions: freshly prepared Control Article(s)

Methyl cellulose formulation (no siRNA)-2% methylcellulose & 1% v/v sterile glycerol & 0.01% w/v EDTA solution in pyrogen free water, was prepared as follows:

Solution A: 0.4 g of methylcellulose 25 (ScienceLab.com, Cat# SLM2050) dissolved in final volume of 10 ml of hot boiled water (80-90° C.), (Norbrook), cooled down to room temperature and added in a proportion of 1:1 (final concentration 2%) to solution B.

Solution B: 332 pd of 60% glycerol (Sigma, Cat# G6279) & 2 pd EDTA solution pH8 (prepared from Sigma, Cat# E9884) in 9.66 ml WFI (Norbrook).

500 µL of Solution A mixed with 500 µL of Solution B to obtain: 2% methylcellulose & 1% v/v sterile Glycerol & 0.01% w/v EDTA solution in pyrogen free water (final pH was approximately 7.4 and osmolarity similar to human tear film).

PBS was supplied by Biological industries (Manufacturer catalog #02-023-5A (For 10×PBS); Batch #619113)

Test System

Animals used: Species: Rats; Strain: Adult, Sprague-Dawley (SD)

Source: Harlan, Jerusalem Israel

Age: 8-10 weeks; Body Weight Range: 180-250 gr

Sex: Male; Group Size: n=6/3; Total number of animals: 54

Animal Husbandry: Diet: Animals were provided an ad libitum commercial rodent diet and free access to drinking water.

Environment:

(i) Acclimatization of at least 5 days.

(ii) All animals were confined in a limited access facility with environmentally-controlled housing conditions throughout the entire study period, and maintained in accordance with approved standard operating procedures (SOPs). Animals were provided ad libitum a commercial rodent diet (Harlan Teklad 2018S Global 18% Protein Rodent Diet) and filtered, chlorinated and acidified water.

Rats were kept in microisolator cages with filter top, 1-6 Rats/cage. The cages were maintained under controlled environmental—conditions of temperature (20-24° C.), relative humidity (30-70%), a 12-hr light/12-hr dark cycle, monitored by the control computer, throughout the study period.

Experimental Design

Study design: Retinal concentration of CASP2_4 siRNA following ED application of ocular formulation was determined by qPCR in study groups terminated at different time points after siRNA administration. Each experimental siRNA-treated group included 6 rats. ED was applied bilaterally as detailed in Study Design Table C9.

Termination time points post siRNA administration: Termination setup was performed according to the study design Table C9. Dosing and termination of experimental groups were performed on separate days.

TABLE C9

Study Design

| Group Number | Group Size | Test Article | Dose of Bilateral ED [100 µg/eye/ 3 ul] | Termination [hrs] | Method of Analysis |
|---|---|---|---|---|---|
| 1 | 6 | CASP2_4_S510 | PBS formulated siRNA | 1 | qPCR |
| 2 | 6 | CASP2_4_S510 | MC formulated | 1 | qPCR |
| 3 | 6 | CASP2_4_S510 | PBS formulated siRNA | 3 | qPCR |
| 4 | 6 | CASP2_4_S510 | MC formulated | 3 | qPCR |
| 5 | 6 | CASP2_4_S510 | PBS formulated siRNA | 6 | qPCR |
| 6 | 6 | CASP2_4_S510 | VIC formulated | 6 | qPCR |
| 7 | 6 | CASP2_4_S510 | PBS formulated siRNA | 24 | qPCR |
| 8 | 6 | CASP2_4_S510 | VIC formulated | 24 | qPCR |

TABLE C9-continued

Study Design

| Group Number | Group Size | Test Article | Dose of Bilateral ED [100 μg/eye/3 ul] | Termination [hrs] | Method of Analysis |
|---|---|---|---|---|---|
| 9 | 3 | N/A | Vehicle MC | 1 | qPCR |
| 10 | 3 | N/A | intact | N/A | qPCR |

Anesthesia: In the course of the experiment, the animals were anesthetized with Equithesine (I.P. 4 ml/kg) for ED application and/or before terminations.

Eye Drop Delivery: A 3 μl sample volume of the test article or vehicle was applied to the corneal surface bilaterally to the anesthetized animals, by a blunt pipette tip (filter tips 10 μl sterile (short)). The animals were placed in a warm environment to prevent anesthesia-induced hypothermia, and were returned to their cage after regaining consciousness (experimental Groups 7 and 8). Termination of animals from all study groups was according to study design. Tissues were collected according to study design.

Scheduled euthanasia: All animals were deeply anaesthetized and euthanized according to the study design (Table C9, Termination).

Perfusion setup: Rats were perfused transcardially with PBS (20-50 ml/min following 2-3 min).

Tissue Collection: After perfusion, both eyes (left and right) were enucleated and stored on ice. The eyes were dissected using a microscope, and optionally gross pathology was graded according to the sample grading scale. The cornea was dissected by a cut along the limbus, lens was gently removed, and the retina and vitreous were carefully separated from the sclera. Whole retinas and vitreous bodies (humor) were collected (Retina including: "neural retina"+Retinal Pigment Epithelium+Choroid) into two separate appropriate and properly marked test tubes. Dissected retinas were washed in a large volume of PBS (each retina in a separate tube with fresh PBS), extra liquid was removed with Kimwipe® and retinas were snap-frozen in liquid nitrogen. Retina and Vitreous body samples were s subjected to RNA extraction.

Evaluation

RNA Extraction:

Retina: RNA was extracted from each retina sample individually (left and right) by double extraction. The RNA was transferred for cDNA preparation and qPCR analyses.

Vitreous: Material for Casp2_4 siRNA detection from vitreous was obtained using the following protocol:

Each rat vitreous was around 10 μl. 500 μl of reagent A EZ-RNA II (Biological Industries Cat no. 20-410-100) were added to each vitreous. The sample was homogenized, and 10 μg tRNA (1 μl from 10 mg/ml stock) were added. The sample was stored for 5 minutes at room temperature. Subsequently: EZ-RNA II B: 400 μl and EZ-RNA II C: 90 μl were added and Mixed well. The sample was stored for 10 min at room temperature then centrifuged 12000 g for 15 min at 4° C.

The upper phase was transferred to a fresh tube to which isopropanol: 500 μl and Linear Acrylamide: 5 μl were added. The sample was stored overnight at −20° C., centrifuged at 12000 g for 20 min at 4° C., washed twice with 75% ethanol. The pellet was dissolved in 15 μl $H_2O$.

siRNA Quantification: The quantity of the siRNA in retinas and vitreous humor (siRNA quantification was performed per vitreous) was examined by qPCR siRNA quantification. qPCR was performed according to Quark's standard operating procedures. CASP2_4 siRNA and reference gene expression were tested. Results are summarized in Table C10.

TABLE C10

Results

| Termination | Formulation | Eye | Group size | fmol siRNA/μg retinal RNA |
|---|---|---|---|---|
| 1 hrs | Methyl Cellulose | Right | 5 | 12.50 |
| | | Left | 6 | 10.19 |
| | PBS | Right | 6 | 8.08 |
| | | Left | 6 | 4.77 |
| 3 hrs | Methyl Cellulose | Right | 5 | 1.76 |
| | | Left | 5 | 2.47 |
| | PBS | Right | 6 | 6.48 |
| | | Left | 6 | 7.80 |
| 6 hrs | Methyl Cellulose | Right | 4 | 1.37 |
| | | Left | 6 | 3.80 |
| | PBS | Right | 6 | 3.61 |
| | | Left | 6 | 1.04 |
| 24 hrs | Methyl Cellulose | Right | 6 | 0.11 |
| | | Left | 6 | 0.21 |
| | PBS | Right | 6 | 0.03 |
| | | Left | 6 | 0.04 |

Conclusion: The study showed efficient delivery of siRNA into retina 1 and 3 hours post administration. qPCR analysis showed that after application of 100 μg siRNA in Formulation A, in average 11 fMol/ug of total RNA was obtained in the retina after 1 hour and 2 fMol/ug siRNA after 3 hours. When administering the same concentration in PBS, an amount of 6 fmol/μg of siRNA was obtained after 1 hour and 8 fmol/μg of tot RNA was obtained after 3 hours.

Example 7

Quantification of Non-Invasively Administered siRNA Compound (Formulated in Various Formulations) in Target Retinal Tissue in Rats Examination of different eye drop formulations for non-invasive delivery of siRNA to the retina in vivo.

The objective of this study was the assessment of CASP2_4_S510 siRNA quantity in normal rat retina at 3 hours following single topical application of different siRNA formulations prepared for administration as eye drops (ED).

Test Article

Substance (unformulated compound) CASP2_4_S510 (siRNA Against CASP2) Supplied by Agilent (Manufacturer's catalog #QPI-1007; Batch #: Q02F08002N).

Description of the test material: CASP2_4_S510: S—inverted-Abasic 5'-cap, L-DNA 18/AS-AL. A 19-mer stabilized double strand RNA with inverted Abasic as 5'-cap, L-DNA at the 18 position of the sense strand and alternating 2'-OMe at positions 2, 4, 6, 8, 11, 13, 15, 17 & 19 on the antisense strand.

Storage Conditions: −80° C.

siRNA formulated in PBS 33.3 mg/ml CASP2_4_S510 in PBS (solution for eye drops)—

Description of the test material: Under sterile conditions, 300 mg dry CASP2_4_S510 siRNA were dissolved in 15 ml of sterile double distilled water, to achieve a clear 20 mg/ml solution. The solution was stored at −80° C. until use. The 20 mg/ml stock solution in double distilled water was then brought to a working concentration of 100 μg/3 μg, in PBS, as follows:

1.7 mg CASP2_4_S510 siRNA: 85 μl of 20 mg/ml stock of CASP2_4 (1.7 mg), were precipitated by 0.15M NaCl and EtOH, and dried under the tissue culture laminar (sterile conditions).

siRNA solution 33.3 mg/ml: 1.7 mg dry siRNA were dissolved in PBS ×1 to achieve 51 µl Quantity prepared: 1 tube of 1.7 mg in 51 µl of PBS Storage Conditions: freshly prepared siRNA formulated in commercial lubricant solution Systane®: 33.3 mg/ml CASP2_4_S510 in Systane (solution for eye drops)—Group II. Purchased from Alcone Inc.; Batch #: Lot 165228F.

Description of the test material: Under sterile conditions, 300 mg of CASP2_4_S510 powder (Aligent, batch #Q02F08002N) were dissolved in 15 ml of sterile double distilled water, to achieve a clear 20 mg/ml solution. The solution was stored at −80° C. until use. The 20 mg/ml stock solution in double distilled water was then brought to a working concentration of 100 µg/3 µl, in formulation, as follows:

1.7 mg CASP2_4_S510 siRNA: 85 µl of 20 mg/ml stock of CASP2_4_S510 (1.7 mg), was precipitated by 0.15M NaCl and EtOH, and dried under the tissue culture laminar (sterile conditions).

siRNA solution 33.3 mg/ml: 1.7 mg dry siRNA was dissolved in 51 µL commercial lubricant solution (i.e. Systane®).

Quantity prepared: 1 vial of 1.7 mg siRNA in 51 µL Systane solution.

SiRNA formulated in glycerol+EDTA solution and in methyl cellulose (MC) Solutions: 33.3 mg/ml solution of CASP2_4_S510 siRNA in Glycerol+EDTA formulation, and in 0.5%, 2% or 3% (w/v) methylcellulose & 1% (v/v) sterile glycerol & 0.01% (w/v) EDTA solution in pyrogen free water—Groups III-VI Description of the test material: Under sterile conditions, 300 mg of CASP2_4_S510 powder (Aligent, batch #Q02F08002N) were dissolved in 15 ml of sterile double distilled water, to achieve a clear 20 mg/ml solution. The solution was stored at −80° C. until use. The 20 mg/ml stock solution in double distilled water was then brought to a working concentration of 100 µg/3 µl, in formulation, as follows:

Seven vials of 1.7 mg CASP2_4_S510 siRNA: 85 µl of 20 mg/ml stock of CASP2_4_S510 (1.7 mg), was precipitated by 0.15M NaCl and EtOH, and dried under the tissue culture laminar (sterile conditions).

Group III: 0.5% MC formulation: 1:7 mixture of solution A and solution B [12.5 µL of Solution A were mixed with 50 µL of Solution B and 37.5 pd WFI to obtain: 0.5% methylcellulose & 1% v/v sterile Glycerol & 0.01% w/v EDTA solution in pyrogen free water (final pH was approximately 7.4 and osmolarity similar to human tear film)]

siRNA formulated in 0.5% MC formulation 33.3 mg/ml: 1.7 mg dry siRNA were dissolved in 0.5% MC formulation that was prepared as described to achieve a 51 µL formulated solution of siRNA in 0.5% MC formulation.

Group IV: 1% MC formulation: 1:3 mixture of solution A and solution B [25 µL of Solution A were mixed with 50 µL of Solution B and 25 pd of WFI to obtain: 1% methylcellulose & 1% v/v sterile Glycerol & 0.01% w/v EDTA solution in pyrogen free water (final pH was approximately 7.4 and osmolarity similar to human tear film)]

siRNA solution formulated in 1% MC formulation 33.3 mg/ml: 1.7 mg dry siRNA were dissolved in 1% MC formulation that was prepared as described to achieve a 51 µL formulated solution of siRNA in 1% MC formulation.

Group V: 2% MC formulation: 1:1 mixture of solution A and solution B [5 µL of Solution A were mixed with 50 µL of Solution B to obtain: 2% methylcellulose & 1% v/v sterile Glycerol & 0.01% w/v EDTA solution in pyrogen free water (final pH was approximately 7.4 and osmolarity similar to human tear film)]

siRNA solution formulated in 2% MC formulation 33.3 mg/ml: 1.7 mg dry siRNA were dissolved in 2% MC formulation that was prepared as described to achieve a 51 µL formulated solution of siRNA in 2% MC formulation.

Group VI: 3% MC formulation: 1:1 mixture of solution A and solution C [50 µL of Solution A were mixed with 50 µL of Solution C to obtain: 3% methylcellulose & 1% v/v sterile Glycerol & 0.01% w/v EDTA solution in pyrogen free water (final pH was approximately 7.4 and osmolarity similar to human tear film)]

siRNA solution formulated in 3% MC formulation 33.3 mg/ml: 1.7 mg dry siRNA were dissolved in 3% MC formulation that was prepared as described to achieve a 51 µL formulated solution of siRNA in 4% MC formulation.

Group VII: Glycerol+EDTA formulation: 50 µL WFI (Norbrook) were mixed with 50 µL of Solution B to get: 1% v/v sterile Glycerol & 0.01% w/v EDTA solution in pyrogen free water.

siRNA solution formulated in Glycerol+EDTA formulation 33.3 mg/ml: 1.7 mg dry siRNA were dissolved in Glycerol+EDTA formulation that was prepared as described to achieve a 51 µL formulated solution of siRNA in Glycerol+EDTA formulation.

Quantity prepared: 7 vials, as follows:
1 vial of 1.7 mg siRNA in 51 µL PBS formulation
1 vial of 1.7 mg siRNA in 51 µL Systane® formulation
1 vial of 1.7 mg siRNA in 51 µL 0.5% MC formulation
1 vial of 1.7 mg siRNA in 51 µL 1% MC formulation
1 vial of 1.7 mg siRNA in 51 µL 2% MC formulation
1 vial of 1.7 mg siRNA in 51 µL 3% MC formulation
1 vial of 1.7 mg siRNA in 51 µL Glycerol+EDTA formulation Storage Conditions: freshly prepared
Control Article(s)
1. PBS—Supplied by Biological industries (Manufacturer catalog #02-023-5A (For 10×PBS); Batch #619113).
2. Systane®—commercially available eye drop solution; Supplied by Alcon; Batch #: Lot 165228F; Quantity supplied: 15 ml; Storage Conditions: RT; Expiration Date: 02/2011.

Formulation Solution A—methylcellulose solution in pyrogen free water Solution A) 0.4 g of methylcellulose 25 (ScienceLab.com, Cat# SLM2050) dissolved in final volume of 10 ml of hot boiled water (80-90° C.), (Norbrook), cooled down to room temperature.

Formulation Solution B—Sterile Glycerol & EDTA solution in pyrogen free water Solution B) 332 µl of 60% glycerol (Sigma, Cat# G6279) & 2 µl EDTA solution pH8 (prepared from Sigma, Cat# E9884) in 9.666 ml WFI (Norbrook).

Formulation Solution C—Concentrated methylcellulose solution in pyrogen free water Solution C) 0.6 g of methylcellulose 25 (ScienceLab.com, Cat# SLM2050) dissolved in final volume of 10 ml of hot boiled water (80-90° C.), (Norbrook), cooled down to room temperature.

Stability Tests of siRNA Compounds in the Above Methyl Cellulose Formulations:

The stability of Casp2_4 Q02F08002N siRNA was tested in Methyl cellulose formulations according to the following protocol:

siRNA was diluted in the different formulations containing Methyl cellulose, to a final concentration of 7 µM siRNA. The 0%, 0.5%, 1%, 2% and 3% MC formulations were incubated at Room Temperature. In addition, the 3% MC formulation was also incubated at 37° C. with and without nuclease inhibitor.

A 5-μL aliquot of each solution was transferred to 15 μL of 10×TBE-loading buffer after incubation at the following time points: 0.10', 0.5, 1, 1.5, 3, 6 h. The solution was then frozen in liquid nitrogen, and stored at −20° C.

4 μL of each sample was loaded onto a non-denaturing 20% polyacrylamide gel and electrophoresis was performed at 80V for 2.5 h.

For siRNA visualization the gel was stained with Ethidium bromide solution (1.0 μg/μL).

As a positive control for gel migration of a non-degraded siRNA, 5 μL of a 7 μM tested siRNA solution in PBS was transferred to 15 μL of 10×TBE-loading buffer and loaded onto the gel. Then, the sample was frozen in liquid nitrogen and stored at −20° C.

As a reference to the migration pattern of a degraded single strand (ss) siRNA, a non-relevant single strand siRNA was prepared.

Results: The Casp 2_4 siRNA compound was stable in all formulations.

The In Vivo Study:

Test System:

Animals used: Rats; Strain: Adult, Sprague-Dawley; Modification: SD

Source: Harlan, Jerusalem Israel

Age: 8-10 weeks; Body Weight Range: 220-270 gr

Sex: Male; Group Size: n=6; Total number of animals: 54

Animal Husbandry: Diet: Animals were provided an ad libitum commercial rodent diet and free access to drinking water.

Environment:

(i) Acclimatization of at least 5 days.

(ii) All the animals were confined in a limited access facility with environmentally-controlled housing conditions throughout the entire study period, and maintained in accordance with approved standard operating procedures (SOPs). Animals were provided ad libitum a commercial rodent diet (Harlan Teklad 2018S Global 18% Protein Rodent Diet) and filtered, chlorinated and acidified water.

Rats were kept in microisolator cages with filter top, 1-6 Rats/cage. The cages were maintained under controlled environmental conditions of temperature (20-24° C.), relative humidity (30-70%), a 12-hr light/12-hr dark cycle, monitored by the control computer, throughout the study period.

Experimental Design

Experimental setup included 9 experimental groups (6 rats per group). ED were applied bilaterally. Different formulations were used (Study Design Table C11). Termination time point (3 hrs) post siRNA administration: Termination setup was performed according to the study design Table C11. Retinal concentration of CASP2_4 siRNA was determined by qPCR.

TABLE C11

Study Design

| Group | Delivery Route | Formulation | siRNA Compound | Bilateral Application (dose/volume/eye) | Term. Time Point (hrs) | Group Size |
|---|---|---|---|---|---|---|
| I | ED | PBS | Casp2_4_S510 | 100 μg/3 μl | 3 | 6 |
| II | ED | Systane | Casp2_4_S510 | 100 μg/3 μl | 3 | 6 |
| III | ED | MC0.5% | Casp2_4_S510 | 100 μg/3 μl | 3 | 6 |
| IV | ED | MC1% | Casp2_4_S510 | 100 μg/3 μl | 3 | 6 |
| V | ED | MC2% | Casp2_4_S510 | 100 μg/3 μl | 3 | 6 |
| VI | ED | MC3% | Casp2_4_S510 | 100 μg/3 μl | 3 | 6 |
| VII | ED | Glycerol + EDTA * | Casp2_4_S510 | 100 μg/3 μl | 3 | 6 |
| VIII | ED | PBS | — | — | 3 | 6 |
| IX | Intact | — | — | — | — | 6 |

* Glycerol + EDTA formulation (MC free formulation) = 1% v/v sterile glycerol & 0.01% w/v EDTA solution in pyrogen free water Anesthesia: In the course of the experiment, All ED treated animals were anesthetized with Equithesine (I.P. 4 ml/kg).

Eye Drop Delivery A 3 μl sample volume of the test article or vehicle were applied to the corneal surface bilaterally to the anesthetized animals, by a blunt pipette tip (filter tips 10 μl sterile (short)). The animals were placed in a warm environment to prevent anesthesia-induced hypothermia. Termination of animals from all study groups was according to study design (time point 3 hrs). Tissues were collected according to study design.

Scheduled euthanasia: All animals were deeply anaesthetized and euthanized according to the study design (Table C11, Termination).

Perfusion setup: Rats were perfused transcardially with PBS (20-50 rpm/min following 2-3 min).

Tissue Collection: After perfusion, both eyes (left and right) were washed with PBS, were enucleated and stored on ice. The eyes were dissected using a binocular microscope, and optionally gross pathology was graded according to the sample grading scale. The cornea was dissected by a cut along the limbus, lens was gently removed, and the retina and vitreous were carefully separated from the sclera. Whole retinas and vitreous bodies (humor) were collected into two separate appropriate and properly marked test tubes. Dissected retinas were washed in a large volume of PBS (each retina in a separate tube with fresh PBS), extra liquid was removed with Kimwipes and retinas were snap-frozen in liquid nitrogen. Retina and Vitreous body samples were subjected to RNA extraction.

Evaluation:

RNA Extraction: Retina: RNA was extracted from each retina sample individually (left and right) by double extraction. The RNA was transferred for cDNA preparation and qPCR analyses.

Vitreous: Material for Casp2_4_S510 siRNA detection from vitreous was obtained using the following protocol: Each rat vitreous was around 10 μl. 500 μl of reagent A EZ-RNA II (Biological Industries Cat no. 20-410-100) were added to each vitreous. The sample was homogenized, and 10 μg tRNA (1 μl from 10 mg/ml stock) were added. The sample was stored for 5 minutes at room temperature. Subsequently EZ-RNA II B: 400 pd and EZ-RNA II C: 90 μl were added and mixed well. The sample thus obtained was stored for 10 min at room temperature then centrifuged 12000 g for 15 min at 4° C.

The upper phase was transferred to a fresh tube to which isopropanol: 500 μl and Linear Acrylamide: 5 μl were added. The sample was stored overnight at −20° C., centrifuged at 12000 g for 20 min at 4° C., washed twice with 75% ethanol. The pellet was dissolved in 15 μl DDW.

siRNA Quantification: The quantity of the siRNA in retinas and vitreous humor (siRNA quantification was performed per vitreous) was examined by qPCR siRNA according to Quark's standard operating procedures.

Results

The study showed that the following quantities of siRNA were detected in the rat retina three hours post application of siRNA non-invasively administered in vivo with the different formulations:

TABLE C12

| CASP2 siRNA Normalized (miRNA) quantity in fmle/1 μg RNA | | | | |
|---|---|---|---|---|
| Group | Abbreviation | N | Mean | Std |
| IX | I-N/A | 6 | 0.005 | 0.005 |
| VIII | P-PBS | 6 | 0.056 | 0.124 |
| VII | C-MC(0) | 6 | 6.303 | 3.921 |
| XA | C-MC(1/2) | 4 | 17.831 | 16.628 |
| XIA | C-MC(1) | 6 | 5.677 | 4.235 |
| V | C-MC(2) | 6 | 6.963 | 8.042 |
| VI | C-MC(3) | 5 | 7.653 | 6.674 |
| II | C-Systane | 5 | 5.109 | 2.492 |
| I | C-PBS | 6 | 4.228 | 6.758 |

MC(0)-MC(3)—formulations including increasing concentrations from 0 to 3% of Methyl Cellulose.

Conclusion: All groups that were treated by CASP2 siRNA show positive quantities of the siRNA (>4 fmole) in target retinal tissue. No significant difference (P-value=0.8425) were found between the formulation groups.

Non-Invasively Administered siRNA Induces In-Vivo Knockdown (KD) of Target Gene Associated with Apoptosis in Target Ocular Tissue Example 8

Determination of In-Vivo Knockdown Activity of siRNA Against p53 Prepared for Non-Invasive Administration by Eye Drops in Rat Retina (siRNA Compound Formulated in MC 2% (Formulation "A")

Objective

The objective of the study was to determine knockdown activity of non-invasively delivered siRNA compound targeting p53 mRNA in the rat neural retina. The siRNA compound was formulated for non-invasive administration by eye drops. Knockdown activity was assessed by protein level determination using ELISA method.

Test Article a. Substance (unformulated siRNA compound): QM5 (siRNA Against Mouse/Rat p53)

b. Formulated siRNA compound for non-invasive (eye drop) delivery (groups 2 & 5 in Table C13): 100 μg/3 μl solution of QM5 siRNA in 2% (w/v) methylcellulose & 1% (v/v) sterile glycerol & 0.01% (w/v) EDTA solution in pyrogen free water.

c. Formulated siRNA compound for intravitreal injection (groups 1 & 4 in Table C13): 280 μg of QM5 siRNA in 140 μl of PBS d. Formulated vehicle solution for non-invasive (eye drop) delivery (groups 3 & 6 in Table C13): 2% methylcellulose & 1% v/v sterile glycerol & 0.01% w/v EDTA solution in pyrogen free water.

Test System:

Adult Male, Sprague-Dawley (SD) Rats Harlan, Jerusalem Israel, 6-8 weeks old, 160-180 gr each.

Experimental Design

Study design: Unilateral axotomy (left eye, OS) was performed in each animal from groups 1-6.

Groups 2, 3, 5 & 6: Test compound (100 μg test article in 3 μl of formulated vehicle—groups 2&5) or formulated vehicle alone (groups 3&6) were applied as eye drops every day starting on day 0 (immediately after axotomy). Experimental groups were terminated according to Table C13. Left and Right eye samples from group 7 served as an intact normal controls.

Groups 1 & 4: Three minutes following axotomy (at day 0), 20 μg of siRNA compound in 10 pd of PBS vehicle were applied by microinjection into the vitreous. The microinjection into the vitreous was performed perpendicular to the sclera, using an Insulin micro-injector (0.3 ml). Animals were terminated according to Table C13.

TABLE C13

| | | | Study Design: | | |
|---|---|---|---|---|---|
| Group | Group Size | Axotomy (unilat. OS) | Intravitreal injection (OS) (dose/volume/eye) | ED (OS) (dose/volume/eye) | Termination (days) |
| 1 | 6 | Yes | QM5 20 μg/10 μl | N/A | 1 |
| 2 | 6 | Yes | N/A | QM5 100 μg/3 μl | 1 |
| 3 | 4 | Yes | N/A | Formulated vehicle | 1 |
| 4 | 6 | Yes | QM5 20 μg/10 μl | N/A | 3 |
| 5 | 6 | Yes | N/A | 3x QM5 100 μg/3 μl | 3 |
| 6 | 4 | Yes | N/A | 3x Formulated vehicle | 3 |
| 7 | 4 | N/A | N/A | N/A | N/A |

(see Tables C14-C17 hereinbelow and FIGS. 11A and 11B)

p53 Signal According to Kidney W.C.E Standard Curve

TABLE C14

| p53 signals values according to Kidney W.C.E standard curve | | | |
|---|---|---|---|
| P53 Signal | | retina | |
| Operation | Treatment | 1 days | 3 days |
| Axotomy | QM5 Intravitreal | 1.00 | 1.84 |
| Axotomy | QM5 Eye Drops | 0.75 | 1.41 |
| Axotomy | Vehicle Eye Drops | 1.93 | Missing |
| None | Non Treated | 2.01 | 2.01 |

TABLE C15

% p53 signals ratio from non-treated animals

| | % signal ratio from non-treated | | retina |
|---|---|---|---|
| Axotomy | QM5 Intravitreal | 50% | 92% |
| Axotomy | QM5 Eye Drops | 37% | 70% |
| Axotomy | Vehicle Eye Drops | 96% | 0% | p53 Signal According to GST-Hp53

TABLE C16 p53 signal values according to GST-p53 standard curve

| | P53 Signal | retina | |
|---|---|---|---|
| Operation | Treatment | 1 day | 3 days |
| Axotomy | QM5 Intravitreal | 0.0159 | 0.0214 |
| Axotomy | QM5 Eye Drops | 0.0095 | 0.0149 |
| Axotomy | Vehicle Eye Drops | 0.0227 | Missing |
| None | Non Treated | 0.0233 | 0.0233 |

TABLE C17

% P53 signals ratio from non-treated animals

| | % Signal ratio from non-treated | | retina |
|---|---|---|---|
| Axotomy | QM5 Intravitreal | 68% | 92% |
| Axotomy | QM5 Eye Drops | 41% | 64% |
| Axotomy | Vehicle Eye Drops | 97% | Missing |

Conclusion: These studies showed that non-invasively delivered siRNA compound targeting p53 mRNA in the rat neural retina induces knock down of the p53 protein.

siRNA Compounds Induce Ocular Neuroprotection In-Vivo in Animal Models of Ocular Neuronal Injury Example 9

Evaluation of Ocular Neuroprotective Induction by siRNA Compound Targeting Caspase 2 in the ONC Model after IVT Injection Study objectives: To evaluate ocular neuroprotective efficacy of siRNA targeting Caspase 2 in the ONC model following intravitreal injection(s)
Methods
Retrograde Labelling of RGCs.

The Fluorogold tracer is transported retrogradely (from brain to eye) along RGC axons resulting in complete and specific labeling of all RGCs. For the purpose of this study, RGCs were labeled by application of the retrograde tracer FluoroGold (2%, Fluorochrome, Englewood, Colo.) in the superior colliculus. Briefly, a window was drilled in the scalp above the coordinates 6 mm rostral to the bregma and 1.2 mm lateral to the midline in both hemispheres. Using a Hamilton syringe, 3 pd of the FluoroGold was injected into superior colliculus 3.8 mm, 4 mm, and 4.2 mm below the bony surface at a rate 1 μl/min at each of the three depths. The needle was then slowly withdrawn and the skin was sutured. In adult rats, the time required to obtain full labeling of all RGCs following this procedure was ~1 week. For this reason, ONC was performed one week after retrograde labeling of RGCs.

Optic nerve crush. The orbital optic nerve (ON) of anaesthetized adults Wistar rats was exposed through a supraorbital approach, the meninges severed and all axons in the optic nerve (ON) transected by crushing with calibrated forceps for 10 seconds, 2 mm from the lamina cribrosa.

Intravitreal (WT) injection. One or two 20 μg doses (in 10 pd of PBS) of test or control siRNAs or 10 μl of PBS vehicle were microinjected into the vitreous body 2 mm anterior to the nerve head, perpendicular to the sclera, using a glass micropipette. IVT administration is shown as a control and or for initial validation of a target gene.

Quantification of RGC survival. At termination, experimental animals were perfused transcardially with 4% paraformaldehyde. The eyes with the optic nerve were enucleated, the cornea was dissected with the blade and lens/vitreous were gently removed. Both retinas were dissected out, fixed for an additional 30 min and flat-mounted vitreal side up on a glass slide for examination of the ganglion cell layer. RGCs were examined under the fluorescence microscope with an UV filter (365/420 nm). The number of retrogradely fluorescent RGCs were determined by two different, independent and "blinded" investigators counting them in 16 distinct areas (four areas per retinal quadrant at three different eccentricities of one-sixth, one-half, and five-sixths of the retinal radius). Microglia that may have incorporated FluoroGold after phagocytosis of dying RGCs was distinguished by their characteristic morphology and excluded from quantitative analyses.

Part 1

Test article: CASP2_4 siRNA—a double-stranded 19-mer oligonucleotide chemically modified by 2'O-methylation on both strands. Other compounds included siRNA chemically modified with L-DNA at the 3' terminus of the sense strand or 2'5' bridges at the 3' terminus. Targets the caspase2 gene in multiple species.

Control article: PBS

Design: Retinal ganglion cells (RGC) were selectively labeled first by application of the retrograde tracer FluoroGold to the superior colliculus. One week later, animals were subjected to optic nerve crush injury (ONC). The quantifications of surviving RGCs were carried out at 7 and 30 days after ONC by counting FluoroGold-labelled RGCs on flat-mounted retinas. Table C18 shows the groups treatments.

TABLE C18

Group Treatments

| Groups | Right eye (n = 4) | Left eye (n = 4) | Termination |
|---|---|---|---|
| 1 and 2 | 20 μg siCasp2_4 on day 0 | 20 μl PBS on day 0 | Day 7 |
| 3 and 4 | 20 μg siCasp2_4 on days 0 and 10 | 20 μl PBS on days 0 and 10 | Day 30 |

Results: The mean number of surviving RGCs in eyes treated with 20 μg Casp2_4 siRNA and subjected to optic nerve crush was 2040±35 cells/mm2 at 7 days and 298±25 cells/mm2 at 30 days post injury. These counts were significantly greater than the mean RGC counts in eyes treated with PBS and subjected to nerve crush, which was 941±27 cells/mm2 at 7 days and 41±7 cells/mm2 at 30 days. In the non-surgical control eyes, the mean number of RGCs was 2253±104 cells/mm2, which is comparable to the average number of RGCs reported in literature. Table C19 provides the results of this study.

TABLE C19

Mean numbers of survived RGC at the different time points post injury

| | Time post ONC | | | |
|---|---|---|---|---|
| | 7 days | | 30 days | |
| Treatment | PBS | Casp2_4 | PBS | Casp2_4 |
| Mean survival RGC (cells/mm2) | 941.347 | 2039.672 | 41.040 | 298.051 |
| SD | 27.038 | 34.766 | 7.219 | 25.401 |
| % of RGC survival from total RGC | 26.659 | 57.764 | 1.162 | 8.441 |
| SD | 0.766 | 0.985 | 0.204 | 0.719 |

All data are given as mean±standard deviation. Values were compared using one-way analysis of variance (ANOVA) and considered as significantly different at P<0.02.

Conclusions: The increased survival of the RGCs was not due to the neuroprotective effects of anesthesia (ketamine is an antagonist of the N-methyl-D-aspartate receptor, and xylazine is an α2-adrenergic receptor agonist), since identically anesthetized animals in the control group had significantly lower RGC counts than did animals in the Casp2_4 siRNA treated group, but due to neuroprotective effect of silencing pro-apoptotic Caspase 2 activation and up regulation following ONC injury, by treatment with siRNA compound targeting the Caspase 2 gene.

Part 2

Test article: CASP2_4L siRNA—a double-stranded 19-mer oligonucleotide chemically modified by 2'O-methylation on the antisense strand and L-DNA on the sense strand. Targets the caspase 2 gene of multiple species.

Control articles:
PBS
siRNA targeting GFP—a double-stranded 21-mer oligonucleotide stabilized by 2'O-methylation on both strands.
CNL—siRNA with no match to any known mammalian transcript; a double-stranded 19-mer oligonucleotide chemically modified by 2'O-methylation on both strands.

Design. Retinal ganglion cells (RGC) were selectively labeled first by application of the retrograde tracer FluoroGold to the superior colliculus. One week later, animals were subjected to optic nerve crush injury (ONC). The quantifications of surviving RGCs were carried out at day 7 after ONC by counting FluoroGold-labelled RGCs on flat-mounted retinas. Test or control articles were injected at the time of ONC. Similar experiments were performed in order to test activity and efficacy of siRNA administered via eye drops (see next example). Table C20 shows groups treatments.

TABLE C20

Groups Treatments

| Groups | Right eye (n = 4) | Left eye (n = 4) | Termination |
|---|---|---|---|
| 1 and 2 | 20 µg siCasp2_4 on day 0 | 20 µl PBS on day 0 | Day 7 |
| 3 and 4 | 20 µg siGFP on day 0 | 20 µl siCNL_1 on day 0 | Day 7 |

Results: The mean number of surviving RGCs in eyes treated with 20 µg Casp2_4 siRNA and subjected to optic nerve crush was 2085±40 cells/mm2 at 7 days post injury. These counts were significantly greater than the mean RGC counts in eyes treated with either PBS or GFP siRNA or CNL_1 siRNA and subjected to nerve crush, which was 901±50 cells/mm2, 922±38 cells/mm2, 898±42 cells/mm2 respectively, at 7 days. In the nonsurgical control eyes, the mean number of RGCs was 2196±110 cells/mm2, which is comparable to the average number of RGCs reported in literature. Table C21 shows results. All data are given as mean±standard deviation. Values were compared using one-way analysis of variance (ANOVA) and considered as significantly different at P<0.01.

TABLE C21

Mean numbers of survival RGC 7 days post injury (n = 4 retinas/group).

| Treatment | PBS | siGFP | siCNL_1 | siCasp2 |
|---|---|---|---|---|
| Mean survival RGC (cells/mm2) | 901.3338 | 922.3666 | 898.4268 | 2084.815 |
| SD | 49.74134 | 38.04059 | 42.12429 | 40.03638 |
| % of RGC survival from total RGC | 25.52577 | 26.12142 | 25.44345 | 59.04197 |
| SD | 1.408675 | 1.07731 | 1.19296 | 1.13383 |

Conclusions: The increased survival of the RGCs was due to neuroprotective effect of silencing pro-apoptotic Caspase 2 activation and up-regulation following ONC injury, by treatment with siRNA targeting Caspase 2 gene. The Casp2_4 siRNA molecules having different structural modifications/motifs show similar neuroprotective effect on RGC survival range.

Example 10

Evaluation of Ocular Neuroprotective Efficacy of siRNA Compound Targeting Caspase 2 in the IOP Model The objective of the current study was to establish the neuroprotective effect of a single injection of 20 µg of CASP2_4 compound or negative control GFP siRNAs in the pre-clinical rat glaucoma IOP model.

Study Outline

In animals from all study groups, RGCs were retrograde labeled using the fluorescent tracer DiI (1,1'-dioctadecyl-3,3,3',3'-tetramethylindocarbocyanine) applied to both superior colliculi. A week later, IOP was unilaterally increased in the left eyes of animals from groups 2 to 5. IOP was monitored every other day in the operated (left) and contralateral (right) eyes during 2 weeks. Two weeks following hypertonic saline injection, vehicle (PBS) or siRNA (20 µg in PBS, either siRNA targeting Casp2 or a negative control siRNA targeting the non-mammalian gene, Green Fluorescent Protein), was administered by intravitreal (IVT) injection to the left (operated) eyes. The contralateral non-operated eyes received no IVT injection. In addition, two weeks after hypertonic saline injection, the animals from group 2 were sacrificed and DiI-labeled RGCs were counted in flat mounts of left retinas under fluorescence microscopy, in order to assess the extent of RGC loss at the time of siRNA injection. For all groups receiving WT injection, IOP was measured once during the 3rd week of the experiment to confirm its increased state in the operated eyes. At 3 weeks of increased IOP, or at 1 week after the test and control article injections, the animals were sacrificed and DiI-labeled RGCs were counted in flat mounts of left retinas under fluorescence microscopy. Right retinas served as internal controls for labeling quality. A separate group of naïve rats in which RGC's were retrogradely labeled at the experiment commence was used as an intact control to provide a reference for normal RGC densities. 4 rats from this group were sacrificed at 2 weeks of ocular hypertension (together with group 2) and the remaining 9 rats—at 3 weeks (together with groups 3 to 5). The experimental design is shown in Table C22 below.

Animals

| | | |
|---|---|---|
| Species: | Rats | |
| Strain: | Brown Norway Rats | |
| Modification: | N/A | |
| Source: | Charles River (Canada) | |
| Age: | Adult, retired breeders, 10-12 months of age | |
| Body Weight Range: | 300-400 g | |
| Sex: | Males | |
| Animal Husbandry: | Diet: | |
| | Environment: | All animal procedures were performed in accordance with the guidelines of the Canadian Council on Animal Care for the use of experimental animals (http://www.ccac.ca/). |
| | Environment: | (i) Acclimatization of at least 5 days. (ii) All the animals were confined in a limited-access facility with environmentally controlled housing conditions throughout the entire study period, and maintained in accordance with University of Montreal approved standard operating procedures (SOPs). |

Materials and Equipment

Substance (unformulated compound) CASP2_4_S510 (CASP2_4; CASP2 SIRNA; siRNA Against Caspase2 mRNA)
  Supplied by Agilent
  Description of the test material: A 19-mer chemically modified blunt-ended duplex having two separate strands, with a sense strand (SEN) comprising unmodified ribonucleotides (upper case letters), an L-deoxyribonucleotide at position 18 (bold, underlined) and inverted deoxyabasic moiety (iB) present at the 5' terminus of the SEN strand; and with an antisense strand (AS) comprising unmodified ribonucleotides (upper case letters), and 2'OMe sugar modified ribonucleotides (lower case letters) at positions 2, 4, 6, 8, 11, 13, 15, 17 and 19 as shown in Formula I.
  Quantity supplied: 300 mg
  Storage Conditions: −80° C.
Control Substance (unformulated compound) GFP_5_S763 (siRNA Against GFP mRNA)
  Outsourcing (manufacturer's name): Agilent
  Manufacturer's catalog #N/A
  Quantity supplied: 220.8150 mg
  Storage Conditions: −80° C.; Expiration Date: ND
  Test/Control Article (formulated) CASP2_4/GFP_5 20 μg/5 μL of PBS
  0.5 mg was diluted into 125 μl to achieve a stock solution of 4 μg/μl. These were subsequently aliquoted to 5 μl per tube and stored at −80° C.
  Vehicle—PBS.
Multicell Phosphate buffered saline, solution 1×, without calcium, without magnesium (CAT. No: 311-010-EL).

Fluorescence microscopy was performed using a Zeiss Axioskop 2 Plus microscope (Carl Zeiss Canada, Kirkland, QC), images were captured with a CCD camera (Retiga, Qimaging) and processed with Northern Eclipse image analysis software (Empix Imaging, Mississauga, ON). Microphotographs were taken at 25× magnification.

Experimental Procedure

Surgery was be performed in adult male Brown Norway rats, retired breeders, between 10-12 months of age (300-400 g), under general anesthesia by intraperitoneal injection of 1 mL/Kg standard rat cocktail consisting of Ketamine (100 mg/mL), xylazine (20 mg/mL) and acepromazine (10 mg/mL).

Ocular hypertension surgery: Unilateral and chronic elevation of IOP was induced by using the Morrison model, involving an injection of hypertonic saline into a episcleral vein, leading to a blockade of the aqueous humor outflow pathways. This procedure lead to gradual increase of eye pressure and progressive death of RGS. All the animals in this study received only a single saline vein injection. The eye selected for the procedure was adapted with a plastic ring applied to the ocular equator to confine the saline injection to the limbal plexus. A micro needle (30-50 μm in diameter) was used to inject 50 μL of sterile 1.85 M NaCl solution through one episcleral vein. The plastic ring temporarily blocked off other episcleral veins forcing the saline solution into the Schlemm's canal to create isolated scarring. Animals were kept in a room with constant low fluorescent light (40-100 lux) to stabilize circadian IOP variation (8).

Measurement of intraocular pressure (IOP): IOP from glaucomatous and normal (contralateral) eyes was measured in awake animals using a calibrated tonometer (TonoPen XL, Medotronic Solan, Jacksonville, Fla.). IOP was measured every other day for the first two weeks after ocular hypertension surgery; and at least once between week 2 and week 3 after ocular hypertension surgery. Eyes become fragile after intraocular injections in conditions of high IOP, for this reason the number of IOP measurements was limited as this involves putting additional pressure on the cornea to get a reliable reading. The mean IOP (mmHg±S.E.M) per eye was considered as the average of all IOP readings since the onset of pressure elevation. The maximum IOP measurements in each individual eye, glaucomatous or normal contralateral eye was defined as the peak IOP and this value was used to estimate the mean peak IOP for each group Calculation of intraocular pressure (IOP): The mean IOP (mmHg±S.E.M) per eye was considered as the average of all IOP readings since the onset of pressure elevation. The maximum IOP measurements in each individual eye, glaucomatous or normal contra lateral eye was defined as the peak IOP and this value was used to estimate the mean peak IOP for each group. The positive integral IOP was calculated as the area under the IOP curve in the glaucomatous eye minus that of the fellow normal eye from ocular hypertension surgery to euthanasia. Integral IOP represents the total, cumulative IOP exposure throughout the entire experiment.

Study Design:

One week prior to induction of glaucoma, RGCs were retrogradely labeled using the fluorescent tracer DiI applied to both superior colliculi.

One week later, unilateral elevation of IOP was induced by injection of a hypertonic saline solution into an episcleral vein. This procedure was referred to as ocular hypertension surgery.

In a first experiment, prior to efficacy studies, the status of RGC loss in "no injection" groups at 2 and 3 weeks after ocular hypertension surgery (4 rats/group, total=8 rats) was assessed.

Exactly 2 weeks after ocular hypertension surgery, a single intravitreal injection of each siRNA was performed.

Animals were euthanized and retinas prepared for analysis of RGC survival at exactly 3 weeks after ocular hypertension surgery.

The density of surviving RGCs was quantified in 12 standard retinal areas.

TABLE C22

Study Design

| Group | n | Increased IOP | IVT Injection (µL/eye) 2 weeks post IOP induction | Dose Volume | Termination (Weeks Post IOP) |
|---|---|---|---|---|---|
| 1 (Intact) | 13 (4 + 9) | No | No | N/A | N/A |
| 2 | 4 | Yes | No | N/A | 2 |
| 3 | 6 | Yes | PBS Vehicle | 5 µL | 3 |
| 4 | 6 | Yes | Negative Control siRNA, 20 µg | 5 µL | 3 |
| 5 | 6 | Yes | CASP2 SIRNA, 20 µg | 5 µL | 3 |

*NA—non-applicable, Group size: n = 5

Quantification of surviving RGC soma: Quantification of RGC bodies was performed in duplicate and in a masked fashion. For RGC density counts, rats were deeply anesthetized and then perfused transcardially with 4% paraformaldehyde (PFA) in 0.1 M phosphate buffer and both eyes were immediately enucleated. Retinas were dissected and flat-mounted on a glass slide with the ganglion cell layer side up. Under fluorescence microscopy, DiI-labeled neurons were counted in 12 standard retinal areas as described.

Results & Discussion

TABLE C23

Percent RGC from intact inference table

| Treat | N | Mean | Std | CV | Dunnett P-value |
|---|---|---|---|---|---|
| PBS | 6 | 62.37 | 5.86 | 9.40 | |
| CASP2_4 | 6 | 81.71 | 14.28 | 17.48 | 0.05 |
| 2wIOP | 4 | 71.25 | 6.75 | 9.47 | 0.19 |
| GFPsiRNA | 6 | 65.75 | 4.97 | 7.57 | 0.68 |
| intact | 13 | 100.00 | 2.84 | 2.84 | 0.00 |

Comparisons to PBS Treated Group

Preservation of RGC in CASP2_4 siRNA-treated eyes with increased IOP was significantly better than in the PBS treated group (1.31 fold higher from the PBS result; p-value=0.05). In GFP siRNA treated group no significant difference was found (p-value=0.68) with respect to PBS treated group.

No significant difference between IOP (2 weeks) to IOP (3 weeks) treated by PBS (p-value=0.19).

Comparisons to IOP (2 Weeks) Group

The intact group has significantly higher RGC density per mm2 than IOP (2w) group (p-value=0.00). No significant differences in RGC density per mm2 were found between IOP (2w) group and other IOP groups that were sacrificed after 3 weeks (p-value range from 0.16 to 0.44).

Comparisons to Intact Group

The intact group has significantly higher RGC density per mm2 than IOP groups that were treated by PBS, GFP siRNA and IOP(2w) without treatment (p-value<0.01). No significant differences in RGC density per mm2 were found between IOP group treated by CASP2_4 siRNA compared to intact group (p-value=0.06).

These data demonstrate that a siRNA targeting Caspase2 provides protection of RGCs from damage induced by increased intraocular pressure and its administration at 2 weeks of increased IOP leads to cessation of further RGC loss.

IOP measurements were carried out as described above.

IOP: The Dunnett approach was used for comparison of the results to PBS treated group. Additional parameters were calculated and analyzed such as: AUC (area under the curve), Mean IOP and Max(IOP) along the duration of measurements.

Most animals show significant increase in IOP at 1-2 weeks after ocular hypertension surgery.

No significant differences in IOP levels were found among operated eyes in treated groups (0.7746). Likewise, no differences in IOP levels were found among contra lateral eyes in treated groups and intact eyes.

The results show that Casp2 siRNA induced neuroprotection even as IOP remained elevated in all treatment groups.

Results: No significant differences between groups were found in all three calculated IOP parameters Example 11

Evaluation of Ocular Neuroprotective Efficacy of siRNA Compound Targeting Caspase 2 in the Axotomy Model The purpose of the present efficacy studies was to use a model of RGC apoptosis induced by axotomy of the optic nerve (ON) in adult Sprague-Dawley rats. The onset and kinetics of RGC death in this model system are very reproducible and allow for the establishment of the neuroprotective efficacy of Casp2_4 siRNA in vivo. Using this method, the time course of RGC death follows a predictable course: cell death begins on day 5 and proceeds to the rapid loss of more than 90% of these neurons by 2 weeks.

Methods

Retrograde labeling of RGCs: For the purpose of this study, RGCs were labeled by application of the retrograde tracer FluoroGold (2%, Fluorochrome, Englewood, Colo.) in the superior colliculus. Briefly, both superior colliculi were exposed and a small piece of gelfoam soaked in FluoroGold was applied to their surface. In adult rats, the time required to obtain full labeling of all RGCs following this procedure is ~1 week. For this reason, optic nerve axotomy and intraocular injection of siRNA molecules were performed one week after retrograde labeling of RGCs.

Optic nerve axotomy: The entire population of RGCs were axotomized by transecting the optic nerve close to the eye (0.5 to 1 mm). Retinal fundus examination was routinely performed after each axotomy to check the integrity of the retinal circulation after surgery. Animals showing signs of compromised blood supply were excluded from the study.

For intravitreal injection 10 µg in 5 pd of PBS each of the reagents, either Casp2_4 siRNA or GFP siRNA were microinjected into the vitreous body 2 mm anterior to the nerve head, perpendicular to the sclera, using a glass micropipette at the time of surgery, day 0, and then repeated at day 7.

Quantification of RGC survival: Experimental and control animals were perfused transcardially with 4% paraformaldehyde at 14 days after optic nerve axotomy. The left retinas (treated) and the right retinas (untreated controls) were dissected out, fixed for an additional 30 min and flat-mounted vitreal side up on a glass slide for examination of the ganglion cell layer. RGCs backfilled with FluoroGold were counted in 12 standard retinal areas. Microglia that may have incorporated FluoroGold after phagocytosis of dying RGCs were distinguished by their characteristic morphology and excluded from our quantitative analyses.

Experimental Design

Test article: CASP2_4L siRNA: a double-stranded 19-mer oligonucleotide chemically modified by 2'-O-methylation of sugar residues on the antisense strand and L-DNA on the sense strand. Targets caspase2 gene in multiple species.

Control Articles

PBS siRNA targeting GFP—a double-stranded 21-mer oligonucleotide chemically modified by 2'O-methylation on both strands.

CNL—siRNA with no match to any known mammalian transcript; a double-stranded 19-mer oligonucleotide chemically modified by 2'O-methylation on both strands. Table C24 shows groups treatments.

TABLE C24

Groups Treatments

| SiRNA | SiRNA Dose | Time of administration (post axotomy) | Time of analysis (post axotomy) | No. of animals per group | Sample preparation |
|---|---|---|---|---|---|
| SiGFP, axotomy (OS) | 10 ug X 2 | Time 0 1 week | 2 weeks | 8 | Flat mount |
| SiCasp2_4, Axotomy (OS) | 10 ug X 2 | Time 0 1 week | 2 weeks | 8 | Flat mount |

Results: The mean number of surviving RGCs in eyes treated with two intravitreal injections of 10 µg Casp2_4 siRNA and subjected to axotomy was 533±24 cells/mm2 at 14 days post injury. These counts were significantly greater than the mean RGC counts in eyes treated with GFP siRNA at the similar regiment and subjected to axotomy, which was 130±7 cells/mm2 at 14 days. In the nonsurgical control eyes, the mean number of RGCs was 2138±91 cells/mm2, which is comparable to the average number of RGCs reported in literature.

TABLE C25

Mean numbers of survival RGC 14 days post injury (n = 6 retinas/group)

| Treatment | GFP | Casp2_4 |
|---|---|---|
| Mean survival RGC (cells/mm2) | 130 | 533 |
| SE | 7 | 24 |
| % of RGC survival from total RGC | 6 | 25 |
| SE | 0.32 | 1.12 |

Data analyses and statistics were performed using the GraphPad Instat software by one-way analysis of variance (ANOVA). All data are given as mean±SE, significantly different at P<0.02.

Conclusions: The increased survival of the RGCs was due to neuroprotective effect by silencing pro-apoptotic Caspase 2 activation and up regulation following axotomy by treatment with siRNA targeting Caspase 2 gene.

Discussion: In the present studies, the Casp2_4 siRNA was neuroprotective for at least 30 days in an optic nerve crush model and for 14 days in axotomy model of RGC loss. Optic nerve crush and axotomy experiments provide a realistic model of acute optic neuropathies.

Non-Invasive Administration of siRNA Compounds Induces Ocular Neuroprotection In-Vivo in Animal Models of Ocular Neuronal Injury Example 12

Evaluation of Ocular Neuroprotective Efficacy of Non-Invasively Administered siRNA Compound Targeting Caspase 2 in the ONC Model Test article: CASP2_4 siRNA (compound of Formula I)

Control Articles:

Methyl Cellulose

CNL—siRNA with no match to any known mammalian transcript; a double-stranded 19-mer oligonucleotide stabilized by 2'O-methylation on both strands.

Design: Retinal ganglion cells (RGC) were selectively labeled first by application of the retrograde tracer FluoroGold to the superior colliculus. One week later, animals were subjected to optic nerve crush injury (ONC). Eye drops were applied every other day during one week (3 times over all). 100 µg/3 µl CNL_1, or Casp2_4 siRNA or 3 µl of MC vehicle were applied, the first dose was applied 10 minutes after ONC. The quantifications of surviving RGCs were carried out at day 7 after ONC by counting FluoroGold-labelled RGCs on flat-mounted retinas.

Results: The mean number of surviving RGCs in eyes treated with 20 µg Casp2_4 siRNA and subjected to optic nerve crush was 445±17 cells/mm2 at 7 days post injury. These counts were significantly greater than the mean RGC counts in eyes treated with either PBS or CNL_1 siRNA and subjected to nerve crush, which were 337±11 cells/mm$^2$, 341.6±13 cells/mm$^2$, respectively, at 7 days. Table C26 shows results. All data are given as mean±standard deviation. Values were compared using one-way analysis of variance (ANOVA) and considered as significantly different at P<0.01.

TABLE C26

Mean numbers of survival RGCs 7 days post injury.

| | CNL_1 | Casp2_4 | MC vehicle |
|---|---|---|---|
| Average | 341.625 | 145.4375 | 337.5 |
| SD | 13.03265 | 17.222331 | 11.3389342 |
| cells/mm2 | 934.6785 | 1218.7073 | 923.392613 |
| Sd | 35.65705 | 17.119921 | 31.0230758 |
| RGC/retina | 26470.1 | 34513.789 | 26150.4788 |
| SD | 1009.808 | 1334.4362 | 878.573505 |
| % total | 26.4701 | 34.513789 | 26.1504788 |
| SD | 1.009808 | 1.3344362 | 0.87857351 |
| Average | 341.625 | 145.4375 | 337.5 |
| SD | 13.03265 | 17.222331 | 11.3389342 |

Conclusions: The increased survival of the RGCs was due to neuroprotective effect of silencing pro-apoptotic Caspase 2 following ONC injury by treatment with eye drops containing siRNA targeting Caspase 2 gene in a methyl cellulose formulation.

Example 13

Evaluation of Ocular Neuroprotective Efficacy of Non-Invasively Administered siRNA Compound Targeting Caspase 2 in the IOP Model Experimental Setup:

Experimental animals: All animal procedures are performed in accordance with the guidelines of the Canadian Council on Animal Care for the use of experimental animals (http://www.ccac.ca/). Surgeries are performed in adult male Brown Norway rats, retired breeders, between 10-12 months of age (300-400 g), under general anesthesia by intraperitoneal injection of 1 ml/kg standard rat cocktail consisting of ketamine (100 mg/ml), xylazine (20 mg/ml) and acepromazine (10 mg/ml).

Retrograde labeling of RGCs: For neuronal survival experiments, RGCs are retrogradely labeled with 3% DiI (1,1'-dioctadecyl-3,3,3',3'-tetramethyl-indocarbocyanine perchlorate; Molecular Probes, Junction City, Oreg.), a fluorescent carbocyanine marker that persists for several months without fading or leakage and does not interfere with the function of labeled cells. For retrograde labeling, both superior colliculi, the main targets of RGCs in the brain, are exposed and a small piece of gelfoam (Pharmacia and Upjohn Inc., Mississauga, ON) soaked in DiI will be applied to their surface. Seven days after DiI application, the time required for labeling the entire RGC population, animals are subjected to ocular hypertension surgery as described below.

Ocular hypertension surgery: Unilateral and chronic elevation of IOP are induced using a method that involves injection of a hypertonic saline solution into an episcleral vein. All the animals involved in this study receive only a single saline vein injection. The eye selected for the procedure is adapted with a plastic ring applied to the ocular equator to confine the saline injection to the limbal plexus. A microneedle (30-50 µm in diameter) is be used to inject 50 µl of sterile 1.85 M NaCl solution through one episcleral vein. The plastic ring temporarily blocks off other episcleral veins forcing the saline solution into the Schlemm's canal to create isolated scarring. Animals are kept in a room with constant low fluorescent light (40-100 lux) to stabilize circadian IOP variation.

Measurement of intraocular pressure (IOP): IOP from glaucomatous and normal (contralateral) eyes is measured in awake animals using a calibrated tonometer (TonoPen XL, Medtronic Solan, Jacksonville, Fla.). IOP is measured every other day for the first two weeks after ocular hypertension surgery; and at least once between week 2 and week 3 after ocular hypertension surgery. Eyes become fragile after intraocular injections in conditions of high IOP (see below), so it is advisable to limit the number of IOP measurements as this involves putting additional pressure on the cornea to get a reliable reading. The mean IOP (mm Hg±S.E.M.) per eye is considered as the average of all IOP readings since the onset of pressure elevation. The maximum IOP measured in each individual eye, glaucomatous or normal contralateral eye is defined as the peak IOP and this value is used to estimate the mean peak IOP for each group. The positive integral IOP is calculated as the area under the IOP curve in the glaucomatous eye minus that of the fellow normal eye from ocular hypertension surgery to euthanasia. Integral IOP represents the total, cumulative IOP exposure throughout the entire experiment.

Intraocular injection of siRNA molecules: Intraocular injections are performed by infusing each siRNA compound at a concentration of 20 µg into the vitreous chamber of the left eye (total injection volume: 5 µl). The right eye serves as contralateral control. In addition, non-operated eyes from naïve rats are used as intact controls. Intravitreal injections are performed using a 10-µl Hamilton syringe adapted with a ~32-gauge glass needle. The needle tip is inserted into the superior hemisphere of the eye, at the level of the pars plana, at a 45° angle through the sclera into the vitreous body. This route of administration avoids retinal detachment or injury to eye structures, including the lens and the iris, which can release factors that induce RGC regeneration and survival. The injection is performed over a period of 2 min and the needle is kept in place for an additional 2 min, after which it is gently removed. Surgical glue (Indermill, Tyco Health Care, Mansfield, Mass., USA) will be used to seal the site of injection.

Topical Eye Drop instillation of siRNA molecules:

Daily during week 3 after IOP induction a 3 µl sample volume of 100 µg of siRNA are applied to the corneal surface bilaterally to the anesthetized animals, by a blunt pipette tip (filter tips 10 µl sterile (short)). The animals are placed in a warm environment to prevent anesthesia-induced hypothermia Quantification of surviving RGC soma: Quantification of RGC bodies is performed in duplicate and in a masked fashion. For RGC density counts, rats are deeply anesthetized and then perfused transcardially with 4% paraformaldehyde (PFA) in 0.1 M phosphate buffer and both eyes are immediately enucleated. Retinas are dissected and flat-mounted on a glass slide with the ganglion cell layer side up. Under fluorescence microscopy, DiI-labeled neurons is counted in 12 standard retinal areas as described.

IOP (intra ocular pressure) is induced and followed for 2 weeks. Then, CASP2_4 or control siRNA are administered by either Eye Drop (siRNA in a 2% methyl cellulose formulation) or IVT (siRNA in PBS) as detailed in the study design in Table C27.

TABLE C27

Study Design

| Group | Treatment | Intravitreal injection (5 uL) | | Eye drops (3 uL/eye) | | Termination |
|---|---|---|---|---|---|---|
| | | Dose | Frequency | Dose | Frequency | |
| 1 | CASP2_4 | 20 ug | Once a week starting at 2 weeks after IOP induction (total 3 times during weeks 3, 4, 5) | NA* | NA | 5 weeks after IOP induction |
| 2 | SiGFP | 20 ug | Once a week starting at 2 | NA* | NA | 5 weeks after IOP induction |

TABLE C27-continued

Study Design

| | | Intravitreal injection (5 uL) | | Eye drops (3 uL/eye) | | |
|---|---|---|---|---|---|---|
| Group | Treatment | Dose | Frequency | Dose | Frequency | Termination |
| 3 | CASP2_4 | 20 ug | weeks after IOP induction (total 3 times during weeks 3, 4, 5) Once after 2 weeks of IOP induction at the beginning of week 3 | 100 ug | Daily during weeks 4 and 5 after IOP induction | 5 weeks after IOP induction |
| 4 | siGFP | 20 ug | Once after 2 weeks of IOP induction at the beginning of week 3 | 100 ug | Daily during weeks 4 and 5 after IOP induction | 5 weeks after IOP induction |
| 5 | CASP2_4 | | | 100 ug | Daily during week 3 after IOP induction | 3 weeks after IOP induction |
| 6 | siGFP | | | 100 ug | Daily during week 3 after IOP induction | 3 weeks after IOP induction |

*NA—non-applicable, Group size: n = 5

The results show that non-invasive delivery of siRNA formulated in a 2% methyl cellulose formulation provides neuroprotection and increases neuronal survival.

Example 14

Rat Optic Nerve Crush (ONC) Model: Comparison of Intravitreal siRNA Delivery to Topical Eye Drop Delivery For optic nerve transsection the orbital optic nerve (ON) of anesthetized rats is exposed through a supraorbital approach, the meninges severed and all axons in the ON transected by crushing with forceps for 10 seconds, 2 mm from the lamina cribrosa.

The siRNA compounds are delivered alone or in combination in 5 uL volume (20 ug/uL) as eye drops. Immediately after optic nerve crush (ONC), 20 ug/10 ul test siRNA or 10 ul PBS is administered by WT to one or both eyes of adult Wistar rats. After that, siRNA is applied to the eye by ED every other day and the levels of siRNA taken up into the dissected and snap frozen whole retinas at 5 hours and 1 day, and later at 2 days, 4 days, 7 days, 14 days and 21 days post injection is determined. Similar experiments are performed in order to test activity and efficacy of siRNA administered via eye drops.

Table C28 below shows an experimental procedure to determine efficacy of test siRNAs (siTEST1; siTEST2) alone or in combination, in the ONC model. Additional dosing parameters, concentrations, termination schedules, formulations and the like are contemplated.

TABLE C28

Study Design

| Group (n = 8) | Right eye (n = 8) | Left eye (n = 8) | termination |
|---|---|---|---|
| 1 and 2 | 20 µg siTEST1 on days 0 and 7 (intravitreal) | 20 µg siGFP on days 0 and 7 (intravitreal) | Day 21 |
| 3 and 4 | 20 µg siTEST1 on days 10 and 20 (intravitreal) | 20 µg siGFP on days 10 and 20 (intravitreal) | Day 30 |
| 5 and 6 | PBS (eye drops) every other day starting from day 0, 3 times/week) | PBS on days 0 and 7 (intravitreal) | Day 21 |
| 7 and 8 | 50 µg siTEST1 (eye drops) every other day starting from day 0, 3 times/week) | 50 µg siGFP (eye drops) every other day starting from day 0, 3 times/week) | Day 10 |
| 9 and 10 | 50 µg siTEST1 (eye drops) every other day starting from day 0, 3 times/week) | 50 µg siGFP (eye drops) every other day starting from day 0, 3 times/week) | Day 21 |
| 11 and 12 | 50 µg siTEST2 (eye drops) every other day starting from day 0, 3 times/week) | 50 µg siGFP (eye drops) every other day starting from day 0, 3 times/week) | Day 21 |
| 13 and 14 | 20 µg siTEST1 + 20 µg siTEST2 (eye drops) every other day | 40 µg siGFP on days 0, 7 and 20 (eye drops) every other day starting from day | Day 21 |

TABLE C28-continued

Study Design

| Group (n = 8) | Right eye (n = 8) | Left eye (n = 8) | termination |
|---|---|---|---|
| 15 and 16 | starting from day 0, 3 times/week) 20 μg siTEST + 20 μg siTEST2 on days 0, and 10 (intravitreal) n = 4 | 0, 3 times/week) 40 μg siGFP on days 0 and 10 (intravitreal) n = 4 | Day 21 |

Results: According to the results that are obtained in this study non-invasive delivery of siRNA compound designed for down regulation of a target gene provides neuroprotection and increases neuronal survival in the retina.

Tables B1-B26 disclose oligonucleotide pairs of sense and antisense nucleic acids useful in synthesizing unmodified or chemically modified siRNA compounds. The tables disclose the position of the sense strand along the mRNA for at least one variant.

Lengthy table referenced here

US09121020-20150901-T00001

Please refer to the end of the specification for access instructions.

Lengthy table referenced here

US09121020-20150901-T00002

Please refer to the end of the specification for access instructions.

Lengthy table referenced here

US09121020-20150901-T00003

Please refer to the end of the specification for access instructions.

Lengthy table referenced here

US09121020-20150901-T00004

Please refer to the end of the specification for access instructions.

Lengthy table referenced here

US09121020-20150901-T00005

Please refer to the end of the specification for access instructions.

Lengthy table referenced here

US09121020-20150901-T00006

Please refer to the end of the specification for access instructions.

Lengthy table referenced here

US09121020-20150901-T00007

Please refer to the end of the specification for access instructions.

Lengthy table referenced here

US09121020-20150901-T00008

Please refer to the end of the specification for access instructions.

Lengthy table referenced here

US09121020-20150901-T00009

Please refer to the end of the specification for access instructions.

Lengthy table referenced here

US09121020-20150901-T00010

Please refer to the end of the specification for access instructions.

Lengthy table referenced here

US09121020-20150901-T00011

Please refer to the end of the specification for access instructions.

| | |
|---|---|
| Lengthy table referenced here | Lengthy table referenced here |
| US09121020-20150901-T00012 | US09121020-20150901-T00020 |
| Please refer to the end of the specification for access instructions. | Please refer to the end of the specification for access instructions. |

| | |
|---|---|
| Lengthy table referenced here | Lengthy table referenced here |
| US09121020-20150901-T00013 | US09121020-20150901-T00021 |
| Please refer to the end of the specification for access instructions. | Please refer to the end of the specification for access instructions. |

| | |
|---|---|
| Lengthy table referenced here | Lengthy table referenced here |
| US09121020-20150901-T00014 | US09121020-20150901-T00022 |
| Please refer to the end of the specification for access instructions. | Please refer to the end of the specification for access instructions. |

| | |
|---|---|
| Lengthy table referenced here | Lengthy table referenced here |
| US09121020-20150901-T00015 | US09121020-20150901-T00023 |
| Please refer to the end of the specification for access instructions. | Please refer to the end of the specification for access instructions. |

| | |
|---|---|
| Lengthy table referenced here | Lengthy table referenced here |
| US09121020-20150901-T00016 | US09121020-20150901-T00024 |
| Please refer to the end of the specification for access instructions. | Please refer to the end of the specification for access instructions. |

| | |
|---|---|
| Lengthy table referenced here | Lengthy table referenced here |
| US09121020-20150901-T00017 | US09121020-20150901-T00025 |
| Please refer to the end of the specification for access instructions. | Please refer to the end of the specification for access instructions. |

| | |
|---|---|
| Lengthy table referenced here | Lengthy table referenced here |
| US09121020-20150901-T00018 | US09121020-20150901-T00026 |
| Please refer to the end of the specification for access instructions. | Please refer to the end of the specification for access instructions. |

| | |
|---|---|
| Lengthy table referenced here | Lengthy table referenced here |
| US09121020-20150901-T00019 | US09121020-20150901-T00027 |
| Please refer to the end of the specification for access instructions. | Please refer to the end of the specification for access instructions. |

Lengthy table referenced here

US09121020-20150901-T00028

Please refer to the end of the specification for access instructions.

Lengthy table referenced here

US09121020-20150901-T00029

Please refer to the end of the specification for access instructions.

Lengthy table referenced here

US09121020-20150901-T00030

Please refer to the end of the specification for access instructions.

Lengthy table referenced here

US09121020-20150901-T00031

Please refer to the end of the specification for access instructions.

Lengthy table referenced here

US09121020-20150901-T00032

Please refer to the end of the specification for access instructions.

Lengthy table referenced here

US09121020-20150901-T00033

Please refer to the end of the specification for access instructions.

Lengthy table referenced here

US09121020-20150901-T00034

Please refer to the end of the specification for access instructions.

Lengthy table referenced here

US09121020-20150901-T00035

Please refer to the end of the specification for access instructions.

Lengthy table referenced here

US09121020-20150901-T00036

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US09121020B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09121020B2). An electronic copy of the "Sequence Listing" will also be available from the USPTO upon request and payment of the fee set forth in 37 CFR 1.19(b)(3).

The invention claimed is:

1. A method of treating a patient suffering, or at risk of suffering, from an ocular disease, an ocular disorder or an ocular injury, comprising administering to the patient a therapeutically effective amount of a double-stranded oligonucleotide having the structure:

```
                    (sense strand; SEQ ID NO: 9015)
    5' iB-GCCAGAAUGUGGAACUCCU 3'

(antisense strand; SEQ ID NO: 9516)
    3' CGGUCUUACACCUUGAGGA 5'
``` wherein each of A, C, U and G is a nucleotide and each consecutive nucleotide is joined to the next nucleotide by a phosphodiester bond;
wherein the sense strand comprises, counting from the 5' terminus, an unmodified ribonucleotide at each of positions 1, 2, 3, 4, 5, 6, 7, 8, 9, 10, 11, 12, 13, 14, 15, 16, 17 and 19, a L-deoxycytidine at position 18, and an inverted deoxyabasic moiety (iB) covalently attached at the 5' terminus; and
wherein the antisense strand comprises, counting from the 5' terminus, a 2'-O-Methyl sugar-modified ribonucleotide at each of positions 2, 4, 6, 8, 11, 13, 15, 17 and 19 and an unmodified ribonucleotide at positions 1, 3, 5, 7, 9, 10, 12, 14, 16 and 18; or a pharmaceutically acceptable salt of such double-stranded oligonucleotide; and a pharmaceutically acceptable carrier.

2. The method of claim 1, wherein the ocular disease, ocular disorder, or ocular injury is associated with pathological abnormalities/changes in the tissues of the visual system.

3. The method of claim 2, wherein the pathological abnormalities/changes comprise loss of retinal ganglion cells or retinal ganglion cell damage.

4. The method of claim 3, wherein the loss of retinal ganglion cells or the retinal ganglion cell damage is mediated by elevated intraocular pressure (IOP).

5. The method of claim 1, wherein the ocular disease, ocular disorder, or ocular injury is selected from the group consisting of elevated intraocular pressure (IOP), glaucoma, diabetic retinopathy (DR), diabetic macular edema (DME), age related macular degeneration (AMD), optic neuritis, central retinal vein occlusion, brunch retinal vein occlusion, optic nerve injury, retinopathy of prematurity (ROP), retinitis pigmentosa (RP), retinal ganglion degeneration, macular degeneration and an optic neuropathy.

6. The method of claim 5, wherein the ocular disease, ocular disorder, or ocular injury comprises an optic neuropathy.

7. The method of claim 6, wherein the optic neuropathy is selected from the group consisting of ischemic optic neuropathy (ION), hereditary optic neuropathy, Leber's hereditary optic neuropathy, metabolic optic neuropathy, neuropathy due to a toxic agent, neuropathy caused by an adverse drug reaction and neuropathy caused by a vitamin deficiency.

8. The method of claim 7, wherein the optic neuropathy comprises ischemic optic neuropathy.

9. The method of claim 8, wherein the ischemic optic neuropathy comprises anterior ischemic optic neuropathy and/or posterior ischemic optic neuropathy.

10. The method of claim 1, wherein the oligonucleotide is administered in an amount effective to down-regulate the expression of a CASP2 gene in an ocular cell.

11. The method of claim 1, wherein the oligonucleotide is administered as a cream, a foam, a paste, an ointment, an emulsion, a liquid solution, an eye drop, a gel, spray, a suspension, a microemulsion, microspheres, microcapsules, nanospheres, nanoparticles, lipid vesicles, liposomes, polymeric vesicles, a patch, or a contact lens.

12. The method of claim 11, wherein the oligonucleotide is administered as a liquid solution.

13. The method of claim 12, wherein the liquid solution is administered by intravitreal injection.

14. A method of providing neuroprotection in a retinal cell in a patient suffering, or at risk of suffering, from an ocular disease, an ocular disorder or an ocular injury, comprising administering to the patient a therapeutically effective amount of a double-stranded oligonucleotide having the structure:

```
                    (sense strand; SEQ ID NO: 9015)
    5' iB-GCCAGAAUGUGGAACUCCU 3'

(antisense strand; SEQ ID NO: 9516)
    3' CGGUCUUACACCUUGAGGA 5'
``` wherein each of A, C, U and G is a nucleotide and each consecutive nucleotide is joined to the next nucleotide by a phosphodiester bond;
wherein the sense strand comprises, counting from the 5' terminus, an unmodified ribonucleotide at each of positions 1, 2, 3, 4, 5, 6, 7, 8, 9, 10, 11, 12, 13, 14, 15, 16, 17 and 19, a L-deoxycytidine at position 18, and an inverted deoxyabasic moiety (iB) covalently attached at the 5' terminus; and
wherein the antisense strand comprises, counting from the 5' terminus, a 2'-O-Methyl sugar-modified ribonucleotide at each of positions 2, 4, 6, 8, 11, 13, 15, 17 and 19 and an unmodified ribonucleotide at positions 1, 3, 5, 7, 9, 10, 12, 14, 16 and 18; or a pharmaceutically acceptable salt of such double-stranded oligonucleotide; and a pharmaceutically acceptable carrier.

15. The method of claim 14, wherein the patient is suffering from an ocular disease, ocular disorder, or ocular injury selected from the group consisting of elevated intraocular pressure (IOP), glaucoma, diabetic retinopathy (DR), diabetic macular edema (DME), age related macular degeneration (AMD), optic neuritis, central retinal vein occlusion, brunch retinal vein occlusion, optic nerve injury, retinopathy of prematurity (ROP), retinitis pigmentosa (RP), retinal ganglion degeneration, macular degeneration and an optic neuropathy.

16. The method of claim 15, wherein the ocular disease, ocular disorder, or ocular injury comprises an optic neuropathy.

17. The method of claim 16, wherein the optic neuropathy is selected from the group consisting of ischemic optic neuropathy (ION), hereditary optic neuropathy, Leber's hereditary optic neuropathy, metabolic optic neuropathy, neuropathy due to a toxic agent, neuropathy caused by an adverse drug reaction and neuropathy caused by a vitamin deficiency.

18. The method of claim 17, wherein the neuropathy comprises ischemic optic neuropathy.

19. The method of claim 18, wherein the ischemic optic neuropathy comprises anterior ischemic optic neuropathy and/or posterior ischemic optic neuropathy.

20. The method of claim 14, wherein the oligonucleotide is administered in an amount effective to down-regulate the expression of a CASP2 gene in an ocular cell.

21. The method of claim 14, wherein the oligonucleotide is administered as a cream, a foam, a paste, an ointment, an emulsion, a liquid solution, an eye drop, a gel, spray, a suspension, a microemulsion, microspheres, microcapsules, nanospheres, nanoparticles, lipid vesicles, liposomes, polymeric vesicles, a patch, or a contact lens.

22. The method of claim 21, wherein the oligonucleotide is administered as a liquid solution.

23. The method of claim 22, wherein the liquid solution is administered by intravitreal injection.

* * * * *